United States Patent
Sainz et al.

(10) Patent No.: US 11,787,767 B2
(45) Date of Patent: Oct. 17, 2023

(54) MODULATORS OF MAS-RELATED G-PROTEIN RECEPTOR X4 AND RELATED PRODUCTS AND METHODS

(71) Applicant: Escient Pharmaceuticals, Inc., San Diego, CA (US)

(72) Inventors: Marcos Sainz, San Diego, CA (US); Adam Yeager, San Diego, CA (US); Brandon Selfridge, San Diego, CA (US); Esther Martinborough, San Diego, CA (US); Marcus Boehm, San Diego, CA (US); Liming Huang, San Diego, CA (US)

(73) Assignee: ESCIENT PHARMACEUTICALS, INC., San Diego, CA (US)

(*) Notice: Subject to any disclaimer, the term of this patent is extended or adjusted under 35 U.S.C. 154(b) by 133 days.

(21) Appl. No.: 17/231,834

(22) Filed: Apr. 15, 2021

(65) Prior Publication Data

US 2021/0340106 A1    Nov. 4, 2021

Related U.S. Application Data

(60) Provisional application No. 63/011,964, filed on Apr. 17, 2020.

(51) Int. Cl.

| | | |
|---|---|---|
| *C07D 215/227* | (2006.01) | |
| *C07D 209/34* | (2006.01) | |
| *C07D 209/46* | (2006.01) | |
| *C07D 217/24* | (2006.01) | |
| *C07D 413/12* | (2006.01) | |

(52) U.S. Cl.
CPC ....... *C07D 215/227* (2013.01); *C07D 209/34* (2013.01); *C07D 209/46* (2013.01); *C07D 217/24* (2013.01); *C07D 413/12* (2013.01)

(58) Field of Classification Search
CPC .............. C07D 215/227; C07D 209/34; C07D 209/46; C07D 217/24; C07D 413/12
See application file for complete search history.

(56) References Cited

U.S. PATENT DOCUMENTS

| | | | | |
|---|---|---|---|---|
| 5,177,075 A | * | 1/1993 | Suto ..................... | C07D 405/12 546/141 |
| 6,110,934 A | | 8/2000 | Harling et al. | |
| 10,357,489 B2 | * | 7/2019 | Alexander .............. | A61P 35/02 |
| 10,702,518 B2 | * | 7/2020 | Sdelci ..................... | A61P 35/00 |
| 2017/0231973 A1 | | 8/2017 | Dahl | |

FOREIGN PATENT DOCUMENTS

| | | |
|---|---|---|
| CN | 107033087 A | 8/2017 |
| CN | 108689937 A | 10/2018 |
| CN | 108863892 A | 11/2018 |
| CN | 110903224 A | 3/2020 |
| KR | 10-2019-0126525 A | 11/2019 |
| WO | 01/049289 A1 | 7/2001 |
| WO | 01/91796 A2 | 12/2001 |
| WO | 2017/133258 A1 | 8/2017 |
| WO | 2019/147783 A1 | 8/2019 |
| WO | 2020/198537 A1 | 10/2020 |
| WO | 2021/013163 A1 | 1/2021 |

OTHER PUBLICATIONS

Pellicciari, Chem Med Chem, 2008, vol. 3, 914-923. (Year: 2008).*
Pellicciari et al., "On the Way to Selective PARP-2 Inhibitors. Design, Synthesis, and Preliminary Evaluation of a Series of Isoquinolinone Derivatives", 2008, ChemMedChem, vol. 3, pp. 914-923,.
Li et al., "Synthesis and Evaluation of Novel α-Aminoamides Containing an Indole Moiety for the Treatment of Neuropathic Pain", Molecules, 2016, 21, 793, pp. 1-8.

* cited by examiner

Primary Examiner — D Margaret M Seaman
(74) Attorney, Agent, or Firm — Seed IP Law Group LLP

(57) ABSTRACT

Methods are provided for modulating MRGPR X4 generally, or for treating a MRGPR X4 dependent condition more specifically, by contacting the MRGPR X4 or administering to a subject in need thereof, respectively, an effective amount of a compound having the structure of Formula (I):

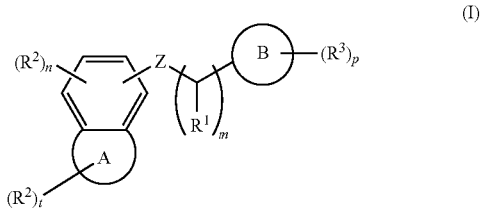

(I)

or a pharmaceutically acceptable isomer, racemate, hydrate, solvate, isotope, or salt thereof, wherein m, n, p, t, A, B, Z, $R^1$, $R^2$ and $R^3$ are as defined herein. Pharmaceutical compositions containing such compounds, as well as to compounds themselves, are also provided.

8 Claims, No Drawings

MODULATORS OF MAS-RELATED G-PROTEIN RECEPTOR X4 AND RELATED PRODUCTS AND METHODS

BACKGROUND

Technical Field

The invention relates to modulators of the Mas-related G-protein coupled receptor X4, to products containing the same, as well as to methods of their use and preparation.

Description of the Related Art

Mas-related G protein receptors (MRGPRs) are a group of orphan receptors with limited expression in very specialized tissues. Very little is known about the function of most of these receptors. There are eight related receptors in this class expressed in humans, only four of which have readily identifiable orthologs in other species (i.e., MRGPR D, E, F and G). The other four receptors (MRGPR X1, X2, X3 and X4) have no counterpart, based on homology, in species other than human.

BRIEF SUMMARY

This invention is based, in part, on the identification that functionally in mice MRGPR A1 corresponds, at least in part, to the human MRGPR X4. These receptors mediate disorders including chronic itch (e.g., pruritus), inflammation disorders, autoimmunity, skin disorders, cardiovascular disease, lung inflammation/COPD, and adverse skin reactions to drugs. More specifically, both MRGPR A1 and MRGPR X4 are expressed in sensory neurons, skin melanocytes, dendritic cells, polymorphonuclear cells, macrophages, bronchial epithelial cells, lung smooth muscle and dorsal root ganglia. It has now been identified that both MRGPR A1 and MRGPR X4 are receptors for (or sensitive to activation by) circulating bilirubin and its metabolites, and thus are important for itch sensation in conditions of elevated bilirubin such as cholestatic pruritus. In addition, MRGPR X4 is activated by multiple additional components of bile including bile acids and metabolites thereof and heme metabolites including bilirubin and urobilin. Bile acids and bilirubin are highly elevated in cholestatic pruritus while urobilin, which is a potent mediator of itch induction in mouse model, and thus may be important for itch sensation in conditions of elevated urobilin such as uremic pruritus. Furthermore, MRGPR X4 is a receptor for urobilin, which is a potent mediator of itch induction in mouse model, and thus may be important for itch sensation in conditions of elevated urobilin such as uremic pruritus. Thus, modulating MRGPR X4 allows for treatment of autoimmune diseases such as psoriasis, multiple sclerosis, Steven Johnson's Syndrome, and other chronic itch conditions as explained in more detail below.

Accordingly, in an embodiment, methods are provided for modulating a MRGPR X4 by contacting the MRGPR X4 with an effective amount of a compound having the structure of Formula (I):

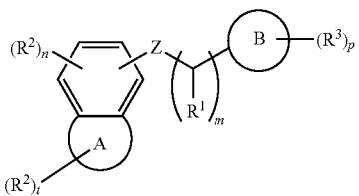

or a pharmaceutically acceptable isomer, racemate, hydrate, solvate, isotope, or salt thereof, wherein n, m, p, t, A, B, Z, R', $R^2$, and $R^3$ are as defined below.

In another embodiment, methods are provided for treating a MRGPR X4 dependent condition by administering to a subject in need thereof an effective amount of a compound having the structure of Formula (I), or a pharmaceutically acceptable isomer, racemate, hydrate, solvate, isotope, or salt thereof.

In more specific embodiments, the MRGPR X4 dependent condition is one or more of an itch associated condition, a pain associated condition, an inflammation-associated condition, or an autoimmune disorder.

In another embodiment, pharmaceutical compositions are provided comprising a compound having the structure of Formula (I), or a pharmaceutically acceptable isomer, racemate, hydrate, solvate, isotope, or salt thereof, in combination with a pharmaceutically acceptable excipient.

In another embodiment, pharmaceutical compositions are provided having one or more of the structures disclosed herein, or a pharmaceutically acceptable isomer, racemate, hydrate, solvate, isotope, or salt thereof.

In yet more specific embodiments, pharmaceutical compositions are provided further comprising a second therapeutic agent, wherein the second therapeutic agent is ursodeoxycholic acid (UDCA), norUrsodeoxycholic acid, cholestyramine, stanozolol, naltrexone, rifampicin, Alisol B 23-acetate (AB23A), curcumin, dihydroartemisinin, fenofibrate, bezafibrate, metronidazole, methotrexate, colchicine, metformin, betaine, glucagon, naltrexone, a farnesoid X-receptor (FXR) agonist, a peroxisome proliferator-activated receptor (PPAR) agonist, a thyroid hormone receptor beta (TRβ) agonist, or any combination thereof.

In another embodiment, compounds are provided having the structure of Formula (IX):

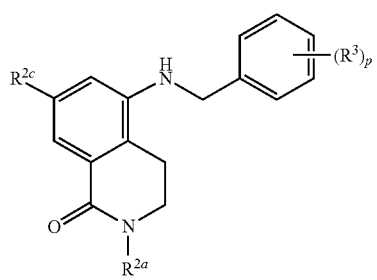

or a pharmaceutically acceptable isomer, racemate, hydrate, solvate, isotope, or salt thereof, wherein p, $R^{2a}$, $R^{2c}$, and $R^3$ are as defined below.

In still another embodiment, compounds are provided having the structure of Formula (X):

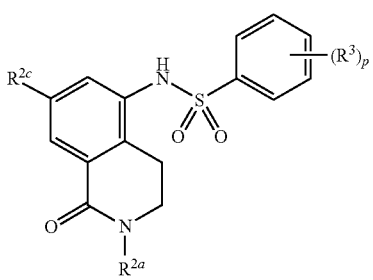

(X)

or a pharmaceutically acceptable isomer, racemate, hydrate, solvate, isotope, or salt thereof, wherein p, $R^{2a}$, $R^{2c}$, and $R^3$ are as defined below.

In yet another embodiment, compounds are provided having the structure of Formula (XII):

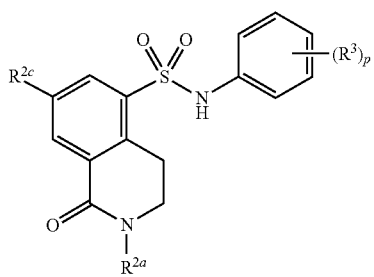

(XII)

or a pharmaceutically acceptable isomer, racemate, hydrate, solvate, isotope, or salt thereof, wherein p, $R^{2a}$, $R^{2c}$, and $R^3$ are as defined below.

In another embodiment, compounds are provided having the structure of Formula (XIII):

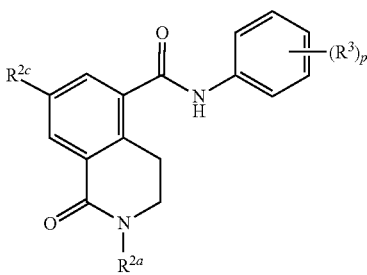

(XIII)

or a pharmaceutically acceptable isomer, racemate, hydrate, solvate, isotope, or salt thereof, wherein $R^{2a}$, $R^{2c}$, and $R^3$ are as defined below.

In another embodiment, compounds are provided having one or more of the structures disclosed herein, or a pharmaceutically acceptable isomer, racemate, hydrate, solvate, isotope, or salt thereof.

DETAILED DESCRIPTION

As mentioned above, the invention relates to modulators of the MRGPR X4, to products containing the same, as well as to methods of their use and preparation. This invention is based, in part, on the identification that in mice MRGPR A1 functionally corresponds to the human MRGPR X4. These receptors mediate disorders including chronic and intermittent itch (e.g., pruritus), inflammation disorders, autoimmunity, skin disorders, and adverse skin reactions to drugs and infectious diseases. More specifically, both MRGPR A1 and MRGPR X4 are expressed in sensory neurons and dorsal root ganglia. It has now been identified that both MRGPR A1 and MRGPR X4 are receptors for (or sensitive to activation by) circulating bilirubin and its metabolites, and thus are important for itch sensation in conditions of elevated bilirubin such as cholestatic pruritus and end-stage renal failure. In addition, MRGPR X4 is also activated by bile acids, which are also elevated in cholestatic pruritus. Furthermore, urobilin, an oxidative product of the heme metabolite urobilinogen solely excreted by the kidney, is a potent agonist of MRGPR X4 and pruritogen, and thus may be important for itch sensation in conditions of elevated urobilin such as uremic pruritus, kidney disease and end-stage renal failure. Thus, modulating MRGPR X4 allows for treatment of autoimmune diseases such as psoriasis, multiple sclerosis, Steven Johnson's Syndrome, atopic disorders such as atopic dermatitis and other chronic itch conditions as explained in more detail below.

MRGPRs appear to be sensory receptors that recognize their external environment to exogenous or endogenous signals/chemicals. These receptors likely respond to multiple chemical ligands/agonists. For example, MRGPR X4 recognizes bilirubin, bile acids, and urobilin as agonist signals. In certain embodiments, molecules of this invention modulate MRGPR X4 by functioning as inverse agonists that are capable of blocking multiple chemical entities, and/or as competitive antagonists that can specifically block individual ligands. In one embodiment, such modulations are selective against other MRGPRs, such as MRGPR X1, X2 and/or X3.

Accordingly, in one embodiment, methods for modulating a MRGPR X4 are provided comprising contacting the MRGPR X4 with an effective amount of compound having the structure of Formula (I):

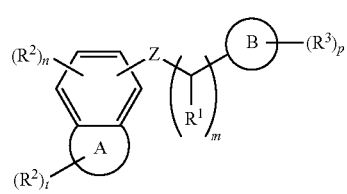

(I)

or a pharmaceutically acceptable isomer, racemate, hydrate, solvate, isotope, or salt thereof, wherein:

A is a 5- or 6-membered carbocycle or a 5- or 6-membered heterocycle; B is a carbocycle or a heterocycle;

Z is —O—, —CH$_2$—O—, —S—, —N(R')—, —N(R')S(O)$_2$—, —S(O)$_2$N(R')—, —N(R')C(O)—, or —C(O)N(R')—;

each $R^1$ is, independently, H or alkyl;

each $R^2$ is, independently, halo, alkyl, haloalkyl, or aralkyl, or two $R^2$, together, form =O or =S;

each $R^3$ is, independently, halo, alkyl, haloalkyl, alkoxy, haloalkoxy, carbocycle or heterocycle, —CN, —(CH$_2$)$_q$C(O)OR$^4$, —(CH$_2$)$_q$NHR$^5$, —(CH$_2$)$_q$OR$^6$, —C(O)NR$^7$R$^8$, or a carboxylic acid isostere;

each $R^4$, $R^5$, $R^6$, and $R^7$ is, independently, H or alkyl;

each $R^8$ is, independently, H, —SO$_2$CH$_3$, carbocycle, heterocycle, or alkyl, wherein each $R^8$ is independently substituted with 0, 1, 2, or 3 $R^9$;

each $R^9$ is —OH, —CN, —NR'R", —C(O)OH, —C(O)NR'R", —SO$_2$OH, alkoxy, carbocycle, or heterocycle;
each R' is, independently, H or alkyl;
each R" is, independently, H or alkyl;
m is 0-2;
n is 0-3;
p is 0-3;
q is 0-6; and
t is 0-6.

"Modulating" MRGPR X4 means that the compound interacts with the MRGPR X4 in a manner such that it functions as an inverse agonist to the receptor, and/or as a competitive antagonist to the receptor. In one embodiment, such modulation is partially or fully selective against other MRGPRs, such as MRGPR X1, X2 and/or X3.

"MRGPR" refers to one or more of the Mas-related G protein coupled receptors, which are a group of orphan receptors with limited expression in very specialized tissues (e.g., in sensory neurons and dorsal root ganglia) and barrier tissues. There are eight related receptors in this class expressed in humans, only 4 of which have readily identifiable orthologs in other species (i.e., MRGPR D, E, F and G). The other four receptors (MRGPR X1, X2, X3 and X4) have no counterpart, based on homology, in non-human species.

"Effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

"Alkyl" means a saturated or unsaturated straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of saturated straight chain alkyl groups include, but are not limited to, methyl, ethyl, n-propyl, n-butyl, n-pentyl-, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. An unsaturated alkyl includes alkenyl and alkynyl as defined below.

"Alkenyl" means a straight chain or branched alkenyl group having from 2 to 8 carbon atoms, in some embodiments from 2 to 6 carbon atoms, in some embodiments from 2 to 4 carbon atoms, and in some embodiments from 2 to 3 carbon atoms. Alkenyl groups are unsaturated hydrocarbons that contain at least one carbon-carbon double bond. Examples of lower alkenyl groups include, but are not limited to, vinyl, propenyl, butenyl, pentenyl, and hexenyl.

"Alkynyl" means a straight chain or branched alkynyl group having from 2 to 8 carbon atoms, in some embodiments from 2 to 6 carbon atoms, in some embodiments from 2 to 4 carbon atoms, and in some embodiments from 2 to 3 carbon atoms. Alkynyl groups are unsaturated hydrocarbons that contain at least one carbon-carbon triple bond. Examples of alkynyl groups include, but are not limited to, ethynyl, propynyl, butynyl, pentynyl, and hexynyl.

"Halo" or "halogen" refers to fluorine, chlorine, bromine, and iodine.

"Hydroxy" refers to —OH.
"Cyano" refers to —CN.
Amino refers to —NH2, —NHalkyl or N(alkyl)2, wherein alkyl is as defined above. Examples of amino include, but are not limited to —NH2, —NHCH3, —N(CH3)2, and the like.

"Haloalkyl" refers to alkyl as defined above with one or more hydrogen atoms replaced with halogen. Examples of lower haloalkyl groups include, but are not limited to, —CF3, —CHF2, and the like.

"Alkoxy" refers to alkyl as defined above joined by way of an oxygen atom (i.e., —O— alkyl). Examples of alkoxy groups include, but are not limited to, methoxy, ethoxy, n-propoxy, n-butoxy, isopropoxy, sec-butoxy, tert-butoxy, and the like.

"Haloalkoxy" refers to haloalkyl as defined above joined by way of an oxygen atom (i.e., —O— haloalkyl). Examples of lower haloalkoxy groups include, but are not limited to, —OCF3, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Aryl" groups are cyclic aromatic hydrocarbons that do not contain heteroatoms. Representative aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like). In one embodiment, aryl is phenyl or naphthyl, and in another embodiment aryl is phenyl.

"Carbocycle" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring may give rise to aromaticity. In one embodiment, carbocycle includes cycloalkyl as defined above. In another embodiment, carbocycle includes aryl as defined above.

"Heterocycle" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl, and 2,3-dihydro indolyl.

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quaternary carbon are optically active isomers, which may be purified from the respective racemate and/or synthesized by appropriate chiral synthesis.

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine-19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, Int. J. Pharm., 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenyl acetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In another embodiment, a method of treating a subject having a MRGPR X4 dependent condition is provided, the method comprising administering to the subject a pharmaceutically effective amount of a compound having the structure of Formula (I):

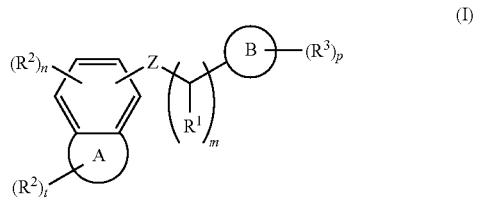

or a pharmaceutically acceptable isomer, racemate, hydrate, solvate, isotope, or salt thereof, wherein:

A is a 5- or 6-membered carbocycle or a 5- or 6-membered heterocycle;

B is a carbocycle or a heterocycle;

Z is —O—, —$CH_2$—O—, —S—, —N(R')—, —N(R')S$(O)_2$—, —S$(O)_2$N(R')—, —N(R')C(O)—, or —C(O)N(R')—;

each $R^1$ is, independently, H or alkyl;

each $R^2$ is, independently, halo, alkyl, haloalkyl, or aralkyl, or two $R^2$, together, form =O or =S;

each $R^3$ is, independently, halo, alkyl, haloalkyl, alkoxy, haloalkoxy, carbocycle or heterocycle, —CN, —$(CH_2)_q$C(O)O$R^4$, —$(CH_2)_q$NH$R^5$, —$(CH_2)_q$O$R^6$, —C(O)N$R^7R^8$, or a carboxylic acid isostere;

each $R^4$, $R^5$, $R^6$, and $R^7$ is, independently, H or alkyl;

each $R^8$ is, independently, H, —$SO_2CH_3$, carbocycle, heterocycle, or alkyl, wherein each $R^8$ is independently substituted with 0, 1, 2, or 3 $R^9$;

each $R^9$ is —OH, —CN, —NR'R", —C(O)OH, —C(O)NR'R", —$SO_2$OH, alkoxy, carbocycle, or heterocycle;

each R' is, independently, H or alkyl;

each R" is, independently, H or alkyl;

m is 0-2;

n is 0-3;

p is 0-3;

q is 0-6; and t is 0-6.

As used herein, the phrase "MRGPR X4 dependent condition" means a condition where the activation, over sensitization, or desensitization of MRGPR X4 by a natural or synthetic ligand initiates, mediates, sustains, or augments a pathological condition. For example, it is known that some itch or pain sensations are caused by elevated bilirubin and its metabolites or bile acids in patients suffering from pruritus, atopic or other autoimmune or inflammatory diseases. It has been found that MRGPR X4 is sensitive to (or activated by) bilirubin and its metabolites, including urobilin, or bile acids. Without limited by theory, it is to be understood that by modulating MRGPR X4, the itch or pain sensations can be eased.

In some embodiments, the MRGPR X4 dependent condition is a condition that is caused by the activation of MRGPR X4 by a bile acid. As used herein, the term "bile acid" includes primary bile acids (e.g., cholic acid, chenodeoxycholic acid), conjugated bile acids, also referred to as bile salts (e.g., taurocholic acid, glycocholic acid, taurochenodeoxycholic acid, glycochenodeoxycholic acid), secondary bile acids (e.g., deoxycholic acid, lithocholic acid), and bile acid analogs. In some embodiments, a bile acid analog is a farnesoid X-receptor (FXR) agonist. Thus, the compounds of the present disclosure may be used for treating an MRGPR X4 dependent condition caused by activation of MRGPR X4 by a bile acid and that would benefit from modulating MRGPR X4.

In some embodiments, the MRGPR X4 dependent condition is an itch associated condition, a pain associated condition, an autoimmune condition, or an autoimmune or inflammatory disorder.

As used herein, the phrase "itch associated condition" means pruritus (including acute and chronic pruritus) associated with any condition. The itch sensation can originate, e.g., from the peripheral nervous system (e.g., dermal or neuropathic itch) or from the central nervous system (e.g., neuropathic, neurogenic or psychogenic itch). Thus, in one embodiment, the method of present invention is provided to treat an itch associated condition, such as chronic itch; cholestatic pruritus; contact dermatitis; Allergic blepharitis; Anemia; Atopic dermatitis; Bullous pemphigoid; Candidiasis; Chicken pox; Cholestasis; end-stage renal failure; hemodialysis; Contact dermatitis, Atopic Dermatitis; Dermatitis herpetiformis; Diabetes; Drug allergy, Dry skin; Dyshidrotic dermatitis; Ectopic eczema; Erythrasma; Folliculitis; Fungal skin infection;

Hemorrhoids; Herpes; HIV infection; Hodgkin's disease; Hyperthyroidism; Iron deficiency anemia; Kidney disease; Leukemia, porphyrias; Liver disease, including primary biliary cholangitis, primary sclerosing cholangitis, Alagille syndrome, Progressive familial intrahepatic cholestasis, Intrahepatic cholestasis of pregnancy, nonalcoholic steatohepatitis (NASH), nonalcoholic fatty liver disease (NAFLD), biliary atresia, chronic B hepatitis, drug-chronic viral hepatitis, induced liver injury (DILI), liver fibrosis, cholestatic liver disease, and alcoholic liver disease; Lymphoma; Malignancy; Multiple myeloma; Neurodermatitis; Onchocerciasis; Paget's disease; Pediculosis; Polycythemia rubra vera; Lichen Planus; Lichen Sclerosis; Pruritus ani; Pseudorabies; Psoriasis; Rectal prolapse; Scabies; Schistosomiasis; Scleroderma, Severe stress, Stasia dermatitis; Swimmer's itch; Thyroid disease; Tinea cruris; Uremic Pruritus; Rosacea; Cutaneous amyloidosis; Scleroderma; Acne; wound healing; ocular itch; and Urticaria.

As used herein, the phrase "pain associated condition" means any pain due to a medical condition. Thus, in one embodiment, the method of present invention is provided to treat a pain associated condition, such as Acute Pain, Advanced Prostate Cancer, AIDS-Related Pain, Ankylosing Spondylitis, Arachnoiditis, Arthritis, Arthrofibrosis, Ataxic Cerebral Palsy, Autoimmune Atrophic Gastritis, Avascular Necrosis, Back Pain, Behcet's Disease (Syndrome), Burning Mouth Syndrome, Bursitis, Cancer Pain, Carpal Tunnel, Cauda *Equina* Syndrome, Central Pain Syndrome, Cerebral Palsy, Cervical Stenosis, Charcot-Marie-Tooth (CMT) Disease, Chronic Fatigue Syndrome (CFS), Chronic Functional Abdominal Pain (CFAP), Chronic Pain, Chronic Pancreatitis, Collapsed Lung (Pneumothorax), Complex Regional Pain Syndrome (RSD), Corneal Neuropathic Pain, Crohn's Disease, Degenerative Disc Disease, Dercum's Disease, Dermatomyositis, Diabetic Peripheral Neuropathy (DPN), Dystonia, Ehlers-Danlos Syndrome (EDS), Endometriosis, Eosinophilia-Myalgia Syndrome (EMS), Erythromelalgia, Fibromyalgia, Gout, Headaches, Herniated disc, Hydrocephalus, Intercostal Neuraligia, Interstitial Cystitis, Irritable Bowel syndrome (IBS), Juvenile Dermatositis (Dermatomyositis), Knee Injury, Leg Pain, Loin Pain-Haematuria Syndrome, Lupus, Lyme Disease, Medullary Sponge Kidney (MSK), Meralgia Paresthetica, Mesothelioma, Migraine, Musculoskeletal pain, Myofascial Pain, Myositis, Neck Pain, Neuropathic Pain, Occipital Neuralgia, Osteoarthritis, Paget's Disease, Parsonage Turner Syndrome, Pelvic Pain, Peripheral Neuropathy, Phantom Limb Pain, Pinched Nerve, Polycystic Kidney Disease, Polymyalgia Rhuematica, Polymyositis, *Porphyria*, Post Herniorraphy Pain Syndrome, Post Mastectomy, Pain Syndrome, Post Stroke Pain, Post Thorocotomy Pain Syndrome, Postherpetic Neuralgia (Shingles), Post-Polio Syndrome, Primary Lateral Sclerosis, Psoriatic Arthritis, Pudendal Neuralgia, Radiculopathy, Raynaud's Disease, Rheumatoid Arthritis (RA), Sacroiliac Joint Dysfunction, Sarcoidosi, Scheuemann's Kyphosis Disease, Sciatica, Scoliosis, Shingles (Herpes Zoster), Sjogren's Syndrome, Spasmodic Torticollis, Sphincter of Oddi Dysfunction, Spinal Cerebellum Ataxia (SCA Ataxia), Spinal Cord Injury, Spinal Stenosis, Syringomyelia, Tarlov Cysts, Transverse Myelitis, Trigeminal Neuralgia, Neuropathic Pain, Ulcerative Colitis, Vascular Pain and Vulvodynia.

As used herein, the term "autoimmune disorder", or "inflammatory disorder" means a disease or disorder arising from and/or directed against an individual's own tissues or organs, or a co-segregate or manifestation thereof, or resulting condition therefrom. Typically, various clinical and laboratory markers of autoimmune diseases may exist including, but not limited to, hypergammaglobulinemia, high levels of autoantibodies, antigen-antibody complex deposits in tissues, clinical benefit from corticosteroid or immunosuppressive treatments, and lymphoid cell aggregates in affected tissues. Thus, in one embodiment, the method of present invention is provided to treat an autoimmune disorder, such as chronic inflammation, Multiple Sclerosis, Steven Johnson's Syndrome, appendicitis, bursitis, colitis, cystitis, dermatitis, phlebitis, reflex sympathetic dystrophy/complex regional pain syndrome (rsd/crps), rhinitis, tendonitis, tonsillitis, acne vulgaris, reactive airway disorder, asthma, airway infection, autoinflammatory disease, celiac disease, chronic prostatitis, diverticulitis, glomerulonephritis, hidradenitis suppurativa, hypersensitivities, intestinal disorder, epithelial intestinal disorder, inflammatory bowel disease, irritable bowel syndrome, colitis, interstitial cystitis, otitis, pelvic inflammatory disease, endometrial pain, reperfusion injury, rheumatic fever, rheumatoid arthritis, sarcoidosis, transplant rejection, psoriasis, lung inflammation, chronic obstructive pulmonary disease, cardiovascular disease, and vasculitis.

As used herein, the term "administration" refers to providing a compound, or a pharmaceutical composition comprising the compound as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a MRGPR X4 dependent condition, such as an itch associated condition, a pain associated condition, or an autoimmune disorder. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

In another embodiment, the method of treating a subject having a MRGPR X4 dependent condition (e.g., an itch associated condition, a pain associated condition, an autoimmune condition, or an autoimmune disorder) described herein further comprises administering to the subject a pharmaceutically effective amount of a second therapeutic agent. In one embodiment, the itch associated condition is a liver disease. In one embodiment, the second therapeutic agent is a liver disease therapeutic agent. In one embodiment, the liver disease therapeutic agent is ursodeoxycholic acid (UDCA), norUrsodeoxycholic acid, cholestyramine, stanozolol, naltrexone, rifampicin, Alisol B 23-acetate (AB23A), curcumin, dihydroartemisinin, fenofibrate, bezafibrate, metronidazole, methotrexate, colchicine, metformin, betaine, glucagon, naltrexone, a farnesoid X-receptor (FXR) agonist, a peroxisome proliferator-activated receptor (PPAR) agonist, a thyroid hormone receptor beta (TRβ) agonist, or any combination thereof.

Examples of FXR agonists that may be used in the methods described herein include obeticholic acid, Turofexorate isopropyl (WAY-362450), 3-(2,6-dichlorophenyl)-4-(3'-carboxy-2-chlorostilben-4-yl)oxymethyl-5-isopropylisoxazole (GW4064), PX20606 (PX-102), PX-101, INT-767, INT-787, TERN-101, altenusin, tropifexor (LJN452), nidufexor, turofexorate isopropyl, fexaramine, silymarin, silybin, hedragonic acid, cafestol, Cilofexor (GS-9674 or Px-104), EDP-305, BAR704, BAR502, EYP-001, RDX-023, AGN-242266, HPG-1860, MET-409, AGN-242256, EP-024297, IOT-022, M-480, INV-33, RDX023-02, or any combination thereof. In one embodiment, a FXR agonist is a bile acid or analog thereof (e.g., obeticholic acid, INT-767, INT-787, turofexorate isopropyl (WAY-362450), BAR502, hedragonic acid or BAR704) or a non-bile acid agonist (e.g., EDP-305, tropifexor, nidufexor, cilofexor, GW4064, Turofexorate isopropyl, fexaramine, PX20606 (PX-102), TERN-101, altenusin, silymarin, silybin, hedragonic acid, BAR502, EYP-001, RDX023-2, AGN-242266, HPG-1860, MET-409, EP-024297, M-480, or cafestol). In one embodiment, a PPAR agonist is a PPAR-alpha agonist, a PPAR-gamma agonist, a PPAR-delta agonist, a PPAR-alpha/gamma dual agonist, a PPAR alpha/delta dual agonist, a PPAR gamma/delta dual agonist, or PPAR alpha/gamma/delta pan agonist.

Examples of PPAR alpha agonists that may be used in the methods described herein include fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, and SRI 0171.

Examples of PPAR gamma agonists that may be used in the methods described herein include rosiglitazone, pioglitazone, deuterium-stabilized R-pioglitazone, efatutazone, ATx08-001, OMS-405, CHS-131, THR-0921, SER-150-DN, KDT-501, GED-0507-34-Levo, CLC-3001, and ALL-4.

Examples of PPAR delta agonists that may be used in the methods described herein include GW501516 (endurabol or ({4-[({4-methyl-2-[4-(trifluoromethyl)phenyl]-1,3-thiazol-5-yl}methyl)sulfanyl]-2-methylphenoxy} acetic acid)), MBX8025 (seladelpar or {2-methyl-4-[5-methyl-2-(4-trifluoromethyl-phenyl)-2H-[1,2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy] acetic acid), L165041, HPP-593, and NCP-1046.

Examples of PPAR alpha/gamma agonists that may be used in the methods described herein include saroglitazar, aleglitazar, muraglitazar, tesaglitazar, and DSP-8658.

Examples of PPAR alpha/delta agonists that may be used in the methods described herein include elafibranor and T913659.

Examples of PPAR gamma/delta agonists that may be used in the methods described herein include a conjugated linoleic acid (CLA) and T3D-959.

Examples of PPAR alpha/gamma/delta agonists that may be used in the methods described herein include IVA337 (lanifibranor), TTA (tetradecylthioacetic acid), bavachinin, GW4148, GW9135, bezafibrate, lobeglitazone, 2-(4-(5,6-methylenedioxybenzo[d]thiazol-2-yl)-2-methylphenoxy)-2-methylpropanoic acid (MHY2013), and CS038.

Examples of thyroid hormone receptor beta agonists that may be used in the methods described herein include sobetirome, eprotirome, GC-24, MGL-3196, MGL-3745, VK-2809, KB141 [3,5-dichloro-4-(4-hydroxy-3-isopropylphenoxy) phenylacetic acid], and MB07811 (2R,4S)-4-(3-chlorophenyl)-2-[(3,5-dimethyl-4-(4'-hydroxy-3'-isopropylbenzyl)phenoxy)methyl]-2-oxido-[1,3,2]-dioxaphosphonane).

The second therapeutic agent may be administered simultaneously, separately, or sequentially with the compounds of the present disclosure. If administered simultaneously, the second therapeutic agent and compound of the present disclosure may be administered in separate dosage forms or in the same dosage form.

In another embodiment, a method of treating a subject having an itch associated condition is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the itch associated condition is cholestatic pruritus, uremic pruritus, atopic dermatitis, dry skin, psoriasis, contact dermatitis, or eczema.

In one embodiment of Formula (I), the compound has the structure of Formula (II):

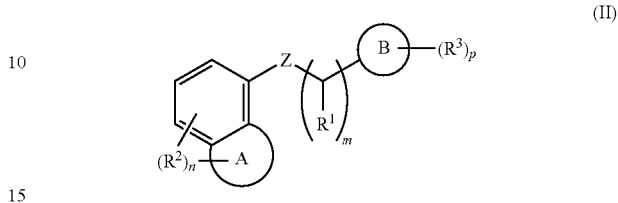

or a pharmaceutically acceptable isomer, racemate, hydrate, solvate, isotope, or salt thereof, wherein m, n, p, A, B, Z, $R^1$, $R^2$ and $R^3$ are as defined above.

In one embodiment of Formula (I), A is 5- or 6-membered carbocycle.

In yet another embodiment of Formula (I), A is 5- or 6-membered heteroocycle.

In one embodiment of Formula (I), A is 5-membered heterocycle and the compound has the structure of Formula (III):

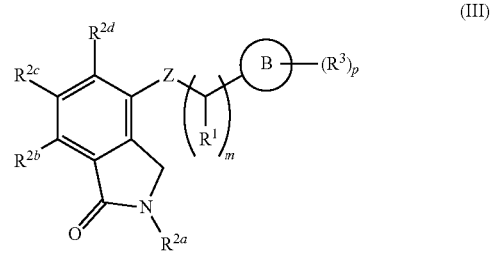

or a pharmaceutically acceptable isomer, racemate, hydrate, solvate, isotope, or salt thereof, wherein m, p, B, Z, $R^1$ and $R^3$ are as defined above and wherein:

$R^{2a}$, $R^{2b}$, and $R^{2d}$ are each, independently, H, halo, alkyl, haloalkyl, or aralkyl.

In one embodiment of Formula (I), A is 6-membered heterocycle and the compound has the structure of Formula (IV):

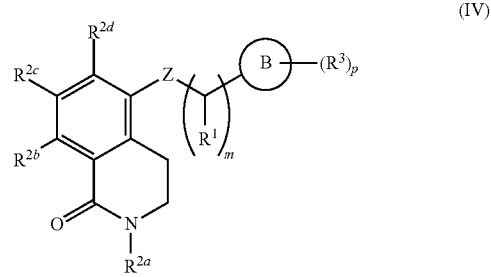

or a pharmaceutically acceptable isomer, racemate, hydrate, solvate, isotope, or salt thereof, wherein m, p, B, Z, $R^{2a}$, $R^{2b}$, $R^{2c}$, $R^{2d}$ and $R^3$ are as defined above.

In one embodiment of Formula (I), B is a heterocycle.

In one embodiment of Formula (I), B is pyridine, pyrimidine, pyrazole, furan, oxazole, isoxazole, oxadiazole, thiophene, thiazole, thiadiazole, tetrahydro-2H-pyran, benzoxadiazole, benzothiazole, benzotriazole, or 2,3-dihydrobenzo[b][1,4]dioxine.

In another embodiment of Formula (I), B is a carbocycle.

In another embodiment of Formula (I), B is cyclopropyl, cyclobutyl, cyclopentyl, cyclohexyl, phenyl, naphthalene, or tetrahydronaphthalene.

In another embodiment of Formula (I), B is phenyl.

In one embodiment of Formula (I), A is 5-membered heterocycle, B is phenyl and the compound has the structure of Formula (V):

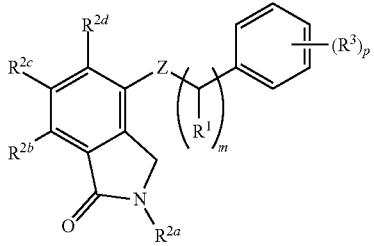

(V)

or a pharmaceutically acceptable isomer, racemate, hydrate, solvate, isotope, or salt thereof, wherein m, p, B, Z, $R^1$, $R^{2a}$, $R^{2b}$, $R^{2c}$, $R^{2d}$ and $R^3$ are as defined above.

In one embodiment of Formula (1), A is 6-membered heterocycle, B is phenyl and the compound has the structure of Formula (VI):

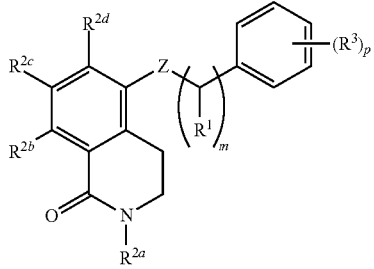

(VI)

or a pharmaceutically acceptable isomer, racemate, hydrate, solvate, isotope, or salt thereof, wherein m, p, B, Z, $R^1$, $R^{2a}$, $R^{2b}$, $R^{2c}$, $R^{2d}$ and $R^3$ are as defined above.

In one embodiment of Formula (I), Z is —O—.

In one embodiment of Formula (I), m is 1, $R^1$ is H, A is 5-membered heterocycle, B is phenyl, Z is —O— and the compound has the structure of Formula (VII):

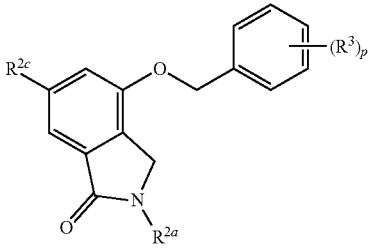

(VII)

or a pharmaceutically acceptable isomer, racemate, hydrate, solvate, isotope, or salt thereof, wherein p, $R^{2a}$, $R^{2c}$ and $R^3$ are as defined above.

In one embodiment of Formula (I), m is 1, $R^1$ is H, A is 6-membered heterocycle, B is phenyl, Z is —O— and the compound has the structure of Formula (VIII):

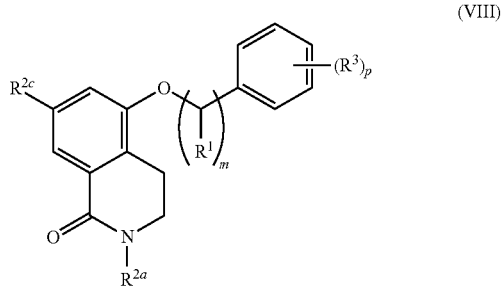

(VIII)

or a pharmaceutically acceptable isomer, racemate, hydrate, solvate, isotope, or salt thereof, wherein p, $R^{2a}$, $R^{2c}$ and $R^3$ are as defined above.

In one embodiment of Formula (I), Z is —N(R')—.

In one embodiment of Formula (I), m is 1, $R^1$ is H, A is 6-membered heterocycle, B is phenyl, Z is —N(R')— where R' is H, and the compound has the structure of Formula (IX):

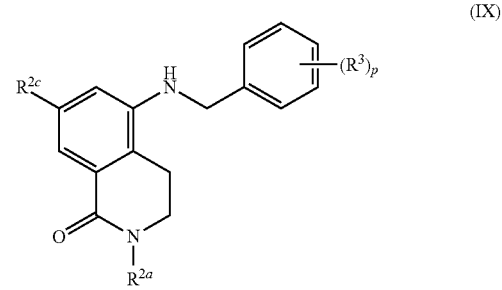

(IX)

or a pharmaceutically acceptable isomer, racemate, hydrate, solvate, isotope, or salt thereof, wherein p, $R^{2a}$, $R^{2C}$ and $R^3$ are as defined above.

In one embodiment of Formula (I), Z is —N(R')SO$_2$—.

In one embodiment of Formula (I), m is 1, $R^1$ is H, A is 6-membered heterocycle, B is phenyl, Z is —N(R)SO$_2$— where R' is H, and the compound has the structure of Formula (X):

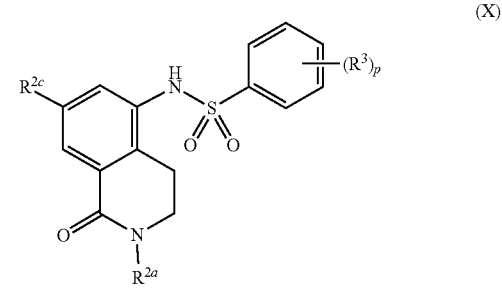

(X)

or a pharmaceutically acceptable isomer, racemate, hydrate, solvate, isotope, or salt thereof, wherein p, $R^{2c}$, $R^{2C}$ and $R^3$ are as defined above.

In one embodiment of Formula (I), Z is —N(R')C(O)—.

In one embodiment of Formula (I), m is 1, R¹ is H, A is 6-membered heterocycle, B is phenyl, Z is —N(R)C(O)— where R' is H, and the compound has the structure of Formula (XI):

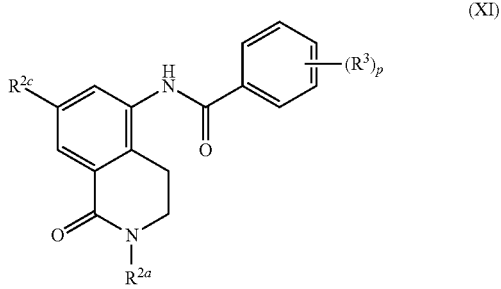

(XI)

or a pharmaceutically acceptable isomer, racemate, hydrate, solvate, isotope, or salt thereof, wherein p, $R^{2a}$, $R^{2c}$ and $R^3$ are as defined above.

In one embodiment of Formula (I), Z is —SO₂N(R')—.

In one embodiment of Formula (I), m is 1, R¹ is H, A is 6-membered heterocycle, B is phenyl, Z is —SO₂N(R')— where R' is H, and the compound has the structure of Formula (XII):

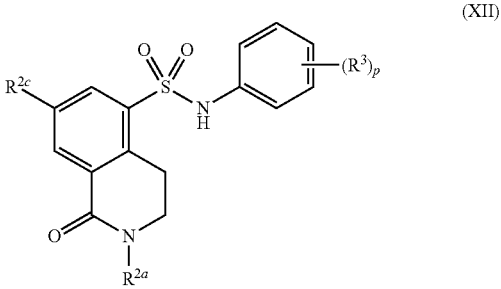

(XII)

or a pharmaceutically acceptable isomer, racemate, hydrate, solvate, isotope, or salt thereof, wherein p, $R^{2a}$, $R^{2c}$ and $R^3$ are as defined above.

In one embodiment of Formula (I), Z is —C(O)N(R')—.

In one embodiment of Formula (I), m is 1, R¹ is H, A is 6-membered heterocycle, B is phenyl, Z is —C(O)N(R')— where R' is H, and the compound has the structure of Formula (XIII):

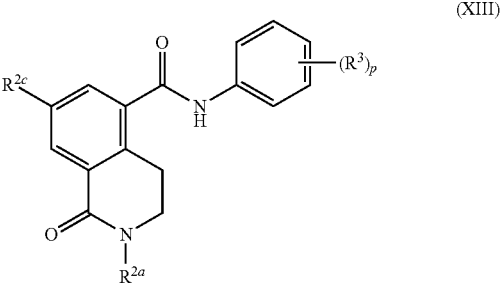

(XIII)

or a pharmaceutically acceptable isomer, racemate, hydrate, solvate, isotope, or salt thereof, wherein p, $R^{2a}$, $R^{2c}$ and $R^3$ are as defined above.

Representative compounds of Formula (I), as well as Formulas (II) through (XIII) as applicable, include any one of the compounds listed in Table A below, as well as a pharmaceutically acceptable isomer, racemate, hydrate, solvate, isotope, or salt thereof. To this end, representative compounds are identified herein by their respective "Compound Number", which is sometimes abbreviated as "Compound No." or "Cpd. No."

TABLE A

Representative Compounds

| Cpd. No. | Structure |
|---|---|
| 1-1 | ![structure] |
| 1-2 | ![structure] |
| 1-3 | ![structure] |
| 1-4 | ![structure] |
| 1-5 | ![structure] |

TABLE A-continued

Representative Compounds

| Cpd. No. | Structure |
|---|---|
| 1-6 | 5-[(4-chlorobenzyl)oxy]-2-methyl-3,4-dihydroisoquinolin-1(2H)-one |
| 1-7 | 5-[(4-chlorobenzyl)oxy]-2-ethyl-3,4-dihydroisoquinolin-1(2H)-one |
| 1-8 | 2-benzyl-5-(benzyloxy)-3,4-dihydroisoquinolin-1(2H)-one |
| 2-1 | 5-{[2-chloro-4-(trifluoromethyl)benzyl]oxy}-2-methyl-3,4-dihydroisoquinolin-1(2H)-one |
| 2-2 | 5-[(4-fluorobenzyl)oxy]-2-methyl-3,4-dihydroisoquinolin-1(2H)-one |
| 2-3 | 2-methyl-5-[(4-methylbenzyl)oxy]-3,4-dihydroisoquinolin-1(2H)-one |
| 2-4 | 2-methyl-5-{[4-(trifluoromethyl)benzyl]oxy}-3,4-dihydroisoquinolin-1(2H)-one |
| 2-5 | 2-methyl-5-{[4-(trifluoromethoxy)benzyl]oxy}-3,4-dihydroisoquinolin-1(2H)-one |
| 2-6 | 5-{[4-(difluoromethoxy)benzyl]oxy}-2-methyl-3,4-dihydroisoquinolin-1(2H)-one |
| 2-7 | 4-{[(2-methyl-1-oxo-1,2,3,4-tetrahydroisoquinolin-5-yl)oxy]methyl}benzonitrile |

TABLE A-continued

Representative Compounds

| Cpd. No. | Structure |
|---|---|
| 2-8 | 5-[(2,4-dichlorobenzyl)oxy]-2-methyl-3,4-dihydroisoquinolin-1(2H)-one |
| 2-9 | 5-[(4-chloro-2-methylbenzyl)oxy]-2-methyl-3,4-dihydroisoquinolin-1(2H)-one |
| 2-10 | 5-[(2,4-dimethylbenzyl)oxy]-2-methyl-3,4-dihydroisoquinolin-1(2H)-one |
| 2-11 | 5-[(3,5-dichlorobenzyl)oxy]-2-methyl-3,4-dihydroisoquinolin-1(2H)-one |
| 2-12 | 5-[(2-chloro-4-methylbenzyl)oxy]-2-methyl-3,4-dihydroisoquinolin-1(2H)-one |
| 2-13 | 5-[(3,4-dimethylbenzyl)oxy]-2-methyl-3,4-dihydroisoquinolin-1(2H)-one |
| 2-14 | 5-[(3,4-dichlorobenzyl)oxy]-2-methyl-3,4-dihydroisoquinolin-1(2H)-one |
| 2-15 | 5-[(2,4-dichloro-5-fluorobenzyl)oxy]-2-methyl-3,4-dihydroisoquinolin-1(2H)-one |
| 2-16 | 5-[(2-fluoro-4-methylbenzyl)oxy]-2-methyl-3,4-dihydroisoquinolin-1(2H)-one |
| 2-17 | 5-[(4-chloro-2-fluorobenzyl)oxy]-2-methyl-3,4-dihydroisoquinolin-1(2H)-one |

TABLE A-continued

Representative Compounds

| Cpd. No. | Structure |
|---|---|
| 2-18 | (structure) |
| 2-19 | (structure) |
| 2-20 | (structure) |
| 2-21 | (structure) |
| 2-22 | (structure) |
| 2-23 | (structure) |
| 2-24 | (structure) |
| 2-25 | (structure) |
| 2-26 | (structure) |
| 2-27 | (structure) |

TABLE A-continued

Representative Compounds

| Cpd. No. | Structure |
|---|---|
| 2-28 | (2-fluoro-5-trifluoromethylbenzyloxy) substituted N-methyl-3,4-dihydroisoquinolin-1(2H)-one |
| 2-29 | (4-chloro-2-fluoro-5-fluorobenzyloxy) substituted N-methyl-3,4-dihydroisoquinolin-1(2H)-one |
| 2-30 | (4-cyano-3-fluorobenzyloxy) substituted N-methyl-3,4-dihydroisoquinolin-1(2H)-one |
| 2-31 | (4-chloro-2-trifluoromethylbenzyloxy) substituted N-methyl-3,4-dihydroisoquinolin-1(2H)-one |
| 2-32 | (4-trifluoromethyl-2-methoxybenzyloxy) substituted N-methyl-3,4-dihydroisoquinolin-1(2H)-one |
| 2-33 | (2-methoxy-5-chlorobenzyloxy) substituted N-methyl-3,4-dihydroisoquinolin-1(2H)-one |
| 2-34 | (2,3-dimethoxybenzyloxy) substituted N-methyl-3,4-dihydroisoquinolin-1(2H)-one |
| 2-35 | (2,5-dimethoxybenzyloxy) substituted N-methyl-3,4-dihydroisoquinolin-1(2H)-one |
| 2-36 | (4-chloro-3-trifluoromethylbenzyloxy) substituted N-methyl-3,4-dihydroisoquinolin-1(2H)-one |
| 2-37 | (2-fluoro-4-methyl-5-chlorobenzyloxy) substituted N-methyl-3,4-dihydroisoquinolin-1(2H)-one |

TABLE A-continued
Representative Compounds
| Cpd. No. | Structure |
|---|---|
| 2-38 | 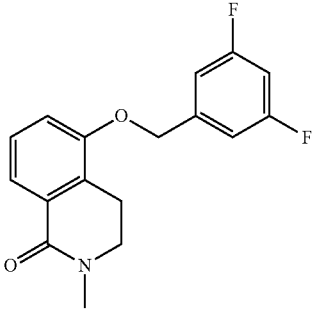 [SMILES: CN1CCc2c(OCc3cc(F)cc(F)c3)cccc2C1=O] |
| 2-39 | 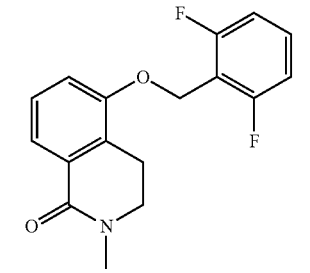 [SMILES: CN1CCc2c(OCc3c(F)cccc3F)cccc2C1=O] |
| 2-40 | 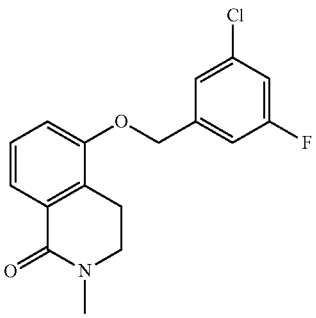 |
| 2-41 | 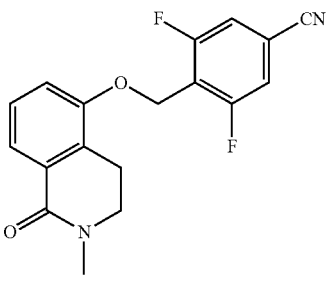 [SMILES: CN1CCc2c(OCc3c(F)cc(C#N)cc3F)cccc2C1=O] |
| 2-42 | 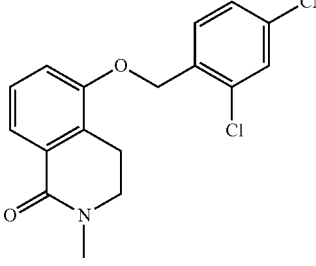 |
TABLE A-continued
Representative Compounds
| Cpd. No. | Structure |
|---|---|
| 2-43 | 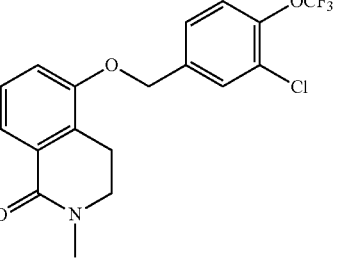 |
| 2-44 | 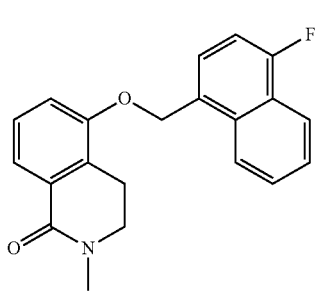 [SMILES: CN1CCc2c(OCc3ccc(F)c4ccccc34)cccc2C1=O] |
| 2-45 | 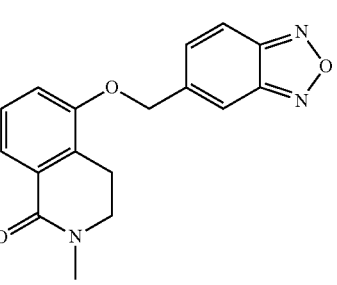 |
| 2-46 | 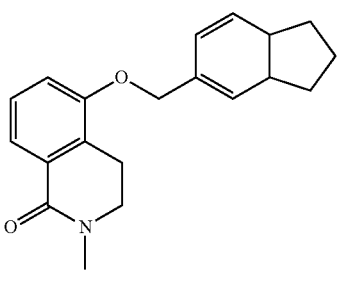 [SMILES: CN1CCc2c(OCC3=CC4CCCC4C=C3)cccc2C1=O] |
| 3-1 | 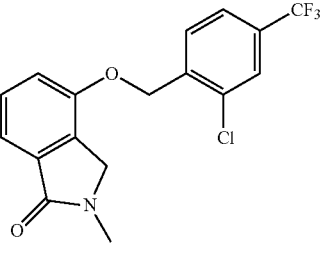 [SMILES: CN1Cc2c(OCc3ccc(C(F)(F)F)cc3Cl)cccc2C1=O] |

TABLE A-continued
Representative Compounds
| Cpd. No. | Structure |
|---|---|
| 3-2 | 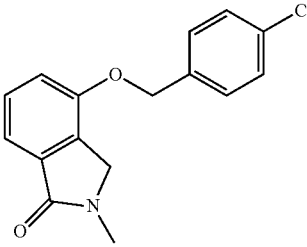 [SMILES: CN1Cc2c(OCc3ccc(F)cc3)cccc2C1=O] |
| 4-1 | 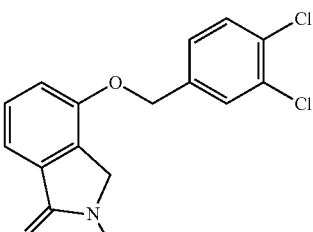 |
| 4-2 | 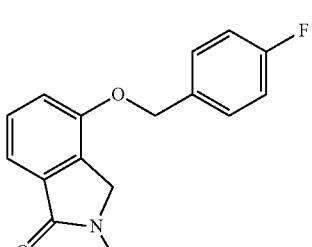 |
| 4-3 | 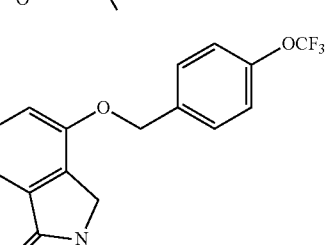 |
| 4-4 | 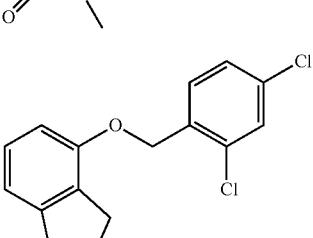 |
| 4-5 | 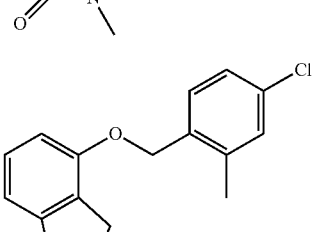 |
| 4-6 | 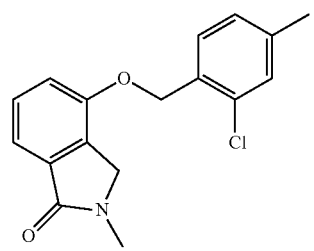 [SMILES: Cc1ccc(COc2cccc3c2CN(C)C3=O)c(Cl)c1] |
| 4-7 | 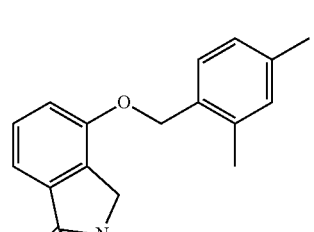 |
| 5-1 | 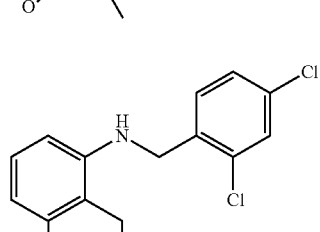 |
| 5-2 | 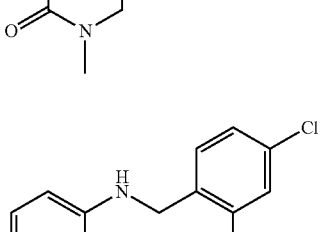 |
| 5-3 | 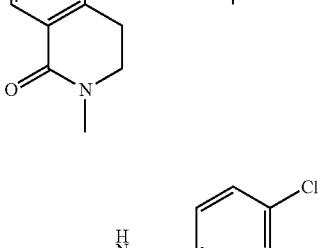 |

TABLE A-continued

Representative Compounds

| Cpd. No. | Structure |
|---|---|
| 5-4 | 5-chloro-N-(methyl)-... 1-methyl-5-[(2-chloro-4-trifluoromethylbenzyl)amino]-3,4-dihydroisoquinolin-1(2H)-one |
| 6-1 | 5-[(2-chloro-4-trifluoromethylphenoxy)methyl]-3,4-dihydroisoquinolin-1(2H)-one |
| 6-2 | 5-[(2-chloro-4-trifluoromethylphenoxy)methyl]-2-methyl-3,4-dihydroisoquinolin-1(2H)-one |
| 7-1 | 7-fluoro-5-[(4-chlorobenzyl)oxy]-2-methyl-3,4-dihydroisoquinolin-1(2H)-one |
| 7-2 | 7-fluoro-5-[(2-chloro-4-trifluoromethylbenzyl)oxy]-2-methyl-3,4-dihydroisoquinolin-1(2H)-one |
| 8-1 | 7-methyl-5-[(4-chlorobenzyl)oxy]-2-methyl-3,4-dihydroisoquinolin-1(2H)-one |
| 8-2 | 7-methyl-5-[(2-chloro-4-trifluoromethylbenzyl)oxy]-2-methyl-3,4-dihydroisoquinolin-1(2H)-one |

In other embodiments, prodrugs and/or metabolites of compounds of Formula (I), as well as Formulas (II) through (XIII), are provided.

Thus, in one embodiment, prodrugs of a compound of the invention are provided, which upon administration to a subject, undergo chemical conversion by metabolic or other physiological processes to become active pharmacological substances. Conversion by metabolic or other physiological processes includes, without limitation, enzymatic (e.g., specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

Accordingly, a "prodrug" is a substance that, upon administration to a subject, is converted in vivo by the action of biochemicals within the subject's body, such as enzymes, to an active pharmaceutical ingredient. Examples of prodrugs include esters of carboxylic acid groups, which can be hydrolyzed by endogenous esterases as are found in the bloodstream of humans and other mammals. In one embodiment, substances are provided that can be administered to a subject which are then converted within the subject's body to provide a compound having the structure of Formula (I), or any of Formulas (II) through (XIII).

As used herein, a "metabolite" is a compound that, following administration to a subject, is converted within the body of the subject to yield an active substance. Such conversion often involves hydrolysis, phosphorylation and/ or oxidation/reduction processes, and may be mediated by any number of enzymes (e.g., esterases, phosphatases, cytochrome P450, and the like), as well by different environments within the body (e.g., changes in pH).

In certain embodiments, the invention provides a pharmaceutical composition comprising a compound of any one of Formulas (I) through (XIV) together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in Remington: The Science and Practice of Pharmacy, 21st Ed., Gennaro, Ed., Lippencott Williams & Wilkins (2005) and in The United States Pharmacopeia: The National Formulary (USP 36 NF31), published in 2013.

In some embodiments, the pharmaceutical composition comprising a compound of any one of Formulas (I) through (XIII) with at least one pharmaceutically acceptable carrier, diluent, or excipient further comprises a second therapeutic agent. In one embodiment, the second therapeutic agent is a liver disease therapeutic agent. In one embodiment, the liver disease therapeutic agent is ursodeoxycholic acid (UDCA), norUrsodeoxycholic acid, cholestyramine, stanozolol, naltrexone, rifampicin, Alisol B 23-acetate (AB23A), curcumin, dihydroartemisinin, fenofibrate, bezafibrate, metronidazole, methotrexate, colchicine, metformin, betaine, glucagon, naltrexone, a farnesoid X-receptor (FXR) agonist, a peroxisome proliferator-activated receptor (PPAR) agonist, a thyroid hormone receptor beta (TRβ) agonist, or any combination thereof.

Examples of FXR agonists that may be used in the pharmaceutical compositions described herein include obeticholic acid, Turofexorate isopropyl (WAY-362450), 3-(2,6-dichlorophenyl)-4-(3'-carboxy-2-chlorostilben-4-yl)oxym- ethyl-5-isopropylisoxazole (GW4064), PX20606 (PX-102), PX-101, INT-767, INT-787, TERN-101, altenusin, tropifexor (LJN452), nidufexor, turofexorate isopropyl, fexaramine, silymarin, silybin, hedragonic acid, cafestol, Cilofexor (GS-9674 or Px-104), EDP-305, BAR704, BAR502, EYP-001, RDX-023, AGN-242266, HPG-1860, MET-409, AGN-242256, EP-024297, IOT-022, M-480, INV-33, RDX023-02, or any combination thereof. In one embodiment, a FXR agonist is a bile acid or analog thereof (e.g., obeticholic acid, INT-767, INT-787, turofexorate isopropyl (WAY-362450), BAR502, hedragonic acid or BAR704) or a non-bile acid agonist (e.g., EDP-305, tropifexor, nidufexor, cilofexor, GW4064, Turofexorate isopropyl, fexaramine, PX20606 (PX-102), TERN-101, altenusin, silymarin, silybin, hedragonic acid, BAR502, EYP-001, RDX023-2, AGN-242266, HPG-1860, MET-409, EP-024297, M-480, or cafestol). In one embodiment, a PPAR agonist is a PPAR-alpha agonist, a PPAR-gamma agonist, a PPAR-delta agonist, a PPAR-alpha/gamma dual agonist, a PPAR alpha/delta dual agonist, a PPAR gamma/delta dual agonist, a PPAR alpha/gamma/delta pan agonist, or any combination thereof.

Examples of PPAR alpha agonists that may be used in the pharmaceutical compositions described herein include fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, and SRI 0171.

Examples of PPAR gamma agonists that may be used in the pharmaceutical compositions described herein include rosiglitazone, pioglitazone, deuterium-stabilized R-pioglitazone, efatutazone, ATx08-001, OMS-405, CHS-131, THR-0921, SER-150-DN, KDT-501, GED-0507-34-Levo, CLC-3001, and ALL-4.

Examples of PPAR delta agonists that may be used in the pharmaceutical compositions described herein include GW501516 (endurabol or ({4-[({4-methyl-2-[4-(trifluoromethyl)phenyl]-1,3-thiazol-5-yl}methyl)sulfanyl]-2-methylphenoxy} acetic acid)), MBX8025 (seladelpar or {2-methyl-4-[5-methyl-2-(4-trifluoromethyl-phenyl)-2H-[1,2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy] acetic acid), L165041, HPP-593, and NCP-1046.

Examples of PPAR alpha/gamma agonists that may be used in the pharmaceutical compositions described herein include saroglitazar, aleglitazar, muraglitazar, tesaglitazar, and DSP-8658.

Examples of PPAR alpha/delta agonists that may be used in the pharmaceutical compositions described herein include elafibranor and T913659.

Examples of PPAR gamma/delta agonists that may be used in the pharmaceutical compositions described herein include a conjugated linoleic acid (CLA) and T3D-959.

Examples of PPAR alpha/gamma/delta agonists that may be used in the pharmaceutical compositions described herein include IVA337 (lanifibranor), TTA (tetradecylthioacetic acid), bavachinin, GW4148, GW9135, bezafibrate, lobeglitazone, 2-(4-(5,6-methylenedioxybenzo[d]thiazol-2-yl)-2-methylphenoxy)-2-methylpropanoic acid (MHY2013), and CS038.

Examples of thyroid hormone receptor beta agonists that may be used in the pharmaceutical compositions described herein include sobetirome, eprotirome, GC-24, MGL-3196, MGL-3745, VK-2809, KB141 [3,5-dichloro-4-(4-hydroxy-3-isopropylphenoxy) phenyl acetic acid], and MB07811

(2R,4S)-4-(3-chlorophenyl)-2-[(3,5-dimethyl-4-(4'-hydroxy-3'-isopropylbenzyl)phenoxy)methyl]-2-oxido-[1,3,2]-dioxaphosphonane).

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral. In another embodiment, the route of administration is topical.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the Physicians' Desk Reference, incorporated herein by reference.

In one embodiment, the invention provides an oral pharmaceutical composition comprising a compound of any one of Formulas (I) through (XIII) together with at least one pharmaceutically acceptable oral carrier, diluent, or excipient. In another embodiment, the invention provides a topical pharmaceutical composition comprising a compound of any one of Formulas (I) through (XIII) together with at least one pharmaceutically acceptable topical carrier, diluent, or excipient. For example, the oral pharmaceutical composition is provided to treat cholestatic pruritus, wherein the dosage regimen is, for example, once a day. In one embodiment, the topical pharmaceutical composition is provided to treat atopic dermatitis.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In certain embodiments, the invention provides a compound having the structure of any one of Formulas (I) through (XIII). Such compounds can be synthesized using standard synthetic techniques known to those skilled in the art. For example, compounds of the present invention can be synthesized using appropriately modified synthetic procedures set forth in the following Examples and Reaction Schemes.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

All reagents, for which the synthesis is not described in the experimental part, are either commercially available, or are known compounds or may be formed from known compounds by known methods by a person skilled in the art. The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by preparative HPLC using methods as described.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present invention as isolated and as described herein is not necessarily the only form in which said compound can be applied to a biological assay in order to quantify the specific biological activity.

Chemical names were generated using the ChemDraw naming software (Version 17.0.0.206) by PerkinElmer Informatics, Inc. In some cases, generally accepted names of commercially available reagents were used in place of names generated by the naming software.

EXAMPLES

General Methods $^1$H NMR (400 MHz) spectra were obtained in solution of deuteriochloroform (CDCl$_3$), deuteriomethanol (CD$_3$OD) or dimethyl sulfoxide—D6 (DMSO). HPLC retention times, purities and mass spectra (LCMS) were obtained using one of the following methods:

Method 1: Agilent 1260 Infinity II System equipped with an Agilent Poroshell 120 EC-18, 2.7 μm, 4.6×100 mm column, using H$_2$O with 0.1% formic acid as the mobile phase A, and MeCN with 0.1% formic acid as the mobile phase B. An ESI detector in positive mode was used. The gradient was 20-95% mobile phase B over 5 min then held at 95% for 3.8 mins, then return to 20% mobile phase B over 0.2 min. The flow rate was 1 mL/min.

Method 2: Agilent 1260 Infinity II System equipped with an Agilent Poroshell 120 EC-18, 2.7 μm, 4.6×100 mm column, using H$_2$O with 0.1% formic acid as the mobile phase A, and MeCN with 0.1% formic acid as the mobile phase B. An ESI detector in positive mode was used. The gradient was 10-95% mobile phase B over 12 min then held at 95% for 2 min, then return to 10% mobile phase B over 1 min. The flow rate was 1 mL/min.

Method 3: Shimadzu SCL-10A system equipped with Agilent Eclipse XDB-C18, 3.5 μm, 4.6×150 mm column and PE Sciex API 150 EX, using H$_2$O with 0.1% trifluoroacetic acid as the mobile phase A, and methanol with 0.1% trifluoroacetic acid as the mobile phase B. The gradient was 5-95% mobile phase B over 12 min then held at 95% mobile phase B for 3 min, then return to 5% mobile phase B for 1 min. The flow rate was 1 mL/min.

Method 4: Waters Acquity system equipped with an Acquity UPLC BEH C18 1.7 μm, 2.1×50 mm column, using H$_2$O with 0.1% ammonium formate adjusted to pH 3.8 with formic acid as the mobile phase A, and acetonitrile as the mobile phase B. The gradient was 5-100% over 9 minutes then held at 100% mobile phase B for 1 minute. The flow rate was 0.7 mL/min.

Method 5: Waters Acquity system equipped with an EVO C18 (5 μm, 3.0×50 mm) using a low pH buffer gradient of 5% to 100% of MeCN in H$_2$O (0.1% HCOOH) over 2.5 min at 2.2 mL/min, and holding at 100% for a total time of 3.5 min.

The pyridine, dichloromethane (DCM), tetrahydrofuran (THF), and toluene used in the procedures were from Aldrich Sure-Seal bottles kept under nitrogen (N$_2$). All reactions were stirred magnetically, and temperatures are external reaction temperatures. Chromatographies were typically carried out using a Combiflash Rf flash purification system (Teledyne Isco) equipped with Redisep (Teledyne Isco) Rf Gold Normal-Phase silica gel (SiO$_2$) columns or by using a similar system.

Preparative HPLC purifications were typically performed using one of the following systems: 1) Waters System equipped with a Waters 2489 uv/vis detector, an Aquity QDA detector, a Waters xBridge Prep C18 5 μm OBD, 30×150 mm column, and eluting with various gradients of H$_2$O/MeCN (0.1% formic acid) at a 30 mL/min flow rate, 2) Teledyne Isco ACCQPrep® HP150 UV system equipped with a Waters xBridge Prep C18 5 μm OBD, 30×150 mm column, and eluting with various gradients of H$_2$O/MeCN (0.1% formic acid) at a 42.5 mL/min flow rate, or 3) column: Phenomenex Synergi C18 150×30 mm–4 μm; mobile phase: [H$_2$O (0.225% formic acid)-MeCN]; B %: 55%-85%, 12 min) and were typically concentrated using a Genevac EZ-2.

The following additional abbreviations are used: ethyl acetate (EA), triethylamine (TEA), dimethyl sulfoxide (DMSO), silica gel (SiO$_2$), azobisisobutyronitrile (AIBN), diisobutylaluminium hydride (DIBAL), trifluoroacetic acid (TFA), 4-dimethylaminopyridine (DMAP), diphenylphosphoryl azide (DPPA), benzoyl peroxide (BPO), 1,1'-bis(diphenylphosphino)ferrocene (dppf), bis(pinacolato)diboron (B$_2$pin$_2$), tetrahydrofuran (THF), 1,4-diazabicyclo[2.2.2]octane bis(sulfur dioxide) adduct (DABSO), hexafluorophosphate azabenzotriazole tetramethyl uronium (HATU), hydroxybenzotriazole (HOBt), N-methyl morpholine (NMM), N-Bromosuccinimide (NBS), diisopropylethyl amine (DIPEA), diethyl azodicarboxylate (DEAD), diisopropyl azodicarboxylate (DIAD), 2-[2-(dicyclohexylphosphino)phenyl]-N-methylindole (CM-Phos), triflic acid (TfOH), 1-ethyl-3-(3-dimethylaminopropyl) carbodiimide hydrochloride (EDC), isopropanol (IPA), dimethylformamide (DMF), dimethyl acetamide (DMA), dichloromethane (DCM), 1,2-dichloroethane (DCE), acetonitrile (MeCN or ACN), 1,1'-thiocarbonyldiimidazole (TCDI), petroleum ether (PE), not determined (ND), retention time (RT), molecular weight (mw), room temperature (rt), hour (h), and not applicable (N/A).

Example 1

Synthesis of Compound 1-1, Compound 1-5 and Other Representative Compounds

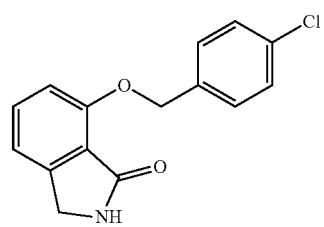

1-1

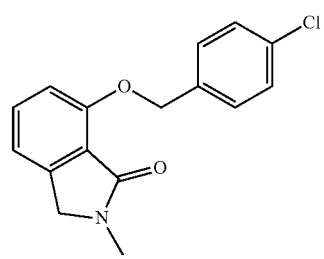

1-5

Scheme 1

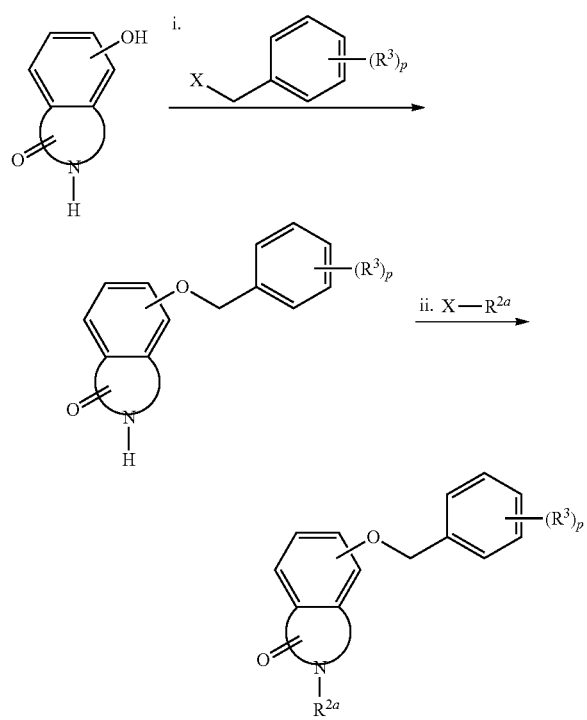

Reagents: (i)K₂CO₃, solvent (MeCN or DMF); ii. NaH or KO'Bu, solvent (THF or DMF)

Step 1-1. Synthesis of 7-((4-chlorobenzyl)oxy) isoindolin-1-one (Compound 1-1)

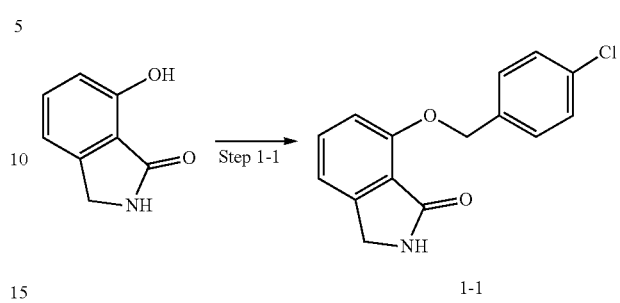

To a stirring solution of 4-chlorobenzyl chloride (108 mg, 1.0 equiv., 670 µmol) and 7-hydroxyisoindolin-1-one (100 mg, 1.0 equiv., 670 µmol) in DMF (4 mL) was charged $K_2CO_3$ (120 mg, 1.3 equiv., 872 µmol). The resulting yellow suspension was heated and stirred at 80° C. for 14 hours. The reaction mixture was cooled to room temperature and filtered. The filtrate was purified by prep HPLC to yield 63.4 mg (34.5%) of 7-((4-chlorobenzyl)oxy)isoindolin-1-one (Compound 1-1) as white needles. LCMS-ESI (m/z) calculated for $C_{15}H_{12}ClNO_2$: 273.06; found 274.1 [M+H]⁺, $t_R$=7.86 min (Method 2). ¹H NMR (400 MHz, DMSO-d₆) δ 8.26 (s, 1H), 7.56-7.43 (m, 5H), 7.10 (d, J=7.6 Hz, 1H), 7.04 (d, J=8.3 Hz, 1H), 5.24 (s, 2H), 4.29 (s, 2H).

The compounds listed in Table 1A were made using the procedures of Scheme 1.

TABLE 1A

| Structure | Cpd No. | Purity RT (min) | MW | Observed m/z | Ion | Purity Method |
|---|---|---|---|---|---|---|
| 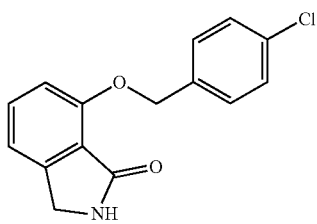 [SMILES: O=C1NCc2cccc(OCc3ccc(Cl)cc3)c21] | 1-1 | 7.86 | 273.06 | 274.1 | [M + H]⁺ | 2 |
| 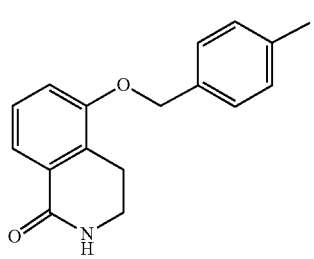 [SMILES: Cc1ccc(COc2cccc3c2CCNC3=O)cc1] | 1-2 | 8.40 | 267.33 | 268.1 | [M + H]⁺ | 2 |

TABLE 1A-continued

| Structure | Cpd No. | Purity RT (min) | MW | Observed m/z | Ion | Purity Method |
|---|---|---|---|---|---|---|
| (3,4-dihydroquinolin-2(1H)-one with 5-((4-chlorobenzyl)oxy) substituent) | 1-3 | 9.32 | 287.74 | 287.9 | [M + H]⁺ | 2 |
| (indolin-2-one with 4-((4-chlorobenzyl)oxy) substituent) | 1-4 | 8.97 | 273.72 | 274.1 | [M + H]⁺ | 2 |

Step 1-2. Synthesis of 7-((4-chlorobenzyl)oxy)-2-methylisoindolin-1-one (Compound 1-5)

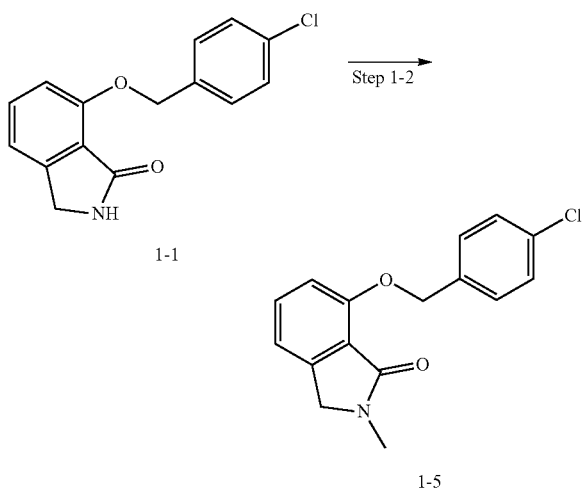

To a stirring solution of Compound 1-1 (57.7 mg, 1.0 equiv., 211 μmol) in DMF (2 mL) was charged with NaH (60% dispersion in mineral oil, 8.4 mg, 1.0 equiv., 211 μmol) in one portion. The suspension was stirred at room temperature for 15 minutes, and was subsequently charged with iodomethane (29.9 mg, 13.1 μL, 1.0 equiv., 211 μmol). The resulting mixture was stirred at room temperature for 14 hours. The reaction mixture was filtered, and the filtrate was purified by prep HPLC to yield 23.3 mg (38.4%) of 7-((4-chlorobenzyl)oxy)-2-methylisoindolin-1-one (Compound 1-5) as a white solid. LCMS-ESI (m/z) calculated for C₁₆H₁₄ClNO₂: 287.07; found 288.1 [M+H]⁺, $t_R$=8.66 min (Method 2). ¹H NMR (400 MHz, DMSO-d₆) δ 7.57-7.43 (m, 5H), 7.11 (d, J=7.4 Hz, 1H), 7.05 (d, J=8.2 Hz, 1H), 5.25 (s, 2H), 4.38 (s, 2H), 3.01 (s, 3H).

The compounds listed in Table 1B were made using the procedures of Scheme 1.

TABLE 1B

| Structure | Cpd No. | Purity RT (min) | MW | Observed m/z | Ion | Purity Method |
|---|---|---|---|---|---|---|
| (7-((4-chlorobenzyl)oxy)-2-methylisoindolin-1-one) | 1-5 | 8.66 | 287.07 | 288.1 | [M + H]⁺ | 2 |

TABLE 1B-continued
| Structure | Cpd No. | Purity RT (min) | MW | Observed m/z | Ion | Purity Method |
|---|---|---|---|---|---|---|
| 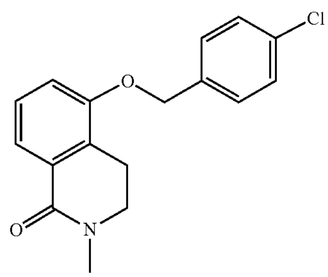 [SMILES: CN1CCc2c(OCc3ccc(Cl)cc3)cccc2C1=O] | 1-6 | 9.66 | 301.77 | 302.2 | [M + H]+ | 2 |
| 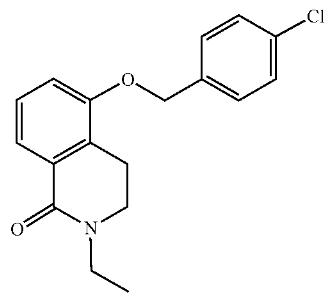 [SMILES: CCN1CCc2c(OCc3ccc(Cl)cc3)cccc2C1=O] | 1-7 | 10.29 | 315.80 | 316.1 | [M + H]+ | 2 |
| 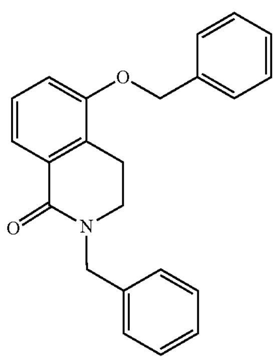 [SMILES: O=C1c2cccc(OCc3ccccc3)c2CCN1Cc1ccccc1] | 1-8 | 10.97 | 343.43 | 344.2 | [M + H]+ | 2 |
Example 2
Synthesis of Compound 2-1 and Other Representative Compounds
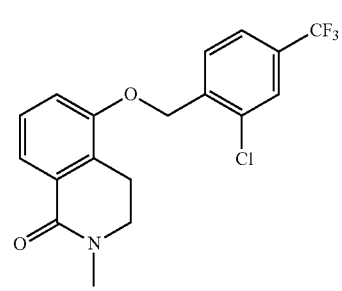
2-1
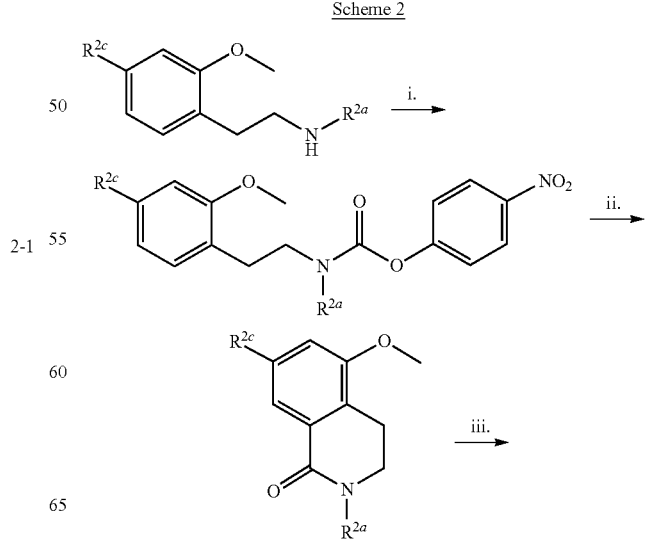
Scheme 2

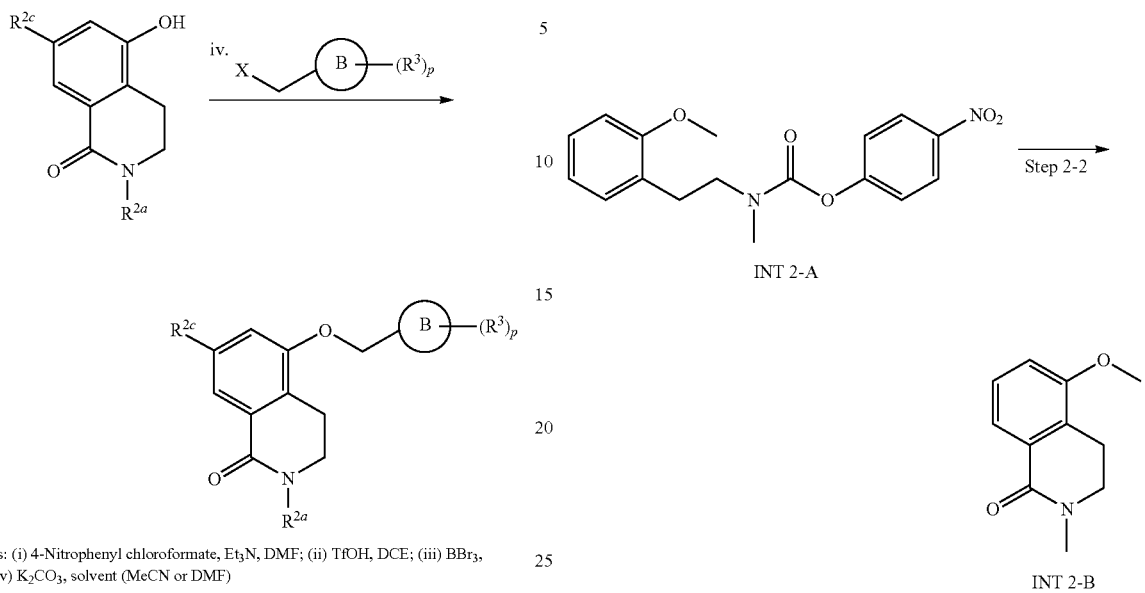

Reagents: (i) 4-Nitrophenyl chloroformate, Et₃N, DMF; (ii) TfOH, DCE; (iii) BBr₃, DCM; (iv) K₂CO₃, solvent (MeCN or DMF)

Step 2-1. Synthesis of 4-nitrophenyl (2-methoxyphenethyl)(methyl)carbamate (INT 2-A)

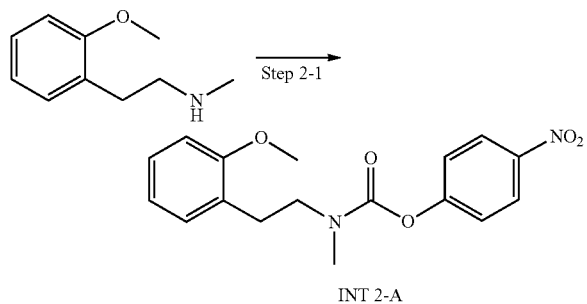

To a stirring solution of 2-(2-methoxyphenyl)-N-methylethan-1-amine (302 mg, 1.0 equiv., 1.83 mmol) in DMF (6 mL) was added triethylamine (580 mg, 0.80 mL, 3.2 equiv., 5.80 mmol), and the mixture was stirred for 10 minutes at room temperature. The reaction mixture was then charged with solid 4-nitrophenyl chloroformate (450 mg, 1.2 equiv., 2.23 mmol) in one portion, and the resulting orange suspension was stirred at room temperature for 3 hours. The reaction mixture was subsequently partitioned between EA and water, and the organic layer was collected. The aqueous layer was back-extracted 2× with EA, and the combined organic layers were washed with brine, dried over Na₂SO₄ and concentrated in vacuo. The residue was purified by flash SiO₂ chromatography (0-50% EA/hexanes) to afford 363 mg (60.1%) of 4-nitrophenyl (2-methoxyphenethyl)(methyl) carbamate (INT 2-A) as a pale yellow syrup, which was used directly in the next step. LCMS-ESI (m/z) calculated for $C_{17}H_{18}N_2O_5$: 330.12; found 331.2 [M+H]⁺, $t_R$=5.88 min (Method 1).

Step 2-2. Synthesis of 5-methoxy-2-methyl-3,4-dihydroisoquinolin-1(2H)-one (INT 2-B)

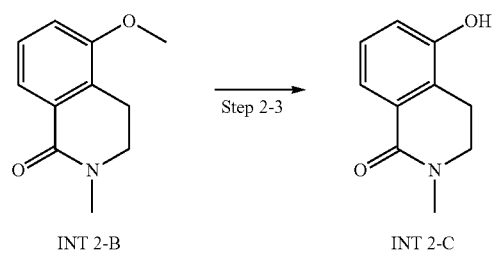

To an ice-cold solution of INT-2A (356 mg, 1.0 equiv., 1.08 mmol) in DCE (5 mL) was added triflic acid (1.67 g, 986 μL, 10.3 equiv, 11.10 mmol). The reaction mixture was stirred at 0° C. for 30 minutes, then at 70° C. for 3 hours. After cooling to room temperature, the reaction was carefully poured into ice water and was stirred for several minutes. The biphasic mixture was extracted twice with DCM. The combined organic extracts were washed with 2M Na₂CO₃, and the aqueous phase was back-extracted with DCM. The DCM layers were combined, dried over Na₂SO₄ and concentrated in vacuo. The resulting residue was purified by flash SiO₂ chromatography (10-100% EA/hexanes) to afford 136 mg (66%) of 5-methoxy-2-methyl-3,4-dihydroisoquinolin-1(2H)-one (INT 2-B) as a pale-yellow oil. LCMS-ESI (m/z) calculated for $C_{11}H_{13}NO_2$: 191.09; found 192.2 [M+H]⁺, $t_R$=5.86 min (Method 2). ¹H NMR (400 MHz, DMSO-d₆) δ 7.48 (d, J=7.8 Hz, 1H), 7.30 (t, J=8.0 Hz, 1H), 7.13 (d, J=8.2 Hz, 1H), 3.82 (s, 3H), 3.50 (t, J=6.8 Hz, 2H), 3.00 (s, 3H), 2.87 (t, J=6.8 Hz, 2H).

Step 2-3. Synthesis of 5-hydroxy-2-methyl-3,4-dihydroisoquinolin-1(2H)-one (INT 2-C)

To an ice-cold solution of INT 2-B (116 mg, 1.0 equiv., 607 μmol) in DCM (3 mL) was added 1M boron tribromide in DCM (456 mg, 1.8 mL, 3.0 equiv., 1.82 mmol). After stirring at 0° C. for a few minutes, the reaction was stirred at room temperature for 3 hours. The reaction was subsequently poured into ice water and extracted 3× with EA. The organic extracts were combined, washed with saturated NaHCO$_3$ and brine, dried over Na$_2$SO$_4$ and concentrated in vacuo to afford 88 mg (82%) of 5-hydroxy-2-methyl-3,4-dihydroisoquinolin-1(2H)-one (INT 2-C) as a tan solid. LCMS-ESI (m/z) calculated for C$_{10}$H$_{11}$NO$_2$: 177.08; found 178.1 [M+H]$^+$, t$_R$=2.18 min (Method 1). $^1$H NMR (400 MHz, DMSO-d$_6$) δ 9.69 (s, 1H), 7.34 (d, J=7.8 Hz, 1H), 7.12 (t, J=7.8 Hz, 1H), 6.95 (dd, J=8.0, 1.3 Hz, 1H), 3.49 (t, J=6.8 Hz, 2H), 3.00 (s, 3H), 2.83 (t, J=6.8 Hz, 2H).

Step 2-4. Synthesis of 5-((2-chloro-4-(trifluoromethyl)benzyl)oxy)-2-methyl-3,4-dihydroisoquinolin-1(2H)-one (Compound 2-1)

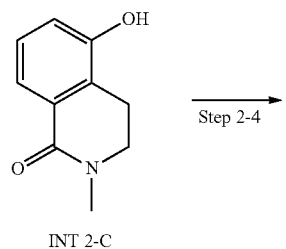

INT 2-C

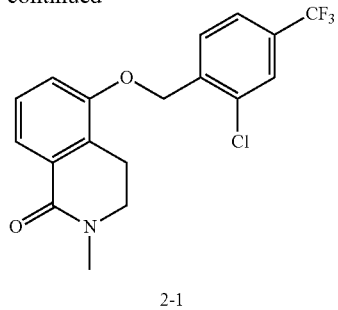

2-1

A solution of INT 2-C (34 mg, 1.0 equiv., 0.19 mmol) in DMF (2 mL) was added to a vial containing 2-chloro-1-(chloromethyl)-4-(trifluoromethyl)benzene (44 mg, 1.0 equiv., 0.19 mmol), followed by potassium carbonate (34 mg, 1.3 equiv., 0.25 mmol). The resulting yellow suspension was stirred at 80° C. for 4 hours. The reaction was cooled to room temperature, filtered, and purified by prep HPLC to afford 36.8 mg (52%) of 5-((2-chloro-4-(trifluoromethyl)benzyl)oxy)-2-methyl-3,4-dihydroisoquinolin-1(2H)-one (Compound 2-1) as a white solid. LCMS-ESI (m/z) calculated for C$_{18}$H$_{15}$ClF$_3$NO$_2$: 369.07; found 369.8, 371.8 [M+H]$^+$, t$_R$=11.08 min (Method 2). $^1$H NMR (400 MHz, DMSO-d$_6$) δ 7.96 (s, 1H), 7.87 (d, J=8.1 Hz, 1H), 7.80 (d, J=8.1 Hz, 1H), 7.54 (d, J=7.6 Hz, 1H), 7.32 (t, J=7.9 Hz, 1H), 7.26 (d, J=8.3 Hz, 1H), 5.31 (s, 2H), 3.53 (t, J=6.8 Hz, 2H), 3.02 (s, 3H), 2.96 (t, J=6.8 Hz, 2H). $^{19}$F NMR (376 MHz, DMSO-d$_6$) δ-61.15.

The compounds listed in Table 2 were made using the procedures of Scheme 2.

TABLE 2

| Structure | Cpd No. | Purity RT (min) | MW | Observed m/z | Ion | Purity Method |
|---|---|---|---|---|---|---|
| 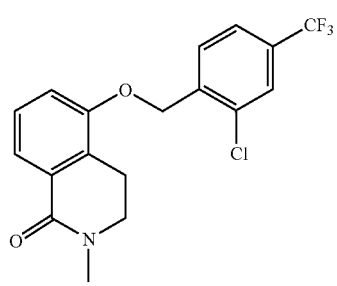 [SMILES: CN1CCc2c(OCc3ccc(C(F)(F)F)cc3Cl)cccc2C1=O] | 2-1 | 11.08 | 369.77 | 371.8 | [M + H]$^+$ | 2 |
| 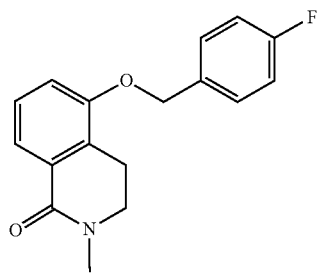 [SMILES: CN1CCc2c(OCc3ccc(F)cc3)cccc2C1=O] | 2-2 | 8.99 | 285.32 | 286.2 | [M + H]$^+$ | 2 |

TABLE 2-continued

| Structure | Cpd No. | Purity RT (min) | MW | Observed m/z | Ion | Purity Method |
|---|---|---|---|---|---|---|
| 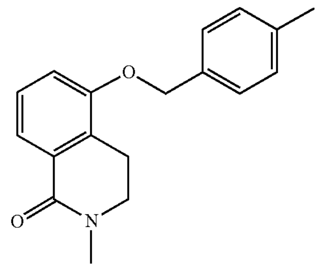 [SMILES: Cc1ccc(COc2cccc3c2CCN(C)C3=O)cc1] | 2-3 | 9.75 | 281.35 | 282.2 | [M + H]⁺ | 2 |
| 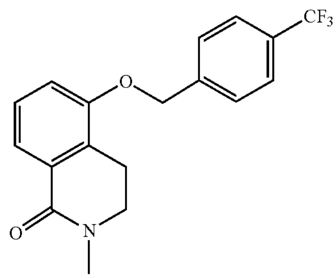 [SMILES: CN1CCc2c(OCc3ccc(C(F)(F)F)cc3)cccc2C1=O] | 2-4 | 10.08 | 335.33 | 336.1 | [M + H]⁺ | 2 |
| 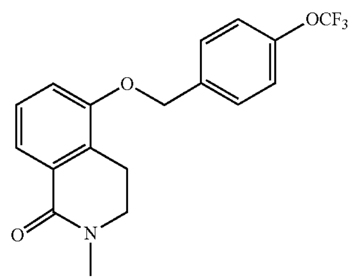 [SMILES: CN1CCc2c(OCc3ccc(OC(F)(F)F)cc3)cccc2C1=O] | 2-5 | 10.28 | 351.32 | 352.1 | [M + H]⁺ | 2 |
| 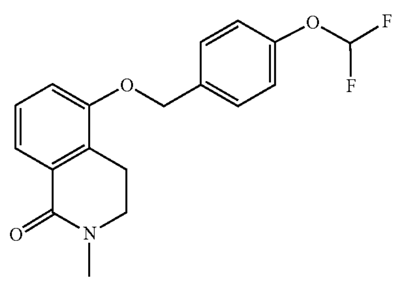 [SMILES: CN1CCc2c(OCc3ccc(OC(F)F)cc3)cccc2C1=O] | 2-6 | 9.23 | 333.33 | 334.1 | [M + H]⁺ | 2 |
| 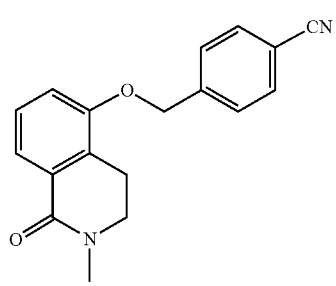 [SMILES: CN1CCc2c(OCc3ccc(C#N)cc3)cccc2C1=O] | 2-7 | 8.13 | 292.34 | 293.2 | [M + H]⁺ | 2 |

TABLE 2-continued

| Structure | Cpd No. | Purity RT (min) | MW | Observed m/z | Ion | Purity Method |
|---|---|---|---|---|---|---|
| 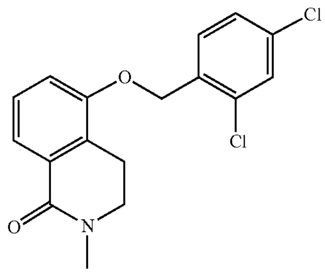 [SMILES: CN1CCc2c(OCc3ccc(Cl)cc3Cl)cccc2C1=O] | 2-8 | 11.06 | 336.21 | 338.1 | [M + H]⁺ | 2 |
| 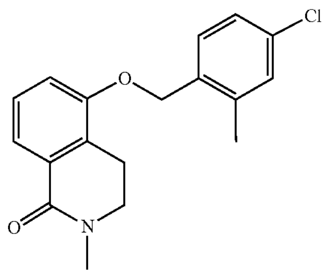 [SMILES: Cc1cc(Cl)ccc1COc1cccc2c1CCN(C)C2=O] | 2-9 | 10.54 | 315.80 | 316.1 | [M + H]⁺ | 2 |
| 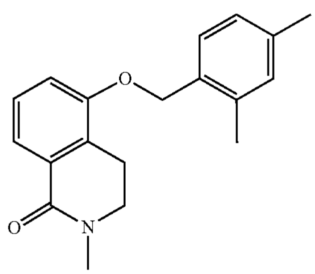 [SMILES: Cc1ccc(COc2cccc3c2CCN(C)C3=O)c(C)c1] | 2-10 | 10.39 | 295.38 | 296.2 | [M + H]⁺ | 2 |
| 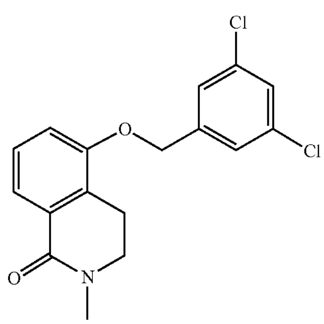 [SMILES: CN1CCc2c(OCc3cc(Cl)cc(Cl)c3)cccc2C1=O] | 2-11 | 11.02 | 336.21 | 338.1 | [M + H]⁺ | 2 |
| 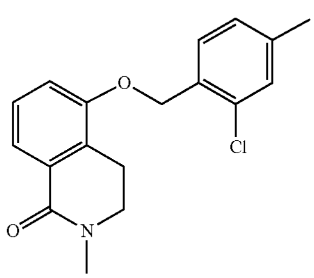 [SMILES: Cc1ccc(COc2cccc3c2CCN(C)C3=O)c(Cl)c1] | 2-12 | 10.70 | 315.80 | 316.1 | [M + H]⁺ | 2 |

TABLE 2-continued

| Structure | Cpd No. | Purity RT (min) | MW | Observed m/z | Ion | Purity Method |
|---|---|---|---|---|---|---|
| 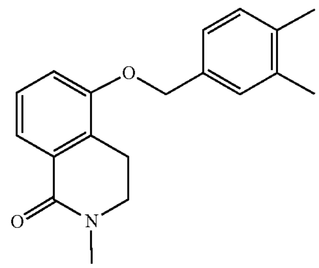 [SMILES: Cc1ccc(COc2cccc3c2CCN(C)C3=O)cc1C] | 2-13 | 10.44 | 295.38 | 296.2 | [M + H]⁺ | 2 |
| 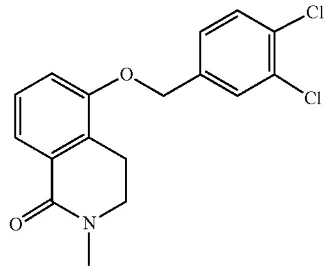 [SMILES: CN1CCc2c(OCc3ccc(Cl)c(Cl)c3)cccc2C1=O] | 2-14 | 10.70 | 336.21 | 338.1 | [M + H]⁺ | 2 |
| 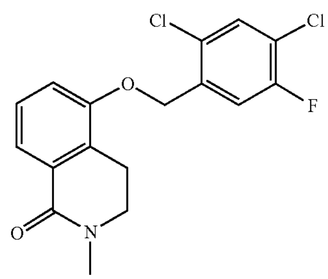 [SMILES: CN1CCc2c(OCc3cc(F)c(Cl)cc3Cl)cccc2C1=O] | 2-15 | 11.17 | 354.20 | 356.0 | [M + H]⁺ | 2 |
| 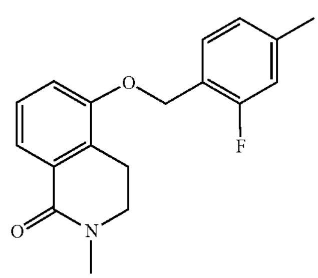 | 2-16 | 9.84 | 299.35 | 300.2 | [M + H]⁺ | 2 |
| 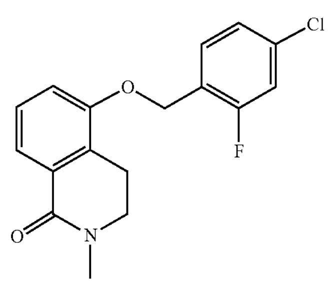 [SMILES: CN1CCc2c(OCc3ccc(Cl)cc3F)cccc2C1=O] | 2-17 | 10.14 | 319.76 | 320.1 | [M + H]⁺ | 2 |

TABLE 2-continued

| Structure | Cpd No. | Purity RT (min) | MW | Observed m/z | Ion | Purity Method |
|---|---|---|---|---|---|---|
| 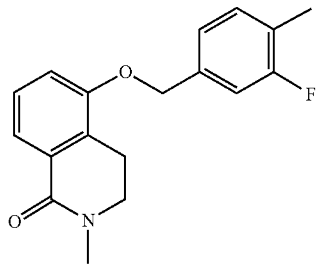 [SMILES: Cc1ccc(COc2cccc3c2CCN(C)C3=O)cc1F] | 2-18 | 9.93 | 299.35 | 300.2 | [M + H]⁺ | 2 |
| 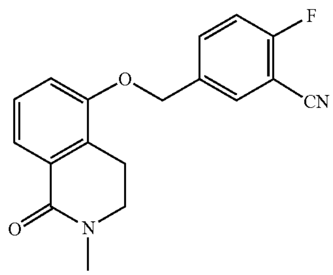 [SMILES: CN1CCc2c(OCc3ccc(F)c(C#N)c3)cccc2C1=O] | 2-19 | 8.52 | 310.33 | 311.1 | [M + H]⁺ | 2 |
| 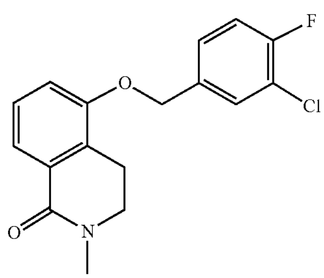 | 2-20 | 9.93 | 319.76 | 320.1 | [M + H]⁺ | 2 |
| 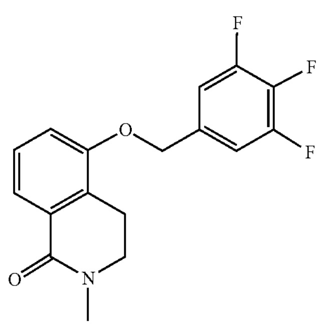 [SMILES: CN1CCc2c(OCc3cc(F)c(F)c(F)c3)cccc2C1=O] | 2-21 | 9.72 | 321.30 | 322.1 | [M + H]⁺ | 2 |
| 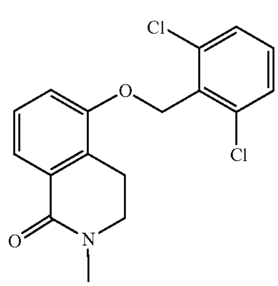 [SMILES: CN1CCc2c(OCc3c(Cl)cccc3Cl)cccc2C1=O] | 2-22 | 10.17 | 336.21 | 338.1 | [M + H]⁺ | 2 |

TABLE 2-continued

| Structure | Cpd No. | Purity RT (min) | MW | Observed m/z | Ion | Purity Method |
|---|---|---|---|---|---|---|
| 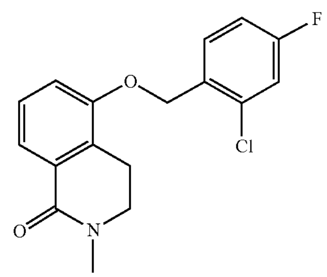 [SMILES: CN1CCc2c(OCc3ccc(F)cc3Cl)cccc2C1=O] | 2-23 | 10.05 | 319.76 | 320.1 | [M + H]+ | 2 |
| 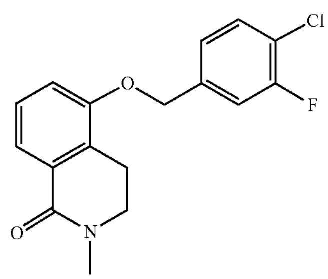 [SMILES: CN1CCc2c(OCc3ccc(Cl)c(F)c3)cccc2C1=O] | 2-24 | 10.02 | 319.76 | 320.1 | [M + H]+ | 2 |
| 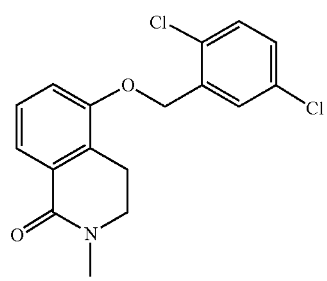 [SMILES: CN1CCc2c(OCc3cc(Cl)ccc3Cl)cccc2C1=O] | 2-25 | 10.80 | 336.21 | 338.1 | [M + H]+ | 2 |
| 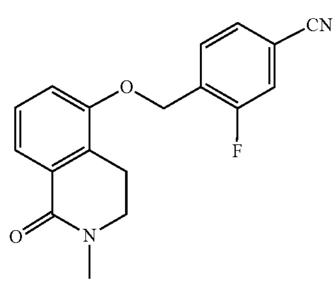 [SMILES: CN1CCc2c(OCc3ccc(C#N)cc3F)cccc2C1=O] | 2-26 | 8.43 | 310.33 | 311.1 | [M + H]+ | 2 |
| 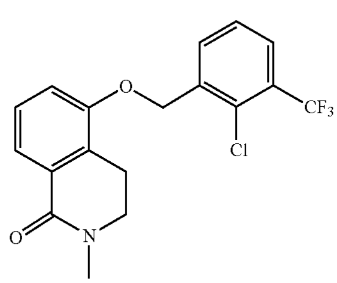 [SMILES: CN1CCc2c(OCc3cccc(C(F)(F)F)c3Cl)cccc2C1=O] | 2-27 | 10.83 | 369.77 | 370.1 | [M + H]+ | 2 |

TABLE 2-continued
| Structure | Cpd No. | Purity RT (min) | MW | Observed m/z | Ion | Purity Method |
|---|---|---|---|---|---|---|
| 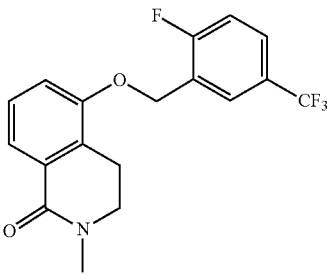 [SMILES: CN1CCc2c(OCc3cc(C(F)(F)F)ccc3F)cccc2C1=O] | 2-28 | 10.10 | 353.32 | 354.1 | [M + H]+ | 2 |
| 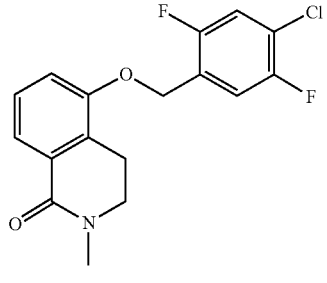 [SMILES: CN1CCc2c(OCc3cc(F)c(Cl)cc3F)cccc2C1=O] | 2-29 | 10.28 | 337.75 | 338.1 | [M + H]+ | 2 |
| 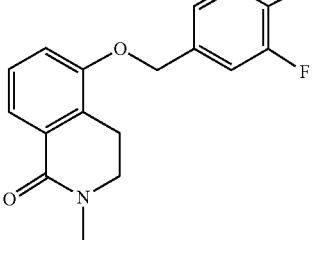 | 2-30 | 8.56 | 310.33 | 311.1 | [M + H]+ | 2 |
| 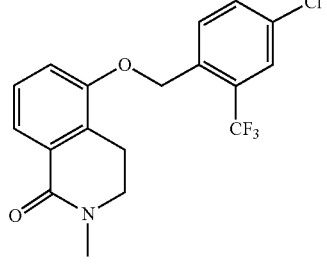 | 2-31 | 11.25 | 369.77 | 370.1 | [M + H]+ | 2 |
| 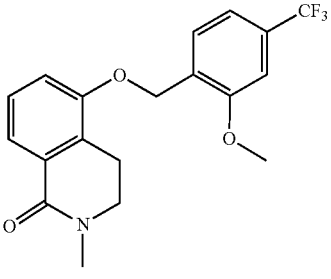 | 2-32 | 10.57 | 365.35 | 366.2 | [M + H]+ | 2 |

TABLE 2-continued

| Structure | Cpd No. | Purity RT (min) | MW | Observed m/z | Ion | Purity Method |
|---|---|---|---|---|---|---|
| 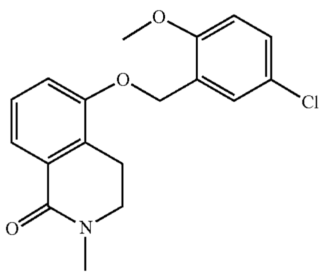 [SMILES: COc1ccc(Cl)cc1COc1cccc2c1CCN(C)C2=O] | 2-33 | 10.17 | 331.80 | 332.1 | [M + H]⁺ | 2 |
| 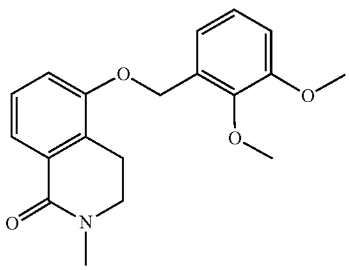 [SMILES: COc1cccc(COc2cccc3c2CCN(C)C3=O)c1OC] | 2-34 | 8.77 | 327.38 | 328.2 | [M + H]⁺ | 2 |
| 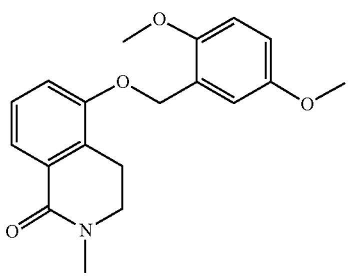 [SMILES: COc1ccc(OC)c(COc2cccc3c2CCN(C)C3=O)c1] | 2-35 | 9.01 | 327.38 | 328.2 | [M + H]⁺ | 2 |
| 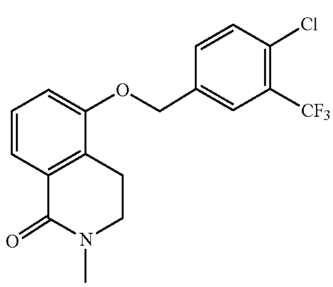 [SMILES: CN1CCc2c(OCc3ccc(Cl)c(C(F)(F)F)c3)cccc2C1=O] | 2-36 | 10.68 | 369.77 | 370.1 | [M + H]⁺ | 2 |
| 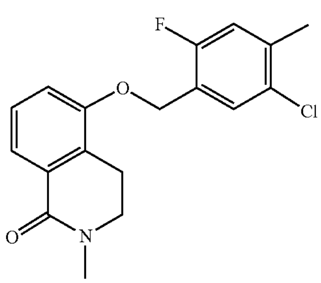 [SMILES: Cc1cc(F)c(COc2cccc3c2CCN(C)C3=O)cc1Cl] | 2-37 | 10.68 | 333.79 | 334.1 | [M + H]⁺ | 2 |

TABLE 2-continued

| Structure | Cpd No. | Purity RT (min) | MW | Observed m/z | Ion | Purity Method |
|---|---|---|---|---|---|---|
| 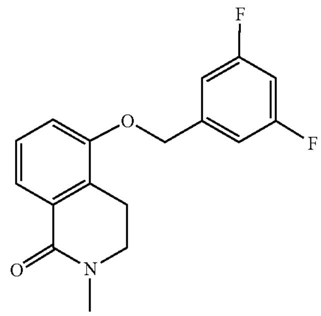 [SMILES: CN1CCc2c(OCc3cc(F)cc(F)c3)cccc2C1=O] | 2-38 | 9.34 | 303.31 | 304.1 | [M + H]⁺ | 2 |
| 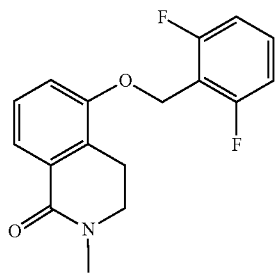 [SMILES: CN1CCc2c(OCc3c(F)cccc3F)cccc2C1=O] | 2-39 | 8.85 | 303.31 | 304.1 | [M + H]⁺ | 2 |
| 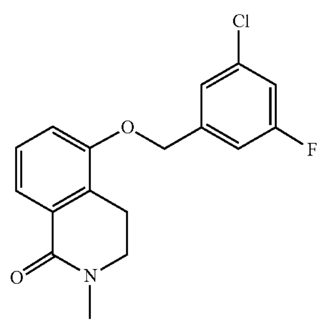 | 2-40 | 10.10 | 319.76 | 320.1 | [M + H]⁺ | 2 |
| 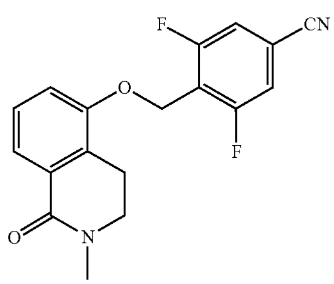 [SMILES: CN1CCc2c(OCc3c(F)cc(C#N)cc3F)cccc2C1=O] | 2-41 | 8.38 | 328.32 | 329.1 | [M + H]⁺ | 2 |
| 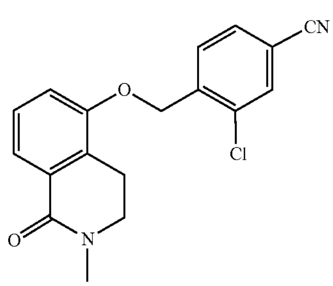 [SMILES: CN1CCc2c(OCc3ccc(C#N)cc3Cl)cccc2C1=O] | 2-42 | 9.12 | 326.78 | 327.1 | [M + H]⁺ | 2 |

TABLE 2-continued

| Structure | Cpd No. | Purity RT (min) | MW | Observed m/z | Ion | Purity Method |
|---|---|---|---|---|---|---|
| 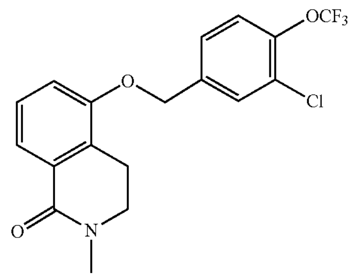 [SMILES: CN1CCc2c(OCc3ccc(OC(F)(F)F)c(Cl)c3)cccc2C1=O] | 2-43 | 10.95 | 385.77 | 386.1 | [M + H]+ | 2 |
| 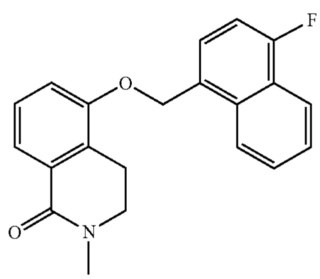 [SMILES: CN1CCc2c(OCc3ccc(F)c4ccccc34)cccc2C1=O] | 2-44 | 10.50 | 335.38 | 336.1 | [M + H]+ | 2 |
| 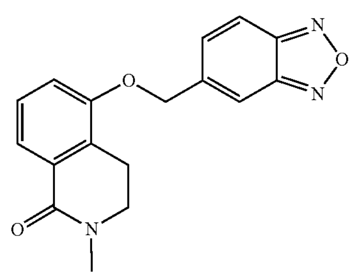 [SMILES: CN1CCc2c(OCc3ccc4nonc4c3)cccc2C1=O] | 2-45 | 7.99 | 309.32 | 310.1 | [M + H]+ | 2 |
| 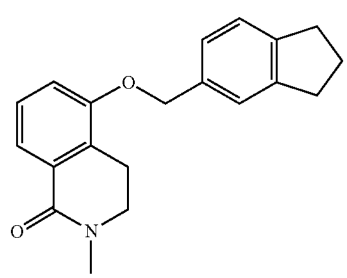 [SMILES: CN1CCc2c(OCc3ccc4c(c3)CCC4)cccc2C1=O] | 2-46 | 10.24 | 307.39 | 308.2 | [M + H]+ | 2 |

Example 3

Synthesis of Compound 3-1 and Other Representative Compounds

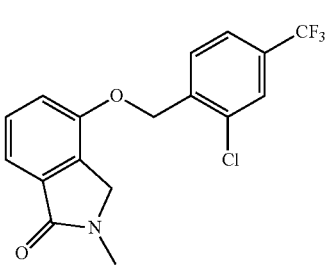

3-1

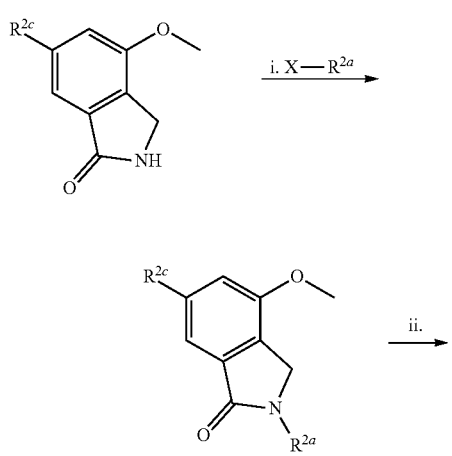

Scheme 3

Reagents: (i) NaH, DMF; (ii) BBr₃, DCM; (iii) K₂CO₃, solvent (MeCN or DMF)

Step 3-1. Synthesis of 4-methoxy-2-methylisoindolin-1-one (INT 3-A)

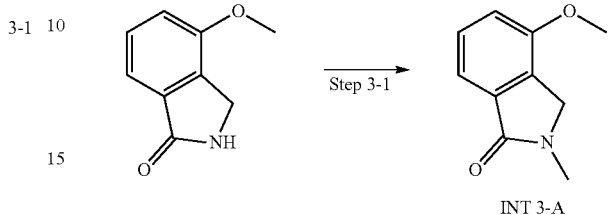

To an ice-cold solution of 4-methoxyisoindolin-1-one (300 mg, 1.0 equiv., 1.84 mmol) in DMF (5 mL) was added NaH (60% dispersion in mineral oil, 81 mg, 1.1 equiv., 2.02 mmol) in one portion. The suspension was stirred at 0° C. for 15 minutes, and was subsequently charged with iodomethane (313 mg, 137 μL, 1.2 equiv., 2.21 mmol). The resulting mixture was stirred at room temperature for 16 hours. The reaction was poured into ice water and extracted 4× with EA. The organic extracts were combined, washed with brine, dried over Na₂SO₄ and concentrated in vacuo. The residue was purified by flash SiO₂ chromatography (20-100% EA/hexanes) to afford 178 mg (54.6%) of 4-methoxy-2-methylisoindolin-1-one (INT 3-A) as a white solid. LCMS-ESI (m/z) calculated for $C_{10}H_{11}NO_2$: 177.08; found 178.2 [M+H]⁺, $t_R$=2.81 min (Method 1).

Step 3-2. Synthesis of 4-hydroxy-2-methylisoindolin-1-one (INT 3-B)

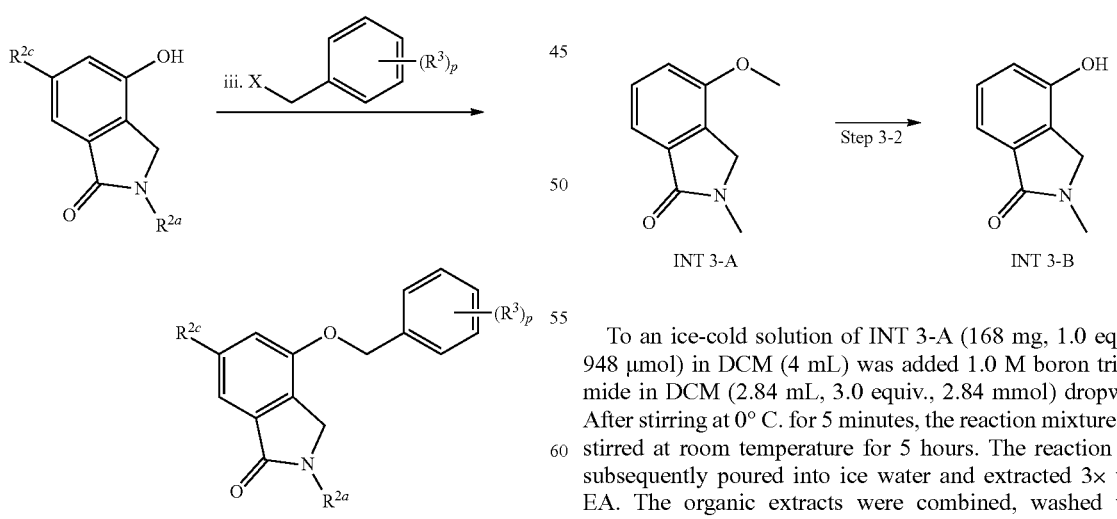

To an ice-cold solution of INT 3-A (168 mg, 1.0 equiv., 948 μmol) in DCM (4 mL) was added 1.0 M boron tribromide in DCM (2.84 mL, 3.0 equiv., 2.84 mmol) dropwise. After stirring at 0° C. for 5 minutes, the reaction mixture was stirred at room temperature for 5 hours. The reaction was subsequently poured into ice water and extracted 3× with EA. The organic extracts were combined, washed with saturated NaHCO₃ and brine, dried over Na₂SO₄ and concentrated in vacuo to afford 92 mg (59%) of 4-hydroxy-2-methylisoindolin-1-one (INT 3-B) as an off-white solid. LCMS-ESI (m/z) calculated for $C_9H_9NO_2$: 163.06; found 164.2 [M+H]⁺, $t_R$=1.70 min (Method 1).

Step 3-3. Synthesis of 4-((2-chloro-4-(trifluoromethyl)benzyl)oxy)-2-methylisoindolin-1-one (Compound 3-1)

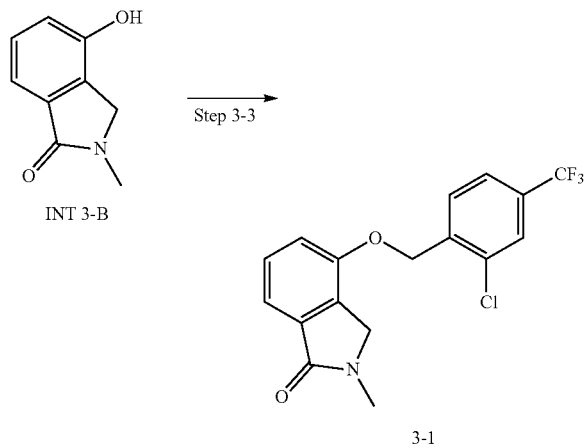

A 1-dram vial containing 2-chloro-1-(chloromethyl)-4-(trifluoromethyl)benzene (53 mg, 1.0 equiv., 0.23 mmol) was charged with a solution of INT 3-B (38 mg, 1.0 equiv., 0.23 mmol) in DMF (2 mL), followed by potassium carbonate (42 mg, 1.3 equiv., 0.30 mmol). The resulting yellow suspension stirred at 80° C. for 13 hours. The reaction was cooled to room temperature and filtered. The filtrate was purified by prep HPLC to afford 37.2 mg (45%) of 4-((2-chloro-4-(trifluoromethyl)benzyl)oxy)-2-methylisoindolin-1-one (Compound 3-1) as a white solid. LCMS-ESI (m/z) calculated for $C_{17}H_{13}Cl\ F_3NO_2$: 355.06; found 355.8 [M+H]$^+$, $t_R$=10.43 min (Method 2). $^1$H NMR (400 MHz, DMSO-$d_6$) δ 7.97 (s, 1H), 7.86 (d, J=8.1 Hz, 1H), 7.79 (d, J=8.1 Hz, 1H), 7.46 (t, J=7.8 Hz, 1H), 7.32-7.27 (m, 2H), 5.40 (s, 2H), 4.45 (s, 2H), 3.07 (s, 3H). $^{19}$F NMR (376 MHz, DMSO-$d_6$) δ-61.16.

The compounds listed in Table 3 were made using the procedures of Scheme 3.

TABLE 3

| Structure | Cpd No. | Purity RT (min) | MW | Observed m/z | Ion | Purity Method |
|---|---|---|---|---|---|---|
| 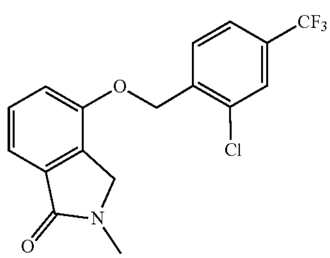 [SMILES: CN1Cc2c(OCc3ccc(C(F)(F)F)cc3Cl)cccc2C1=O] | 3-1 | 10.43 | 355.74 | 355.8 | [M + H]$^+$ | 2 |
| 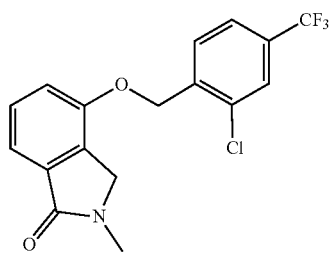 | 3-2 | 9.19 | 287.74 | 287.9 | [M + H]$^+$ | 2 |
| 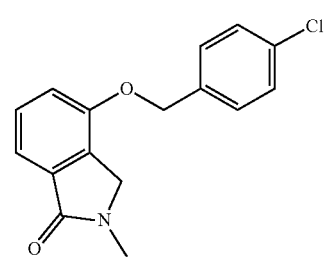 [SMILES: CN1Cc2c(OCc3ccc(Cl)cc3)cccc2C1=O] | | | | | | |

Example 4

Synthesis of Compound 4-1 and Other Representative Compounds

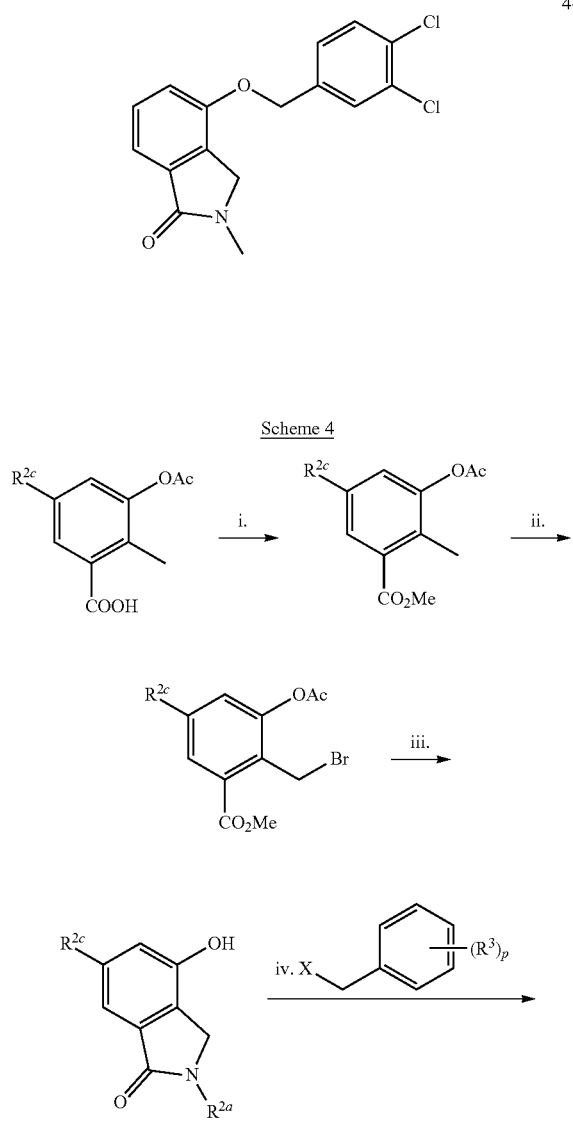

Scheme 4

Reagents: (i) CH₃I, K₂CO₃, DMF; (ii) NBS, AIBN, CCl₄; (iii) R²ᶜNH₂, THF; (iv) K₂CO₃, solvent (DMF or MeCN)

Step 4-1. Synthesis of methyl 3-acetoxy-2-methylbenzoate (INT 4-A)

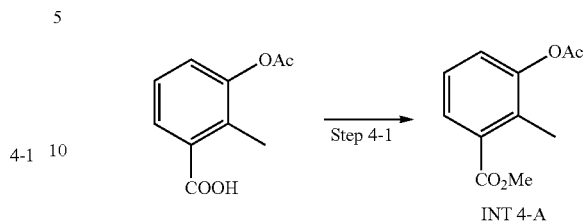

To a 250 RBF containing a stirred solution of 3-acetoxy-2-methylbenzoic acid (4.28 g, 1.0 equiv., 22.02 mmol) in DMF (42 mL) was added potassium carbonate (3.35 g, 1.1 equiv., 24.22 mmol) followed by iodomethane (1.64 mL, 1.2 equiv., 26.42 mmol). The resulting mixture was stirred at room temperature for 40 minutes. The reaction mixture was subsequently treated with water and extracted 3× with diethyl ether. The organic layers were combined, washed with brine, dried over Na₂SO₄ and dry-loaded onto Celite. The residue was purified by flash SiO₂ chromatography (0-40% EA/hexanes) to afford 2.34 g (50.9%) of methyl 3-acetoxy-2-methylbenzoate (INT 4-A) as a colorless oil. LCMS-ESI (m/z) calculated for $C_{11}H_{12}O_4$: 208.07; found 209.2 [M+H]⁺, $t_R$=4.86 min (Method 1). ¹H NMR (400 MHz, CDCl₃) δ 7.77 (d, J=7.8 Hz, 1H), 7.29-7.23 (m, 1H), 7.17 (d, J=8.0 Hz, 1H), 3.89 (s, 3H), 2.40 (s, 3H), 2.35 (s, 3H).

Step 4-2. Synthesis of methyl 3-acetoxy-2-(bromomethyl)benzoate (INT 4-B)

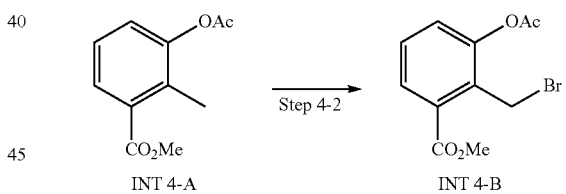

To a stirred solution of INT 4-A (2.33 g, 1.0 equiv., 11.19 mmol) in CCl₄ (55 mL) were added NBS (2.39 g, 1.1 equiv., 24.22 mmol) and AIBN (183.7 mg, 0.1 equiv., 1.12 mmol). The flask was fitted with a reflux condenser and stirred at 100° C. for 20 hours. The reaction mixture was cooled to room temperature and concentrated in vacuo. The residue was partitioned between EA and water. The organic layer was collected, and the aqueous layer was extracted twice more with EA. The organic layers were combined, dried over Na₂SO₄ and dry-loaded onto Celite. The residue was purified by flash SiO₂ chromatography (0-40% EA/hexanes) to afford 2.88 g (89.5%) of methyl 3-acetoxy-2-(bromomethyl)benzoate (INT 4-B) as a colorless oil. LCMS-ESI (m/z) calculated for $C_{11}H_{11}BrO_4$: 285.98; found 286.8, 288.8 [M+H]⁺, $t_R$=5.12 min (Method 1). ¹H NMR (400 MHz, CDCl₃) δ 7.86 (d, J=7.8 Hz, 1H), 7.41 (t, J=8.0 Hz, 1H), 7.31 (d, J=8.2 Hz, 1H), 4.94 (s, 2H), 3.95 (s, 3H), 2.41 (s, 3H).

Step 4-3. Synthesis of 4-hydroxy-2-methylisoindolin-1-one (INT 4-C)

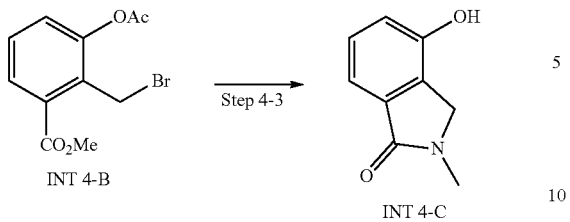

To a stirred solution of INT 4-B (2.87 g, 1.0 equiv., 11.19 mmol) in THF (28 mL) was added 2.0 M methylamine in THF (25 mL, 5.0 equiv., 49.95 mmol). The resulting white slurry was stirred at room temperature for 15 hours. The reaction mixture was subsequently concentrated in vacuo, and the residue was suspended in diethyl ether and filtered. The filter cake was washed with diethyl ether dried to yield a white solid, which was dissolved in DMSO and purified by reverse-phase flash column chromatography to afford 540 mg (33.1%) of 4-hydroxy-2-methylisoindolin-1-one (INT 4-C) as a shiny white powder. LCMS-ESI (m/z) calculated for $C_9H_9NO_2$: 163.06; found 164.0 [M+H]$^+$, $t_R$=2.19 min (Method 1). $^1$H NMR (400 MHz, DMSO-d$_6$) δ 10.02 (s, 1H), 7.28 (t, J=7.7 Hz, 1H), 7.11 (d, J=7.3 Hz, 1H), 6.96 (d, J=7.9 Hz, 1H), 4.32 (s, 2H), 3.05 (s, 3H).

Step 4-4. Synthesis of 4-((2,4-dichlorobenzyl)oxy)-2-methylisoindolin-1-one (Compound 4-1)

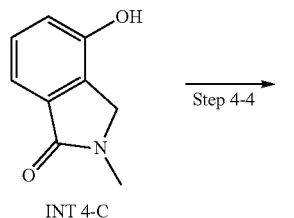

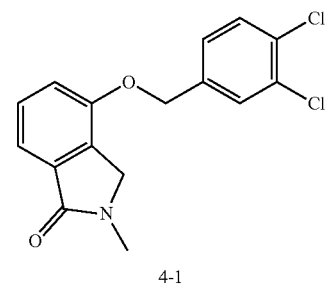

4-1

To a stirred solution of INT 4-C (50 mg, 1.0 equiv., 0.31 mmol) in DMF (2 mL) were added 3,4-dichlorobenzyl bromide (74 mg, 1.0 equiv., 0.31 mmol) and potassium carbonate (55 mg, 1.3 equiv., 0.40 mmol). The resulting white suspension was stirred at 80° C. for 20 hours. The reaction mixture was cooled to room temperature and filtered. The filtrate was purified by prep HPLC to afford 40.3 mg (41%) of 4-((2,4-dichlorobenzyl)oxy)-2-methylisoindolin-1-one (Compound 4-1) as a white solid. LCMS-ESI (m/z) calculated for $C_{16}H_{13}Cl_2O_2$: 321.03; found 322.0, 324.0 [M+H]$^+$, $t_R$=9.99 min (Method 2). $^1$H NMR (400 MHz, DMSO-d$_6$) δ 7.76 (s, 1H), 7.67 (d, J=8.3 Hz, 1H), 7.50-7.41 (m, 2H), 7.29-7.21 (m, 2H), 5.27 (s, 2H), 4.45 (s, 2H), 3.06 (s, 3H).

The compounds listed in Table 4 were made using the procedures of Scheme 4.

TABLE 4

| Structure | Cpd No. | Purity RT (min) | MW | Observed m/z | Ion | Purity Method |
|---|---|---|---|---|---|---|
| (3,4-dichlorobenzyl structure) | 4-1 | 9.99 | 322.19 | 324.0 | [M + H]$^+$ | 2 |
| (4-fluorobenzyl structure) | 4-2 | 8.35 | 271.29 | 271.9 | [M + H]$^+$ | 2 |

TABLE 4-continued

| Structure | Cpd No. | Purity RT (min) | MW | Observed m/z | Ion | Purity Method |
|---|---|---|---|---|---|---|
| (structure with OCF₃) | 4-3 | 9.70 | 337.30 | 337.9 | [M + H]⁺ | 2 |
| (structure with 2,4-diCl) | 4-4 | 10.32 | 322.19 | 324.1 | [M + H]⁺ | 2 |
| (structure with 4-Cl, 2-Me) | 4-5 | 9.86 | 301.77 | 302.1 | [M + H]⁺ | 2 |
| (structure with 2-Cl, 4-Me) | 4-6 | 9.99 | 301.77 | 302.1 | [M + H]⁺ | 2 |
| (structure with 2,4-diMe) | 4-7 | 9.73 | 281.36 | 282.2 | [M + H]⁺ | 2 |

Example 5

Synthesis of Compound 5-1 and Other Representative Compounds

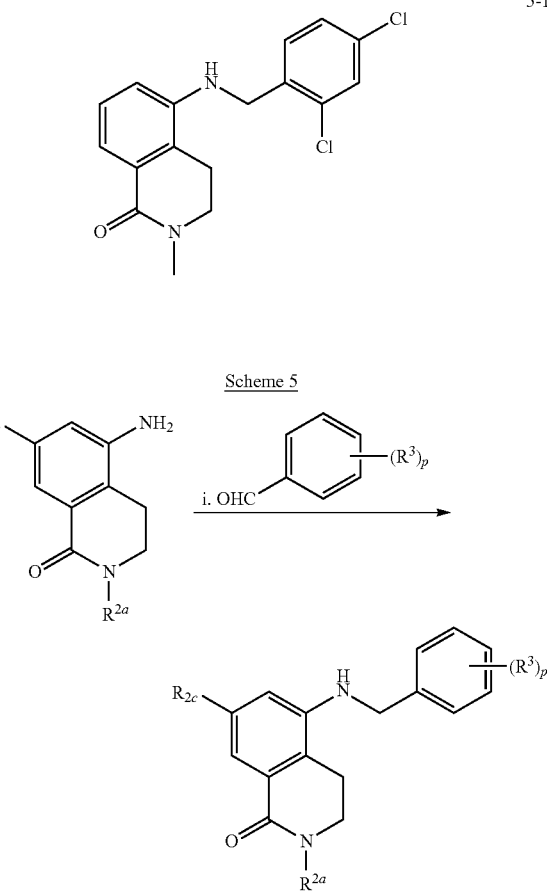

Scheme 5

Reagents: (i) NaBH(OAc)₃, HCl, DCE, MeOH

Step 5-1. Synthesis of 5-((2,4-dichlorobenzyl)amino)-2-methyl-3,4-dihydroisoquinolin-1(2H)-one (Compound 5-1)

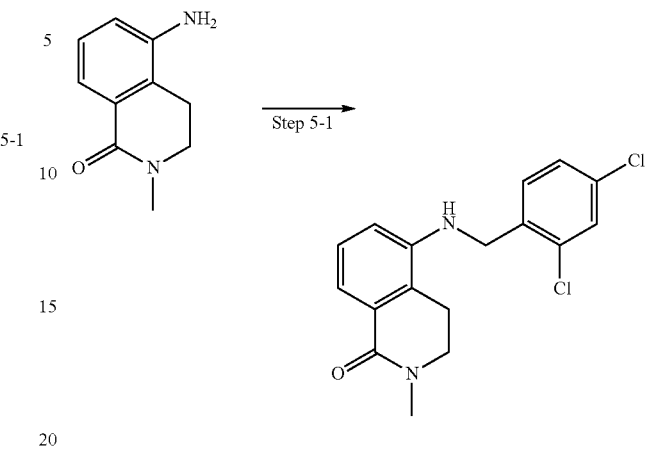

To a stirred solution of 5-amino-2-methyl-3,4-dihydroisoquinolin-1(2H)-one (80 mg, 1.0 equiv., 0.45 mmol) in DCE (10 mL) was added 2,4-dichlorobenzaldehyde (79 mg, 1.0 equiv., 0.45 mmol) followed by NaBH(OAc)$_3$ (289 mg, 3.0 equiv., 1.36 mmol). The resulting mixture was stirred at room temperature for 16 minutes. Additional NaBH(OAc)$_3$ (1.60 g, 20 equiv., 9.00 mmol) was added in one portion and the reaction was stirred for 6 hours at room temperature. The reaction mixture was then charged with 2 drops of HCl (1.25M in MeOH) followed by 2,4-dichlorobenzaldehyde (1.0 equiv.), and the reaction was stirred for 16 hours at room temperature. An additional 3 equivalents of NaBH(OAc)$_3$ were added, and after stirring for 3 hours, LCMS indicated consumption of most of the starting material. The reaction mixture was adjusted to pH 10 using 1M aq. NaOH and extracted with EA. The organic phase was washed with saturated NaHCO$_3$ and brine, dried over Na$_2$SO$_4$ and concentrated in vacuo. The residue was purified by flash SiO$_2$ chromatography (EA/hexanes) to afford 131 mg (86.3%) of 5-((2,4-dichlorobenzyl)amino)-2-methyl-3,4-dihydroisoquinolin-1(2H)-one (Compound 5-1) as a solid. LCMS-ESI (m/z) calculated for C$_{17}$H$_{16}$Cl$_2$N$_2$O: 334.06; found 335.3 [M+H]$^+$, t$_R$=13.88 min (Method 3). $^1$H NMR (400 MHz, CDCl$_3$) δ 7.56 (d, J=7.7 Hz, 1H), 7.42 (s, 1H), 7.28 (t, J=7.4 Hz, 1H), 7.23-7.13 (m, 2H), 6.63 (d, J=8.0 Hz, 1H), 4.44 (s, 2H), 4.02 (br s, 1H), 3.58 (t, J=6.8 Hz, 2H), 3.14 (s, 3H), 2.79 (t, J=6.6 Hz, 2H).

The compounds listed in Table 5 were made using the procedures of Scheme 5.

TABLE 5

| Structure | Cpd No. | Purity RT (min) | MW | Observed m/z | Ion | Purity Method |
|---|---|---|---|---|---|---|
| 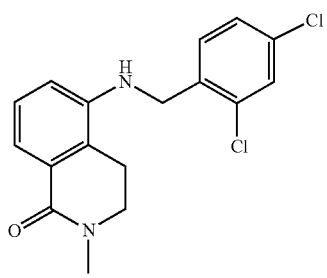 [SMILES: CN1CCc2c(NCc3ccc(Cl)cc3Cl)cccc2C1=O] | 5-1 | 13.88 | 334.06 | 335.3 | [M + H]$^+$ | 3 |

TABLE 5-continued
| Structure | Cpd No. | Purity RT (min) | MW | Observed m/z | Ion | Purity Method |
|---|---|---|---|---|---|---|
| 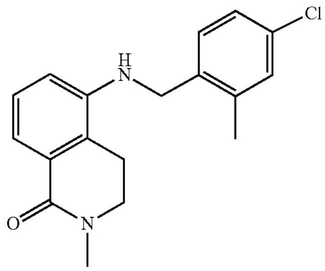 [SMILES: Cc1cc(Cl)ccc1CNc1cccc2c1CCN(C)C2=O] | 5-2 | 13.30 | 314.12 | 315.2 | [M + H]⁺ | 3 |
| 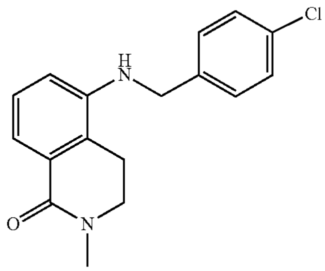 [SMILES: CN1CCc2c(NCc3ccc(Cl)cc3)cccc2C1=O] | 5-3 | 12.70 | 300.10 | 301.1 | [M + H]⁺ | 3 |
| 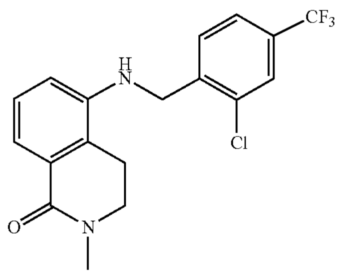 [SMILES: CN1CCc2c(NCc3ccc(C(F)(F)F)cc3Cl)cccc2C1=O] | 5-4 | 13.92 | 368.09 | 369.0 | [M + H]⁺ | 3 |
Example 6
Synthesis of Compound 6-1, Compound 6-2 and Other Representative Compounds
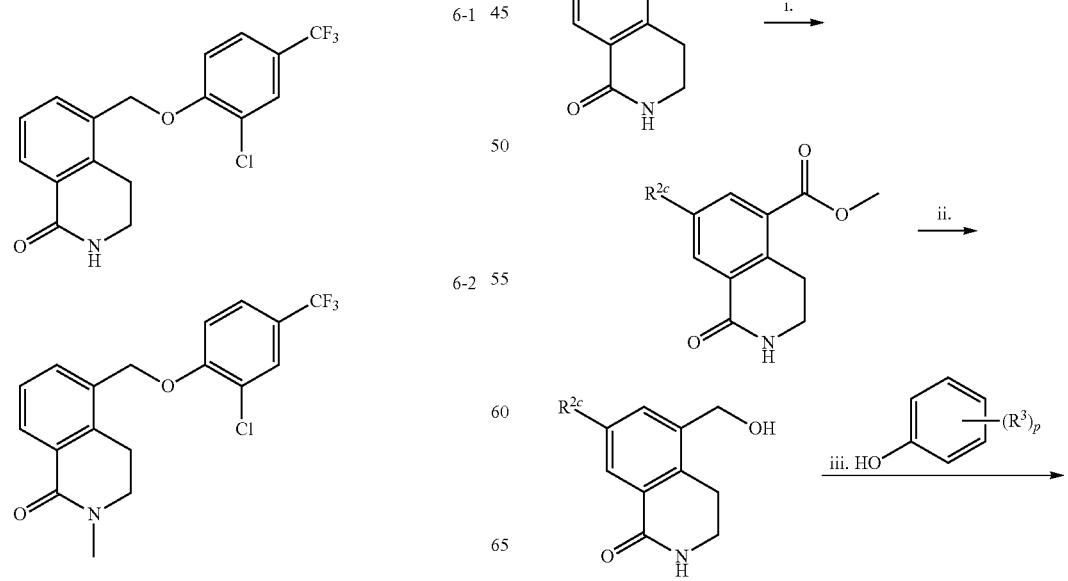

81

-continued

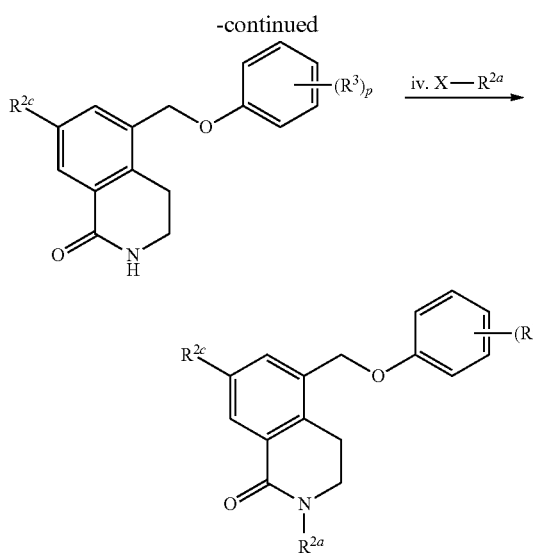

Reagents: (i) CO, Pd(dppf)Cl₂•CH₂Cl₂, solvent (DMF, MeOH); (ii) reducing agent (LiBH₄ or NaBH₄), THF; (iii) DEAD or DIAD, PPh₃, THF; (iv) NaH or KO$^t$Bu, solvent (THF or DMF)

Step 6-1. Synthesis of methyl 1-oxo-1,2,3,4-tetrahydroisoquinoline-5-carboxylate (INT 6-A)

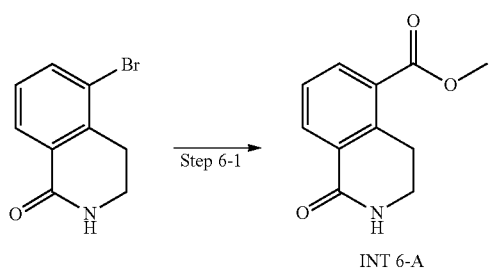

To a stirred solution of 5-bromo-3,4-dihydro-2H-isoquinolin-1-one (395 mg, 1.0 equiv., 1.75 mmol) and Et₃N (1.22 mL, 5.0 equiv., 8.74 mmol) in DMF (6 mL) was added Pd(dppf)Cl₂·DCM (285 mg, 0.2 equiv., 0.35 mmol). The mixture was evacuated and refilled with CO for 3 cycles. MeOH (3.08 mL, 43.42 equiv., 76.00 mmol) was added, and the mixture was heated to 85° C. under a CO atmosphere (1 atm) for 16 h. The mixture was diluted with EA (25 mL) and filtered through a pad of Celite. The filtrate was concentrated under reduced pressure. The residue was diluted with EA (100 mL) and water (100 mL). The aqueous phase was extracted with EA (3×25 mL). The combined organic layers were washed with brine (50 mL), dried over Na₂SO₄, and concentrated in vacuo. The residue was purified by flash SiO₂ chromatography (0-100% EA/hexanes) to afford 285 mg (80%) of methyl 1-oxo-1,2,3,4-tetrahydroisoquinoline-5-carboxylate (INT 6-A). MS-ESI calculated for C₁₁H₁₁NO₃: 205.07; found 205.74 [M]⁺, $t_R$=1.82 min (Method 5). ¹H NMR (400 MHz, CDCl₃) δ 8.30 (dd, J=7.7, 1.5 Hz, 1H), 8.09 (dd, J=7.8, 1.5 Hz, 1H), 7.42 (dd, J=7.8 Hz, 1H), 5.95 (s, 1H), 3.92 (s, 3H), 3.58-3.52 (m, 2H), 3.49-3.40 (m, 2H).

82

Step 6-2. Synthesis of 5-(hydroxymethyl)-3,4-dihydroisoquinolin-1(2H)-one (INT 6-B)

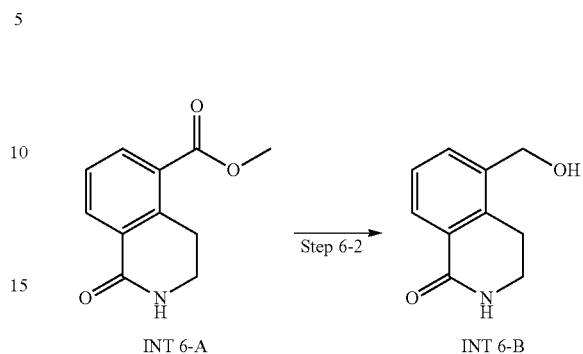

To a stirred solution of INT 6-A (182 mg, 1.0 equiv., 0.89 mmol) in THF (5 mL) at room temperature under nitrogen was added LiBH₄ (2 M in THF, 2.66 mL, 6.0 equiv., 5.32 mmol). The resulting mixture was stirred at room temperature for 20 hours. The mixture was diluted with sat. aq. NH₄Cl (10 mL). The aq. phase was extracted with EA (3×20 mL), and the combined organic phases were washed with brine (50 mL), dried over Na₂SO₄, and concentrated in vacuo to afford 88 mg (56%) of 5-(hydroxymethyl)-3,4-dihydroisoquinolin-1(2H)-one (INT 6-B). MS-ESI (m/z) calculated for C₁₀H₁₁NO₂: 177.08; found 178.13 [M+H]⁺, $t_R$=1.39 min (Method 5). ¹H NMR (500 MHz, CDCl₃) δ 8.07 (dd, J=7.8, 1.4 Hz, 1H), 7.52 (dd, J=7.6, 1.4 Hz, 1H), 7.36 (t, J=7.7 Hz, 1H), 5.95 (s, 1H), 4.75 (s, 2H), 3.57 (td, J=6.7, 2.9 Hz, 2H), 3.07 (t, J=6.6 Hz, 2H), 1.72 (s, 1H).

Step 6-3. Synthesis of 5-((2-chloro-4-(trifluoromethyl)phenoxy)methyl)-3,4-dihydroisoquinolin-1(2H)-one (Compound 6-1)

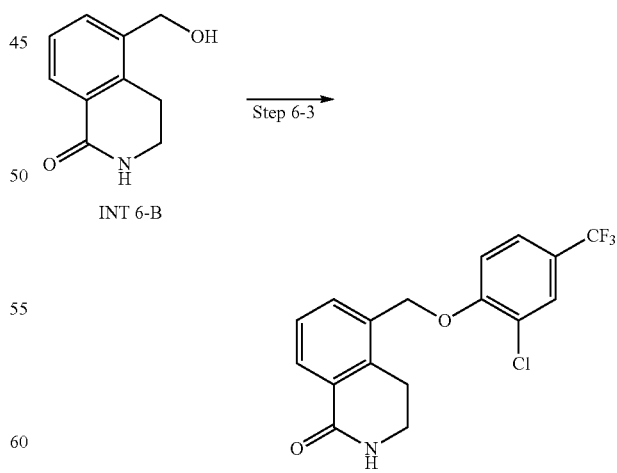

To an ice-cold mixture of INT 6-B (88 mg, 1.0 equiv., 0.50 mmol), 2-chloro-4-(trifluoromethyl)phenol (69.7 µL, 1.04 equiv., 0.52 mmol), and PPh₃ (143 mg, 1.1 equiv., 0.55 mmol) in THF (5 mL) was added DIAD (108 μL, 1.1 equiv., 0.55 mmol). The resulting mixture was stirred at room temperature for 18 hours, then concentrated in vacuo. Some of this material was used without further purification in the next step. The remainder of the material was further purified by reverse-phase chromatography (MeCN/H$_2$O containing 0.1% formic acid) to afford 32.7 mg (19%) of 5-((2-chloro-4-(trifluoromethyl)phenoxy)methyl)-3,4-dihydroisoquinolin-1(2H)-one (Compound 6-1) as a solid. MS-ESI (m/z) calculated for C$_{17}$H$_{13}$ClF$_3$NO: 355.06; found 356.07 [M+H]$^+$, t$_R$=4.69 min (Method 4). $^1$H NMR (500 MHz, DMSO-d$_6$) δ 8.00 (s, 1H), 7.90 (dd, J=7.8, 1.4 Hz, 1H), 7.88-7.85 (m, 1H), 7.73 (ddd, J=8.7, 2.3, 0.9 Hz, 1H), 7.68 (dd, J=7.6, 1.4 Hz, 1H), 7.52 (d, J=8.6 Hz, 1H), 7.40 (dd, J=7.6 Hz, 1H), 5.38 (s, 2H), 3.38 (td, J=6.6, 2.8 Hz, 2H), 2.96 (t, J=6.6 Hz, 2H).

Step 6-4. Synthesis of 5-((2-chloro-4-(trifluoromethyl)phenoxy)methyl)-2-methyl-3,4-dihydroisoquinolin-1(2H)-one (Compound 6-2)

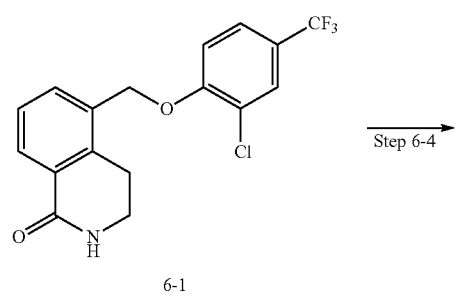

6-1

Step 6-4

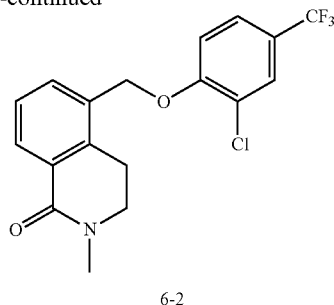

6-2

To an ice-cold solution of Compound 6-1 (154 mg, 50% purity, 1.0 equiv., 0.22 mmol) in THF (5 mL) was added NaH (24.9 mg, 5.0 equiv., 1.08 mmol). The resulting mixture was stirred at room temperature for 30 minutes. Iodomethane (67.4 μL, 5.0 equiv., 1.08 mmol) was added, and the mixture was stirred at 70° C. for 1 hour. The mixture was diluted with MeOH (10 mL) and concentrated in vacuo. The residue was purified by reverse phase chromatography (CH$_3$CN/H$_2$O containing 0.1% formic acid) to afford 60.4 mg (76%) of 5-((2-chloro-4-(trifluoromethyl)phenoxy)methyl)-2-methyl-3,4-dihydroisoquinolin-1(2H)-one (Compound 6-2) as a solid. MS-ESI (m/z) calculated for C$_{18}$H$_{15}$ClF$_3$NO$_2$: 369.07; found 370.08 [M+H]$^+$, t$_R$=5.08 min (Method 4). $^1$H NMR (400 MHz, DMSO-d$_6$) δ 7.92 (dd, J=7.8, 1.4 Hz, 1H), 7.86 (dd, J=2.3, 0.7 Hz, 1H), 7.73 (ddd, J=8.7, 2.3, 0.8 Hz, 1H), 7.66 (dd, J=7.6, 1.4 Hz, 1H), 7.52 (d, J=8.7 Hz, 1H), 7.39 (dd, J=7.7 Hz, 1H), 5.38 (s, 2H), 3.56 (t, J=6.7 Hz, 2H), 3.07-2.99 (m, 5H).

The compounds listed in Table 6 were made using the procedures of Scheme 6.

TABLE 6

| Structure | Cpd No. | Purity RT (min) | MW | Observed m/z | Ion | Purity Method |
|---|---|---|---|---|---|---|
| 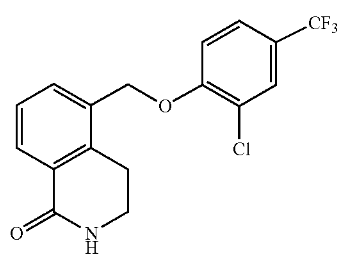 [SMILES: O=C1NCCc2c(COc3ccc(C(F)(F)F)cc3Cl)cccc21] | 6-1 | 4.69 | 355.74 | 356.07 | [M + H]$^+$ | 4 |
| 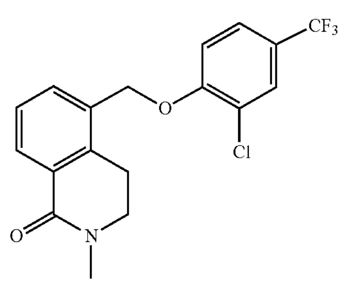 [SMILES: CN1CCc2c(COc3ccc(C(F)(F)F)cc3Cl)cccc2C1=O] | 6-2 | 5.08 | 369.77 | 370.08 | [M + H]$^+$ | 4 |

Example 7

Synthesis of Compound 7-1 and Other Representative Compounds

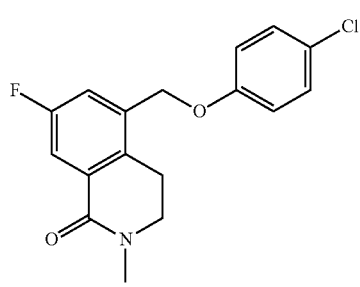

7-1

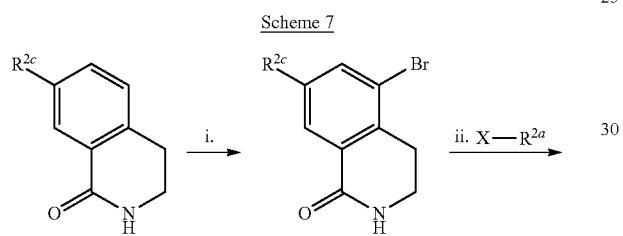

Scheme 7

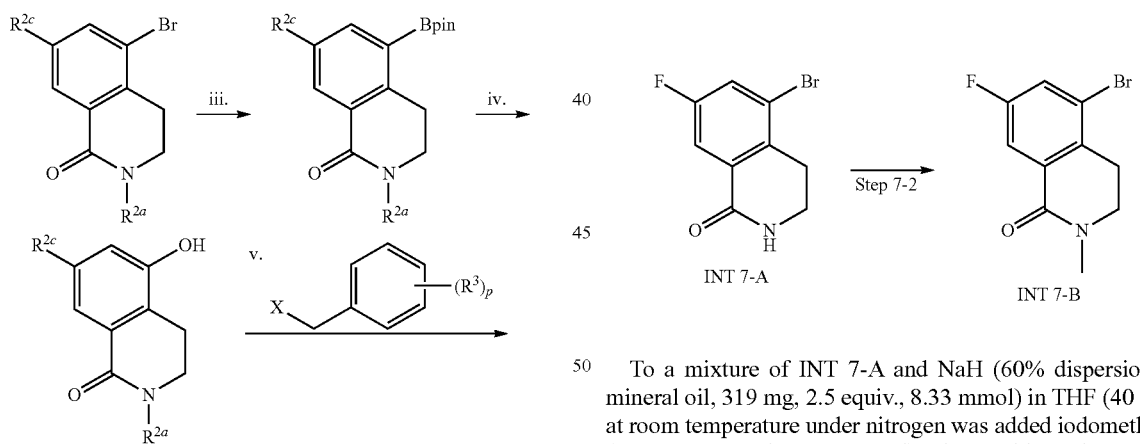

Reagents: (i) NBS, H$_2$SO$_4$; (ii) NaH, THF; (iii) (Bpin)$_2$, Pd(dppf)Cl$_2$·CH$_2$Cl$_2$, KOAc, THF; (iv) Oxone®, acetone, H$_2$O; (v) K$_2$CO$_3$, solvent (DMF or THF)

Step 7-1. Synthesis of 5-bromo-7-fluoro-3,4-dihydroisoquinolin-1(2H)-one (INT 7-A)

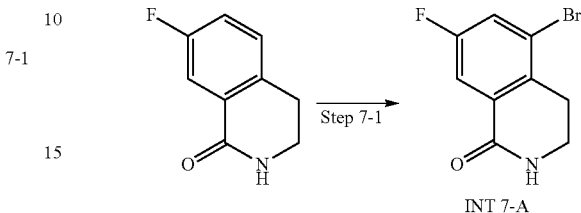

INT 7-A

To a stirred solution of 7-fluoro-3,4-dihydro-2H-isoquinolin-1-one (550 mg, 1.0 equiv., 3.33 mmol) in H$_2$SO$_4$ (20 mL) at room temperature under nitrogen was added NBS (711 mg, 1.2 equiv., 4.00 mmol). The mixture was stirred at room temperature for 22 hours. The reaction was diluted with ice water (40 mL), filtered, washed with water (40 mL), and dried to provide 5-bromo-7-fluoro-3,4-dihydroisoquinolin-1(2H)-one (INT 7A), which was used immediately in the next step.

Step 7-2. 5-bromo-7-fluoro-2-methyl-3,4-dihydroisoquinolin-1(2H)-one (INT 7-B)

INT 7-A → INT 7-B

To a mixture of INT 7-A and NaH (60% dispersion in mineral oil, 319 mg, 2.5 equiv., 8.33 mmol) in THF (40 mL) at room temperature under nitrogen was added iodomethane (415 µL, 2.0 equiv., 6.66 mmol). The resulting mixture was stirred at room temperature for 18 hours. The reaction was diluted with 1M HCl (40 mL), and the aqueous phase was extracted with EA (3×50 mL). The combined organic phases were washed with brine (100 mL), dried over Na$_2$SO$_4$, and concentrated in vacuo. The residue was purified by flash SiO$_2$ chromatography (0-50 EA/hexanes) to afford 585 mg (55% over two steps) of 5-bromo-7-fluoro-2-methyl-3,4-dihydroisoquinolin-1(2H)-one (INT 7-B) as a solid. MS (ESI) [M]$^+$ calculated for C$_{10}$H$_9$BrFNO: 256.99; found 258.13 [M+H]$^+$, t$_R$=2.34 min (Method 5). $^1$H NMR (400 MHz, CDCl$_3$) δ 7.80 (dd, J=8.8, 2.7 Hz, 1H), 7.41 (dd, J=7.8, 2.7 Hz, 1H), 3.57 (t, J=6.8 Hz, 2H), 3.16 (s, 3H), 3.08-3.02 (m, 2H).

Step 7-3. Synthesis of 7-fluoro-2-methyl-5-(4,4,5,5-tetramethyl-1,3,2-dioxaborolan-2-yl)-3,4-dihydroisoquinolin-1(2H)-one (INT 7-C)

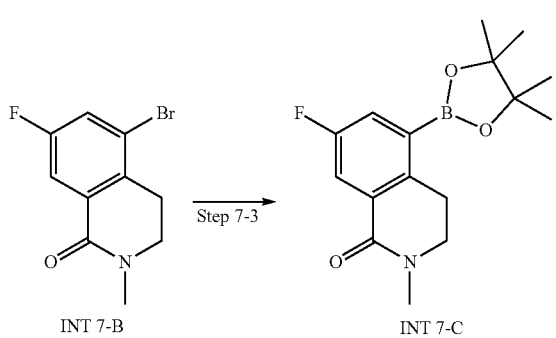 [SMILES: CN1CCc2c(Br)cc(F)cc2C1=O ; CN1CCc2c(B3OC(C)(C)C(C)(C)O3)cc(F)cc2C1=O]

A mixture of INT 7-B (585 mg, 1.0 equiv., 2.27 mmol), B$_2$pin$_2$ (1.44 g, 2.5 equiv., 5.67 mmol), KOAc (667 mg, 3.0 equiv., 6.80 mmol), and Pd(dppf)Cl$_2$ (332 mg, 0.2 equiv., 0.45 mmol) in THF (30 mL) was stirred at 70° C. for 18 h. The mixture was diluted with EA (20 mL) and filtered through Celite. The filter cake was washed with EA (100 mL), and the filtrate was concentrated in vacuo. The residue was purified by flash SiO$_2$ chromatography (0-75% EA/hexanes) to provide 7-fluoro-2-methyl-5-(4,4,5,5-tetramethyl-1,3,2-dioxaborolan-2-yl)-3,4-dihydroisoquinolin-1(2H)-one (INT 7-C), which was used immediately in the next step.

Step 7-4. Synthesis of 7-fluoro-5-hydroxy-2-methyl-3,4-dihydroisoquinolin-1(2H)-one (INT 7-D)

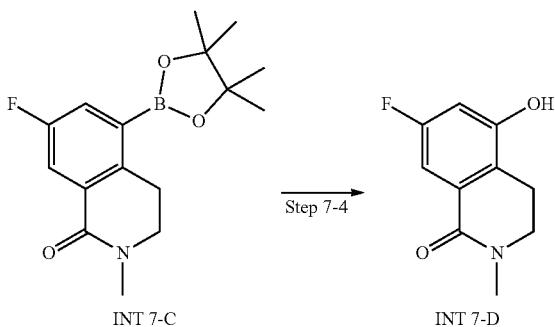 [SMILES: CN1CCc2c(B3OC(C)(C)C(C)(C)O3)cc(F)cc2C1=O ; CN1CCc2c(O)cc(F)cc2C1=O]

To a mixture of INT 7-C in acetone (50 mL) was added Oxone® (1.53 g, 1.1 equiv., 2.49 mmol) in water (10 mL). The resulting mixture was stirred for 2 hours at room temperature. The reaction mixture was diluted with aqueous NaHSO$_3$ (60 mL). The aqueous phase was extracted with EA (3×50 mL). The combined organic phases were washed with brine (100 mL), dried over Na$_2$SO$_4$, and concentrated in vacuo. The residue was purified by flash SiO$_2$ chromatography (0-100% EA/hexanes) to afford 218 mg (47% over two steps) of 7-fluoro-5-hydroxy-2-methyl-3,4-dihydroisoquinolin-1(2H)-one (INT 7-D) as a solid. MS-ESI (m/z) calculated for C$_{10}$H$_{10}$FNO$_2$: 195.07; found 194.20 [M–H]$^-$, t$_R$=1.92 min (Method 5). $^1$H NMR (400 MHz, DMSO-d$_6$) δ 10.26 (s, 1H), 7.04 (dd, J=9.4, 2.7 Hz, 1H), 6.74 (dd, J=10.5, 2.7 Hz, 1H), 3.50 (t, J=6.8 Hz, 2H), 3.00 (s, 3H), 2.79 (t, J=6.5 Hz, 2H).

Step 7-5. Synthesis of 5-(4-chlorobenzyl)oxy)-7-fluoro-2-methyl-3,4-dihydroisoquinolin-1(2H)-one (Compound 7-1)

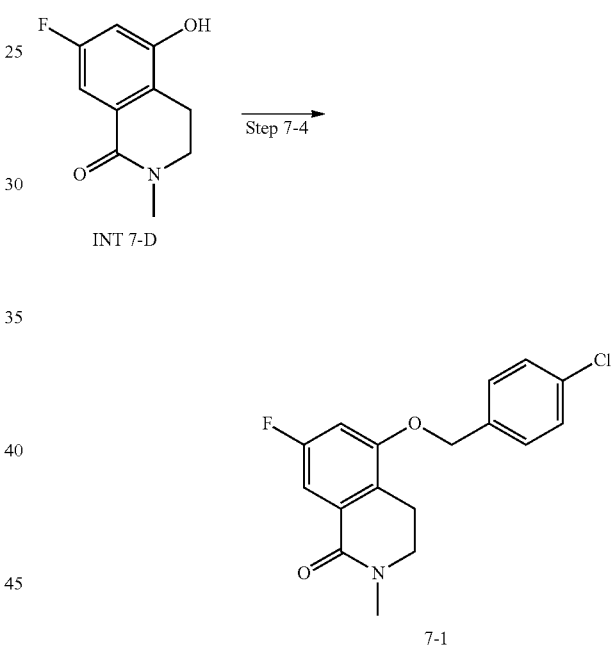

A mixture of INT 7-D (46 mg, 1.0 equiv., 0.24 mmol), 1-(bromomethyl)-4-chloro-benzene (53.3 mg, 1.1 equiv., 0.26 mmol) and K$_2$CO$_3$ (97.7 mg, 3.0 equiv., 0.71 mmol) in DMF (2 mL) was stirred at 70° C. for 5 hours. The mixture was cooled to room temperature and concentrated. The residue was purified by preparative HPLC (5-100% ACN/NH$_4$OAc 10 mM, pH 4) to afford 49 mg (58%) of 5-(4-chlorobenzyl)oxy)-7-fluoro-2-methyl-3,4-dihydroisoquinolin-1(2H)-one (Compound 7-1) as a solid. MS-ESI (m/z) calculated for C$_{17}$H$_{15}$Cl FNO$_2$: 319.08; found 319.08 [M]$^+$, t$_R$=4.90 min (Method 4). $^1$H NMR (400 MHz, DMSO-d$_6$) δ 7.52-7.46 (m, 4H), 7.21-7.15 (m, 2H), 5.18 (s, 2H), 3.52 (t, J=6.8 Hz, 2H), 3.01 (s, 3H), 2.87 (t, J=7.3 Hz, 2H). $^{19}$F NMR (376 MHz, DMSO-d$_6$) δ-113.00 (dd, J=10.6, 9.5 Hz).

The compounds listed in Table 7 were made using the procedures of Scheme 7.

TABLE 7
| Structure | Cpd No. | Purity RT (min) | MW | Observed m/z | Ion | Purity Method |
|---|---|---|---|---|---|---|
| 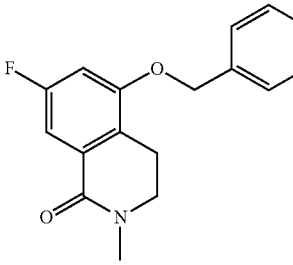 | 7-1 | 4.90 | 319.76 | 319.08 | [M]+ | 4 |
| 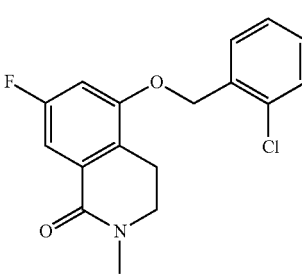 | 7-2 | 5.58 | 387.76 | 387.10 | [M]+ | 4 |
Example 8
Synthesis of Compound 8-1 and Other Representative Compounds
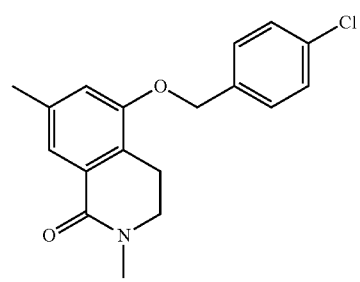
8-1
Scheme 8
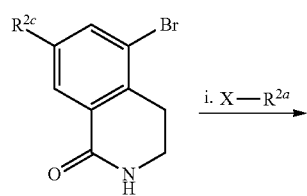
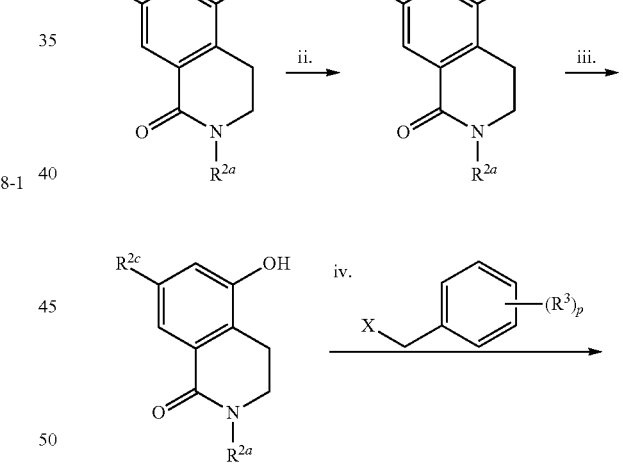
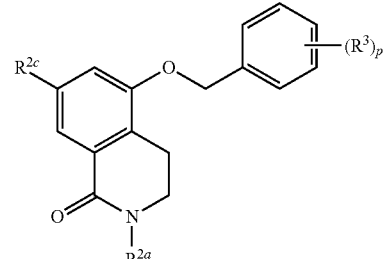
Reagents: (i) NaH, THF; (ii) (Bpin)$_2$, Pd(dppf)Cl$_2$·CH$_2$Cl$_2$, KOAc, THF; (iii) Oxone®, acetone, H$_2$O; (iv) K$_2$CO$_3$, solvent (DMF or THF)

Step 8-1. Synthesis of 5-bromo-2,7-dimethyl-3,4-dihydroisoquinolin-1-one (INT 8-A)

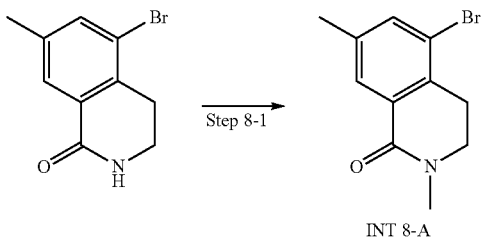

INT 8-A

To an ice-cold solution of 5-bromo-7-methyl-3,4-dihydro-2H-isoquinolin-1-one (100 mg, 1.0 equiv., 0.42 mmol) in THF (4 mL) under nitrogen was added NaH (60% in oil, 31.9 mg, 2.0 equiv., 0.84 mmol), and the resulting mixture was stirred at 0° C. for 30 minutes. Iodomethane (38.9 µL, 1.5 equiv., 0.625 mmol) was added, and the mixture was stirred at room temperature for 18 hours. The reaction mixture was diluted with water (5 mL) and stirred for 30 minutes at room temperature. The aqueous phase was extracted with EA (3×25 mL). The combined organic phases were washed with sat. aq. $Na_2S_2O_3$ (5 mL) and brine (25 mL), dried over $Na_2SO_4$, and concentrated in vacuo to afford 106 mg (99%) of 5-bromo-2,7-dimethyl-3,4-dihydroisoquinolin-1(2H)-one (INT 8-A) as a solid. MS-ESI (m/z) calculated for $C_{11}H_{12}BrNO$: 253.01; found 255.35 [M+H]$^+$, $t_R$=2.27 min (Method 5). $^1$H NMR (400 MHz, CDCl$_3$) δ 7.92-7.82 (m, 1H), 7.48 (dd, J=1.8, 0.8 Hz, 1H), 3.55 (dd, J=7.1, 6.5 Hz, 2H), 3.15 (s, 3H), 3.05 (t, J=6.8 Hz, 2H), 2.35 (t, J=0.7 Hz, 3H).

Step 8-2. 2,7-dimethyl-5-(4,4,5,5-tetramethyl-1,3,2-dioxaborolan-2-yl)-3,4-dihydroisoquinolin-1(2H)-one (INT 8-B)

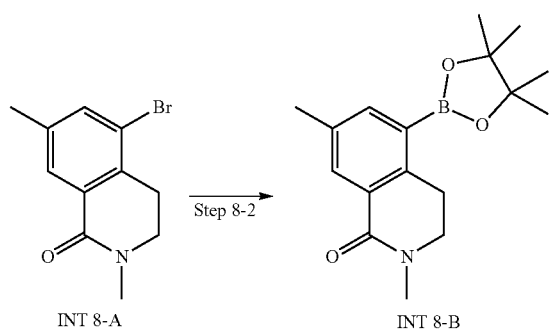

INT 8-A INT 8-B

A mixture of INT 8-A (106 mg, 1.0 equiv., 0.42 mmol), bis(pinacolato)diboron (127 mg, 1.2 equiv., 0.50 mmol), KOAc (123 mg, 3.0 equiv., 1.25 mmol) and Pd(dppf)Cl$_2$ (15.3 mg, 0.05 equiv., 0.021 mmol) in THF (4 mL) was stirred at 70° C. for 72 hours. The mixture was diluted with EA (20 mL), filtered through a pad of Celite with EtOAc (40 mL), and concentrated in vacuo. The residue was purified by flash SiO$_2$ chromatography with (0-60% EA/hexanes) to afford 2,7-dimethyl-5-(4,4,5,5-tetramethyl-1,3,2-dioxaborolan-2-yl)-3,4-dihydroisoquinolin-1(2H)-one (INT 8-B) as a solid, which was used in the next step without further purification.

Step 8-3. Synthesis of 5-hydroxy-2,7-dimethyl-3,4-dihydroisoquinolin-1(2H)-one (INT 8-C)

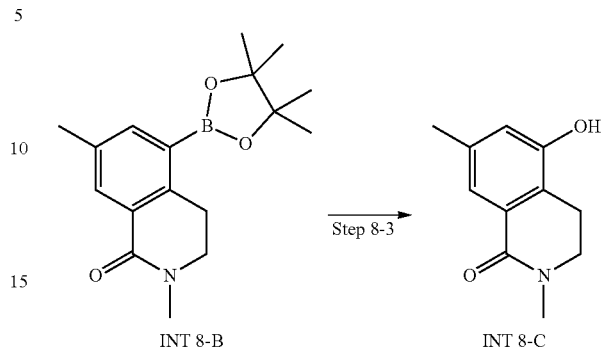

INT 8-B INT 8-C

A solution of Oxone® (282 mg, 0.459 mmol, in 4 mL of water) was added to a mixture of INT 8-B in acetone (20 mL), and the mixture was stirred at room temperature for 2 hours. The mixture was subsequently diluted with saturated aq. NaHSO$_3$ (40 mL) and acidified with aq. HCl (pH 4). The aqueous phase was extracted with EA (3×50 mL). The combined organic phases were washed with brine (100 mL), dried over Na$_2$SO$_4$, and concentrated in vacuo. The residue was purified by flash SiO$_2$ chromatography (0-10% CH$_2$Cl$_2$/MeOH) to afford 52 mg (47% over two steps) of 5-hydroxy-2,7-dimethyl-3,4-dihydroisoquinolin-1(2H)-one (INT 8-C) as a solid. MS-ESI (m/z) calculated for $C_{11}H_{13}NO_2$: 191.09; found 190.46 [M−H]$^-$; $t_R$=1.76 min (Method 5). $^1$H NMR (500 MHz, CDCl$_3$) δ 7.52 (d, J=1.6 Hz, 1H), 6.73 (dd, J=1.6, 0.8 Hz, 1H), 5.08 (s, 1H), 3.54 (t, J=6.9 Hz, 2H), 3.14 (s, 3H), 2.93 (t, J=6.8 Hz, 2H), 2.31 (t, J=0.7 Hz, 3H).

Step 8-4. Synthesis of 5-((4-chlorobenzyl)oxy)-2,7-dimethyl-3,4-dihydroisoquinolin-1(2H)-one (Compound 8-1)

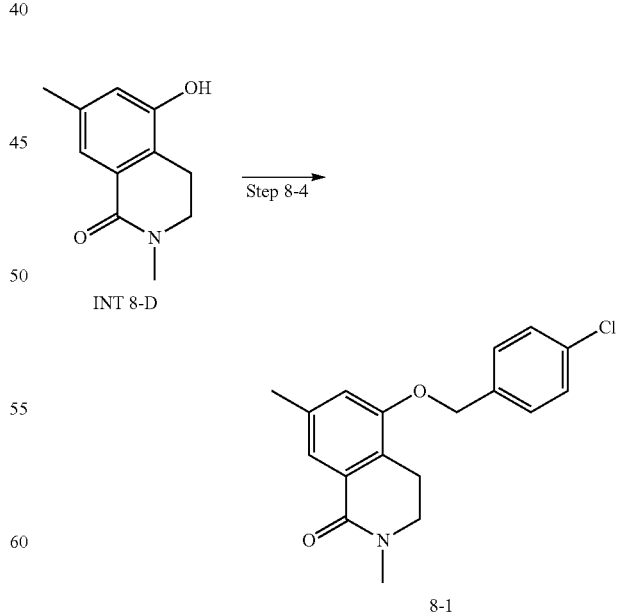

INT 8-D 8-1

A mixture of INT 8-C (50 mg, 1.0 equiv., 0.26 mmol), 1-(bromomethyl)-4-chloro-benzene (80.6 mg, 1.5 equiv., 0.39 mmol), and K$_2$CO$_3$ (108 mg, 3.0 equiv., 0.78 mmol) in DMF (2 mL) was stirred at 70° C. for 24 hours. The mixture was diluted with water (25 mL) and DCM (25 mL). The aqueous phase was extracted with DCM (3×25 mL). The combined organic phases were washed with brine (25 mL), dried over $Na_2SO_4$, and concentrated in vacuo. The residue was purified by reverse phase chromatography with water (+10 mM $NH_4OAc$) and MeCN (0-80%) to afford 51.8 mg (63%) of 5-((4-chlorobenzyl)oxy)-2,7-dimethyl-3,4-dihydroisoquinolin-1(2H)-one (Compound 8-1) as a solid. MS-ESI (m/z) calculated for $C_{18}H_{18}ClNO_2$: 315.10; found 315.10 $[M]^+$; $t_R$=4.98 min (Method 4). $^1H$ NMR (400 MHz, DMSO-$d_6$) δ 7.53-7.44 (m, 4H), 7.33 (dd, J=1.6, 0.8 Hz, 1H), 7.07 (d, J=1.6 Hz, 1H), 5.13 (s, 2H), 3.49 (t, J=6.8 Hz, 2H), 3.00 (s, 3H), 2.86 (t, J=6.8 Hz, 2H), 2.32 (s, 3H).

The compounds listed in Table 8 were made using the procedures of Scheme 8.

TABLE 8

| Structure | Cpd No. | Purity RT (min) | MW | Observed m/z | Ion | Purity Method |
|---|---|---|---|---|---|---|
| (structure) | 8-1 | 4.98 | 315.80 | 315.10 | $[M]^+$ | 4 |
| (structure) | 8-2 | 5.70 | 383.09 | 383.09 | $[M]^+$ | 4 |

Example 9

MRGPR X4 Activity

HEK cells stably transfected to express human MRGPR X4 were maintained in an incubator at 37° C. with 5% $CO_2$ and grown in DMEM media with 10% fetal bovine serum (FBS) and 1% each of sodium pyruvate, Glutamax, penicillin/streptomycin, and Geneticin. HEK cells stably transfected to express mouse MRGPR A1 were maintained in the same incubator and grown in DMEM media with 10% FBS, 1% each of sodium pyruvate, Glutamax, penicillin/streptomycin, Geneticin, and 2.2 mg/mL Hygromycin.

Cells were plated in a 384-well assay plate at 20,000 cells per well in 12 μL of Opti-MEM and kept in an incubator overnight. On the day of the assay, compounds solubilized at 10 mM in DMSO were added as a 10-point curve (10 uM final top concentration with 1:3 serial dilutions) using a Tecan D300E digital dispenser. Agonists were diluted in assay buffer (final concentrations of 5.7 mM Tris-HCl, 43 mM NaCl, 50 mM LiCl, pH=8) and 2 μL of the appropriate agonist are added to each well. Final concentrations of agonists were 10 μM bilirubin, 20 μM deoxycholic acid, or 100 μM conjugated bilirubin (obtained from Lee Biosolutions, catalog #910-12). Final concentrations of DMSO were kept consistent across the plate. Plates were incubated in the dark for 1 h at 37° C. and then for 30 minutes at room temperature. IP-1 standards and HTRF detection reagents were added according to the IP-One—Gq Kit purchased from Cisbio (part number 62IPAPEJ) and incubated in the dark for 1 h at room temperature. The plate was read on a Molecular Devices SpectraMax iD5 plate reader. The HTRF ratio was calculated from the raw data and graphed using GraphPad Prism to calculate an $IC_{50}$ value for each compound.

Activity data for selected MRGPR X4 antagonists (versus 20 μM deoxycholic acid agonist) are displayed in Table 9. The activity ranges are denoted as follows: "+++++" denotes antagonist activity <100 nM; "++++" denotes antagonist activity between 100 and 500 nM; "+++" denotes activity between 501 and 1000 nM; "++" denotes activity between 1001 and 2500 nM; and "+" denotes activity >2500 nM

TABLE 9

| Cpd No. | MRGPR4 Antagonist Activity |
|---|---|
| 1-1 | + |
| 1-2 | ++ |
| 1-3 | + |
| 1-4 | +++ |
| 1-5 | +++ |
| 1-6 | ++++ |
| 1-7 | +++ |
| 1-8 | + |
| 2-1 | ++++ |
| 2-2 | + |
| 2-3 | ++ |
| 2-4 | +++ |
| 2-5 | ++ |
| 2-6 | ++ |
| 2-7 | ++++ |

TABLE 9-continued

| Cpd No. | MRGPR4 Antagonist Activity |
|---|---|
| 2-8 | +++ |
| 2-9 | +++++ |
| 2-10 | +++ |
| 2-11 | + |
| 2-12 | ++ |
| 2-13 | + |
| 2-14 | ++++ |
| 2-15 | ++++ |
| 2-16 | + |
| 2-17 | ++++ |
| 2-18 | ++ |
| 2-19 | + |
| 2-20 | ++ |
| 2-21 | +++ |
| 2-22 | + |
| 2-23 | +++ |
| 2-24 | +++ |
| 2-25 | + |
| 2-26 | + |
| 2-27 | ++ |
| 2-28 | ++ |
| 2-29 | +++ |
| 2-30 | ++ |
| 2-31 | + |
| 2-32 | +++ |
| 2-33 | ++++ |
| 2-34 | + |
| 2-35 | +++++ |
| 2-36 | +++ |
| 2-37 | + |
| 2-38 | + |
| 2-39 | + |
| 2-40 | + |
| 2-41 | +++ |
| 2-42 | +++ |
| 2-43 | + |
| 2-44 | ++ |
| 2-45 | ++ |
| 2-46 | + |
| 3-1 | ++++ |
| 3-2 | +++ |
| 4-1 | +++ |
| 4-2 | + |
| 4-3 | + |
| 4-4 | ++++ |
| 4-5 | ++++ |
| 4-6 | ++ |
| 4-7 | ++++ |
| 5-1 | ++ |
| 5-2 | ++ |
| 5-3 | + |
| 5-4 | + |
| 6-1 | + |
| 6-2 | ++ |
| 7-1 | ++++ |
| 7-2 | +++ |
| 8-1 | + |
| 8-2 | + |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

This application claims the benefit of priority to U.S. Provisional Application No. 63/011,964, filed Apr. 17, 2020, which application is hereby incorporated by reference in its entirety.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the structure of Formula (IX):

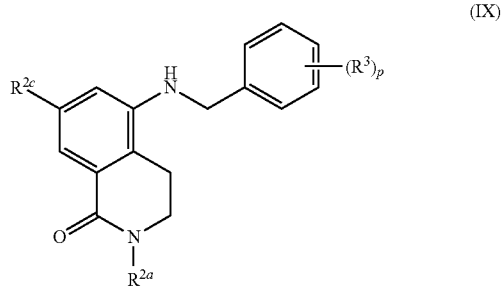

(IX)

or a pharmaceutically acceptable isomer, racemate, hydrate, solvate, isotope, or salt thereof, wherein:
$R^{2a}$ is alkyl;
$R^{2c}$ is H, halo, alkyl, haloalkyl, or aralkyl;
each $R^3$ is, independently, halo, alkyl, haloalkyl, alkoxy, haloalkoxy, carbocycle or heterocycle, —CN, —$(CH_2)_qC(O)OR^4$, —$(CH_2)_qNHR^5$, —$(CH_2)_qOR^6$, —$C(O)NR^7R^8$, or a carboxylic acid isostere;
each $R^4$, $R^5$, $R^6$, and $R^7$ is, independently, H or alkyl;
each $R^8$ is, independently, H, —$SO_2CH_3$, carbocycle, heterocycle, or alkyl,
wherein each $R^8$ is independently substituted with 0, 1, 2, or 3 $R^9$;
each $R^9$ is —OH, —CN, —NR'R", —C(O)OH, —C(O)NR'R", —$SO_2OH$, alkoxy, carbocycle, or heterocycle;
each R' is, independently, H or alkyl;
each R" is, independently, H or alkyl;
p is 0-3; and
q is 0-6.

2. A compound having the structure of Formula (X):

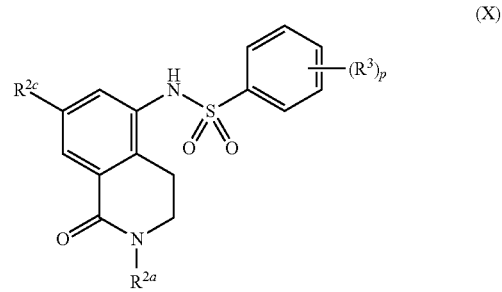

(X)

or a pharmaceutically acceptable isomer, racemate, hydrate, solvate, isotope, or salt thereof, wherein:
$R^{2a}$ is alkyl;
$R^{2c}$ is H, halo, alkyl, haloalkyl, or aralkyl;
each $R^3$ is, independently, halo, alkyl, haloalkyl, alkoxy, haloalkoxy, carbocycle or heterocycle, —CN, —$(CH_2)_qC(O)OR^4$, —$(CH_2)_qNHR^5$, —$(CH_2)_qOR^6$, —$C(O)NR^7R^8$, or a carboxylic acid isostere;

each $R^4$, $R^5$, $R^6$, and $R^7$ is, independently, H or alkyl;

each $R^8$ is, independently, H, —$SO_2CH_3$, carbocycle, heterocycle, or alkyl, wherein each $R^8$ is independently substituted with 0, 1, 2, or 3 $R^9$;

each $R^9$ is —OH, —CN, —NR'R", —C(O)OH, —C(O)NR'R", —$SO_2OH$, alkoxy, carbocycle, or heterocycle;

each R' is, independently, H or alkyl;

each R" is, independently, H or alkyl;

p is 0-3; and q is 0-6.

3. A compound having the structure of Formula (XII):

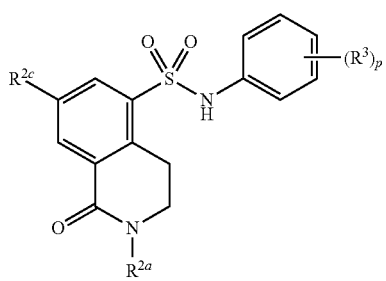

(XII)

or a pharmaceutically acceptable isomer, racemate, hydrate, solvate, isotope, or salt thereof, wherein:

$R^{2a}$ and $R^{2c}$ are each, independently, H, halo, alkyl, haloalkyl, or aralkyl;

each $R^3$ is, independently, halo, alkyl, haloalkyl, alkoxy, haloalkoxy, carbocycle or heterocycle, —CN, —$(CH_2)_qC(O)OR^4$, —$(CH_2)_qNHR^5$, —$(CH_2)_qOR^6$, —$C(O)NR^7R^8$, or a carboxylic acid isostere;

each $R^4$, $R^5$, $R^6$, and $R^7$ is, independently, H or alkyl;

each $R^8$ is, independently, H, —$SO_2CH_3$, carbocycle, heterocycle, or alkyl, wherein each $R^8$ is independently substituted with 0, 1, 2, or 3 $R^9$;

each $R^9$ is —OH, —CN, —NR'R", —C(O)OH, —C(O)NR'R", —$SO_2OH$, alkoxy, carbocycle, or heterocycle;

each R' is, independently, H or alkyl;

each R" is, independently, H or alkyl; p is 0-3; and q is 0-6.

4. A compound having one of the structures listed in the following table, or a pharmaceutically acceptable isomer, racemate, hydrate, solvate, isotope, or salt thereof:

| Cpd. No. | Structure |
|---|---|
| 1-1 | ![structure] |
| 1-2 | ![structure] |
| 1-3 | ![structure] |
| 1-4 | ![structure] |
| 1-5 | ![structure] |
| 1-6 | ![structure] |

-continued
| Cpd. No. | Structure |
|---|---|
| 1-7 | 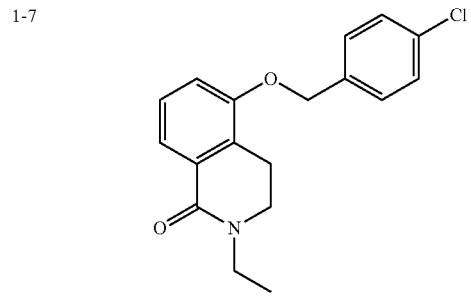 |
| 1-8 | 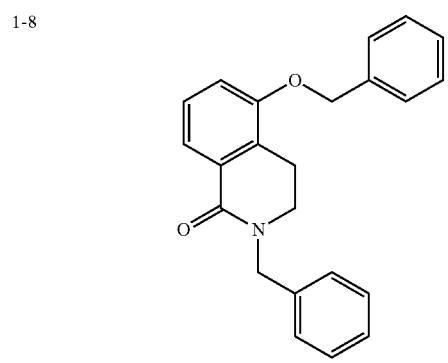 |
| 2-1 | 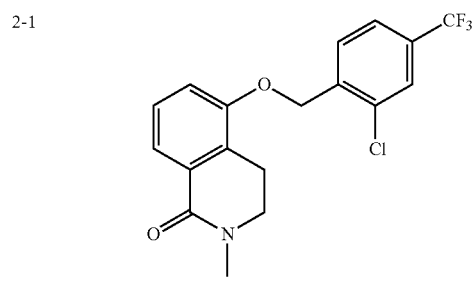 |
| 2-2 | 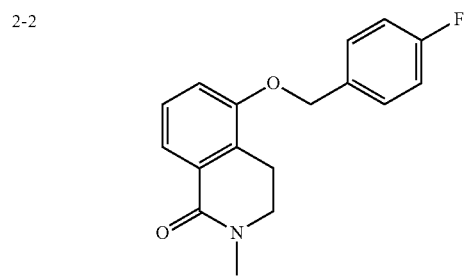 |
| 2-3 | 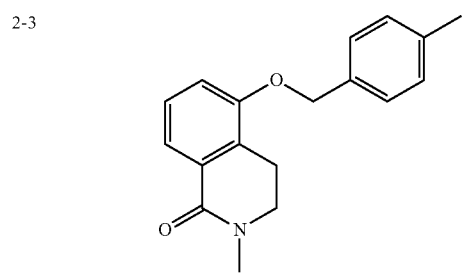 |
-continued
| Cpd. No. | Structure |
|---|---|
| 2-4 | 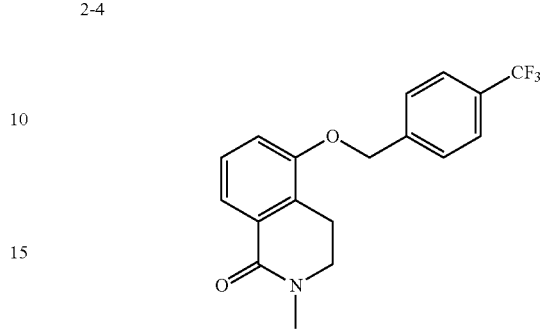 |
| 2-5 | 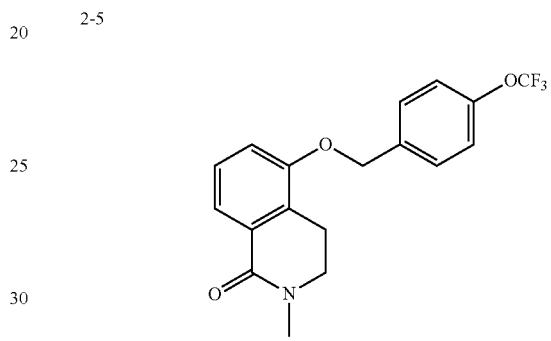 |
| 2-6 | 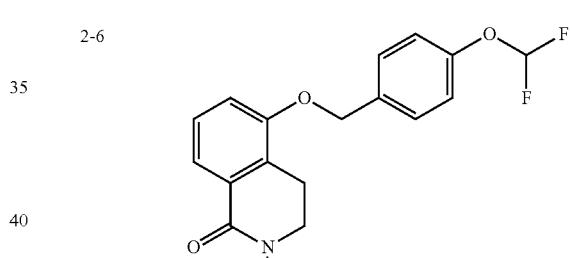 |
| 2-7 | 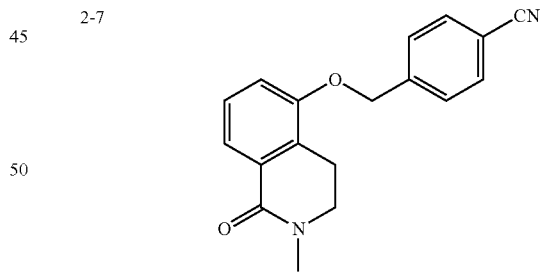 |
| 2-8 | 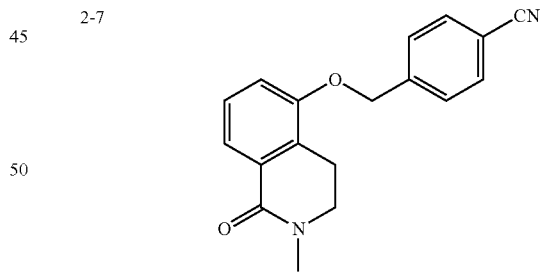 |

| Cpd. No. | Structure |
|---|---|
| 2-9 | 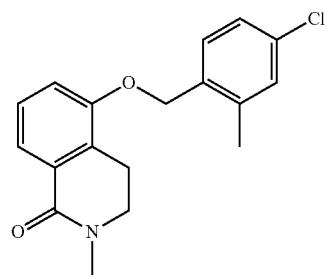 [SMILES: Cc1cc(Cl)ccc1COc1cccc2c1CCN(C)C2=O] |
| 2-10 | 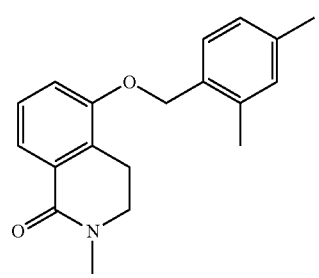 |
| 2-11 | 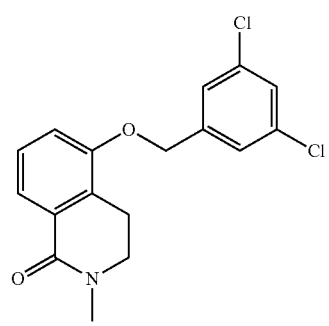 [SMILES: CN1CCc2c(OCc3cc(Cl)cc(Cl)c3)cccc2C1=O] |
| 2-12 | 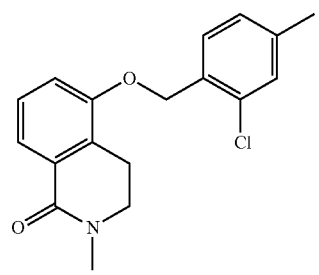 |
| 2-13 | 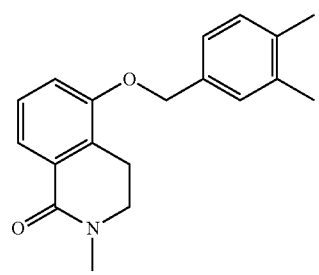 [SMILES: Cc1ccc(COc2cccc3c2CCN(C)C3=O)cc1C] |
| Cpd. No. | Structure |
|---|---|
| 2-14 | 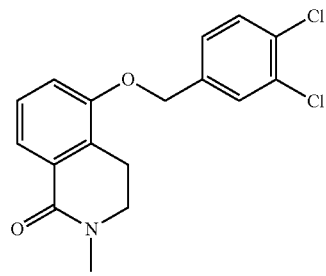 |
| 2-15 | 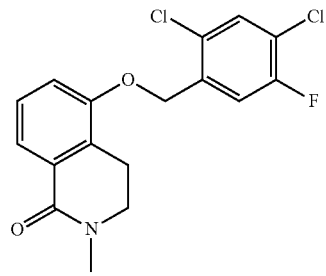 |
| 2-16 | 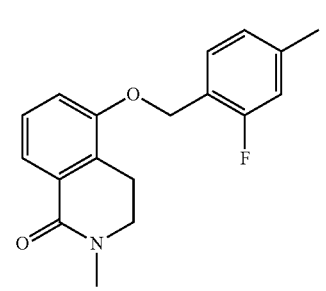 [SMILES: Cc1ccc(COc2cccc3c2CCN(C)C3=O)c(F)c1] |
| 2-17 | 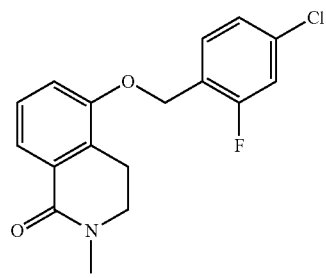 |
| 2-18 | 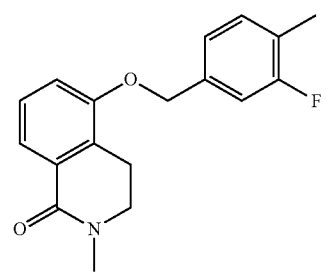 [SMILES: Cc1ccc(COc2cccc3c2CCN(C)C3=O)cc1F] |

| Cpd. No. | Structure |
|---|---|
| 2-19 | 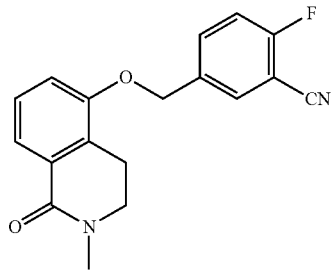 [SMILES: CN1CCc2c(OCc3ccc(F)c(C#N)c3)cccc2C1=O] |
| 2-20 | 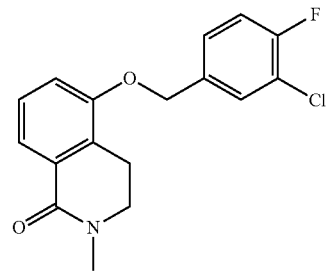 |
| 2-21 | 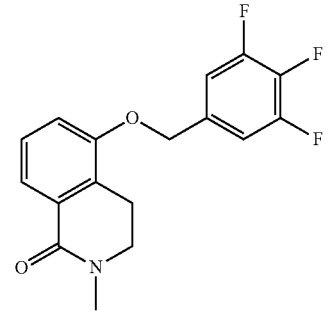 [SMILES: CN1CCc2c(OCc3cc(F)c(F)c(F)c3)cccc2C1=O] |
| 2-22 | 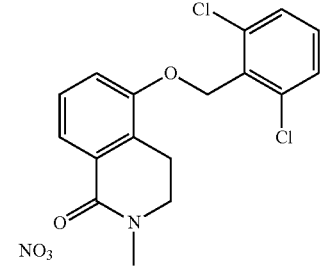 |
| 2-23 | 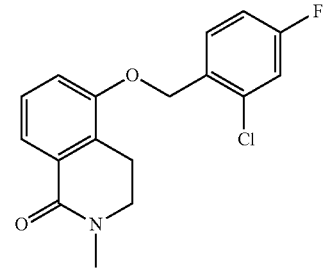 [SMILES: CN1CCc2c(OCc3ccc(F)cc3Cl)cccc2C1=O] |
| Cpd. No. | Structure |
|---|---|
| 2-24 | 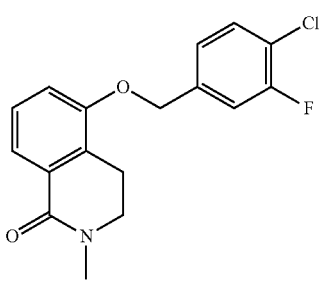 |
| 2-25 | 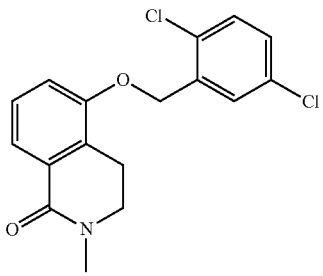 [SMILES: CN1CCc2c(OCc3cc(Cl)ccc3Cl)cccc2C1=O] |
| 2-26 | 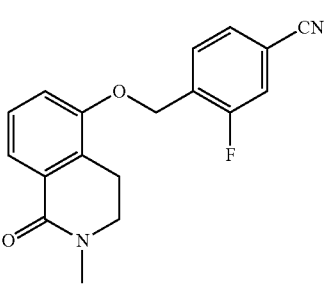 [SMILES: CN1CCc2c(OCc3ccc(C#N)cc3F)cccc2C1=O] |
| 2-27 | 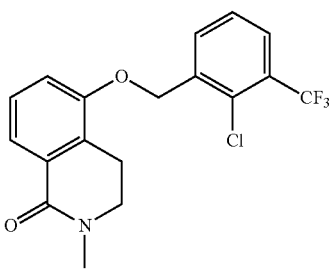 [SMILES: CN1CCc2c(OCc3cccc(C(F)(F)F)c3Cl)cccc2C1=O] |
| 2-28 | 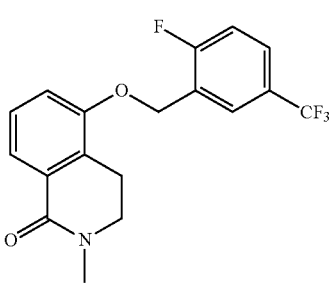 [SMILES: CN1CCc2c(OCc3cc(C(F)(F)F)ccc3F)cccc2C1=O] |

| Cpd. No. | Structure |
|---|---|
| 2-29 | 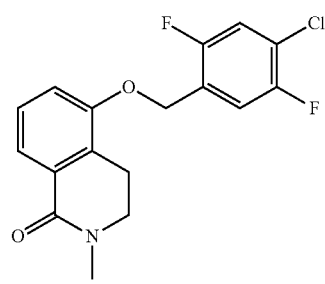 |
| 2-30 | 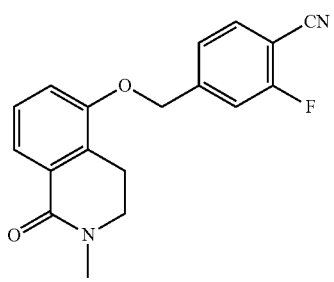 [SMILES: CN1CCc2c(OCc3ccc(C#N)c(F)c3)cccc2C1=O] |
| 2-31 | 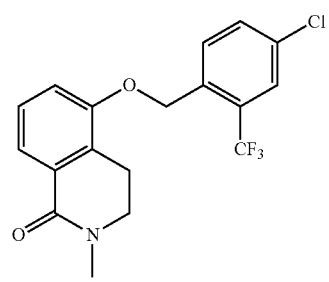 |
| 2-32 | 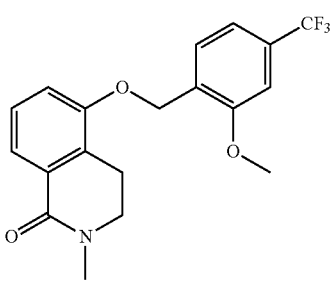 [SMILES: COc1cc(C(F)(F)F)ccc1COc1cccc2c1CCN(C)C2=O] |
| 2-33 | 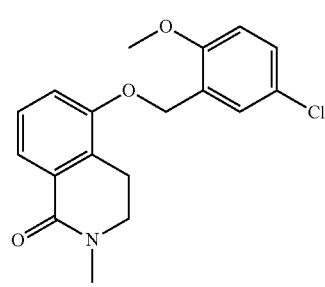 [SMILES: COc1ccc(Cl)cc1COc1cccc2c1CCN(C)C2=O] |
| Cpd. No. | Structure |
|---|---|
| 2-34 | 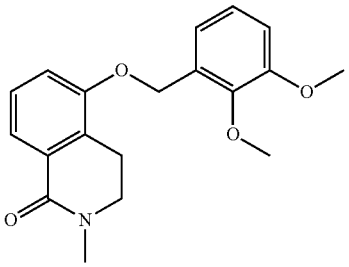 [SMILES: COc1cccc(COc2cccc3c2CCN(C)C3=O)c1OC] |
| 2-35 | 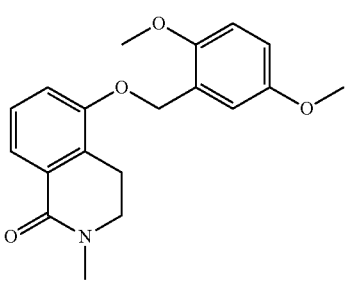 [SMILES: COc1ccc(OC)c(COc2cccc3c2CCN(C)C3=O)c1] |
| 2-36 | 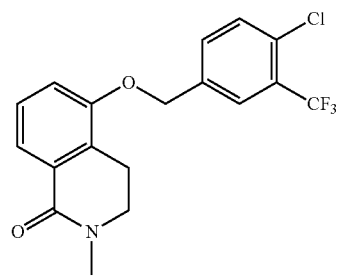 [SMILES: CN1CCc2c(OCc3ccc(Cl)c(C(F)(F)F)c3)cccc2C1=O] |
| 2-37 | 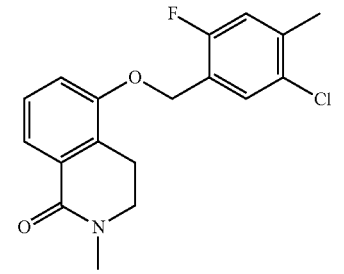 [SMILES: Cc1cc(F)c(COc2cccc3c2CCN(C)C3=O)cc1Cl] |
| 2-38 | 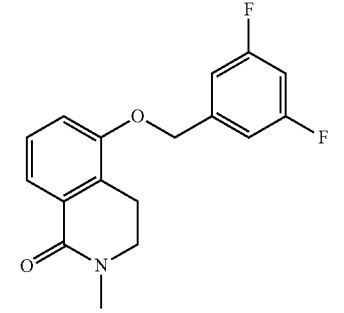 [SMILES: CN1CCc2c(OCc3cc(F)cc(F)c3)cccc2C1=O] |

| Cpd. No. | Structure |
|---|---|
| 2-39 | 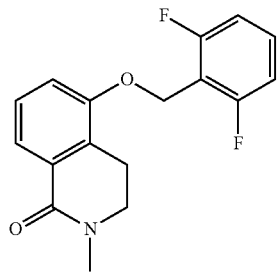 [SMILES: CN1CCc2c(OCc3c(F)cccc3F)cccc2C1=O] |
| 2-40 | 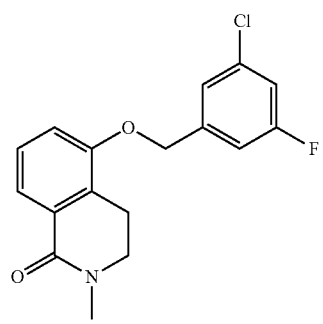 |
| 2-41 | 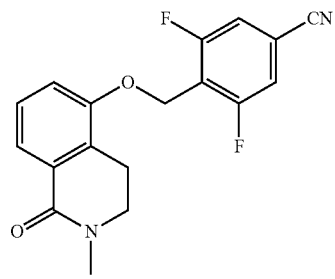 [SMILES: CN1CCc2c(OCc3c(F)cc(C#N)cc3F)cccc2C1=O] |
| 2-42 | 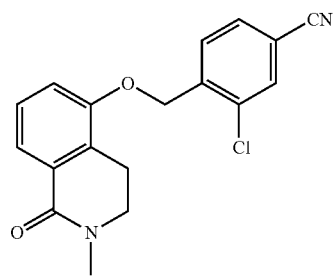 |
| 2-43 | 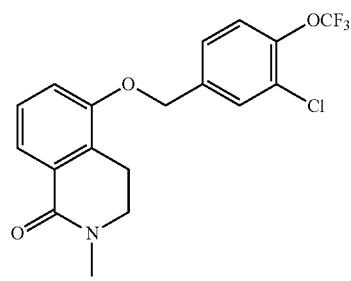 [SMILES: CN1CCc2c(OCc3ccc(OC(F)(F)F)c(Cl)c3)cccc2C1=O] |
| Cpd. No. | Structure |
|---|---|
| 2-44 | 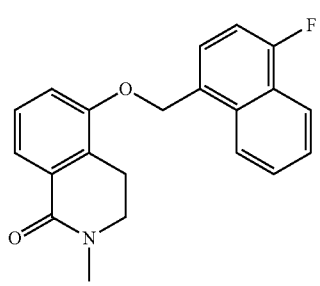 [SMILES: CN1CCc2c(OCc3ccc(F)c4ccccc34)cccc2C1=O] |
| 2-45 | 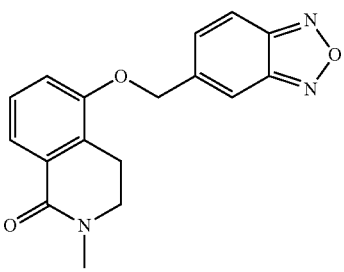 [SMILES: CN1CCc2c(OCc3ccc4nonc4c3)cccc2C1=O] |
| 2-46 | 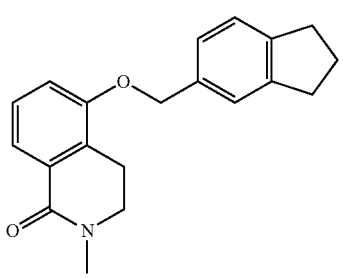 [SMILES: CN1CCc2c(OCc3ccc4c(c3)CCC4)cccc2C1=O] |
| 3-1 | 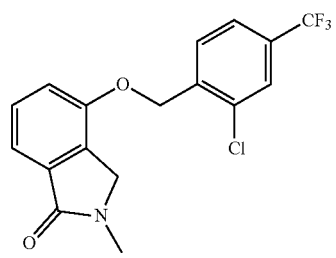 [SMILES: CN1Cc2c(OCc3ccc(C(F)(F)F)cc3Cl)cccc2C1=O] |
| 3-2 | 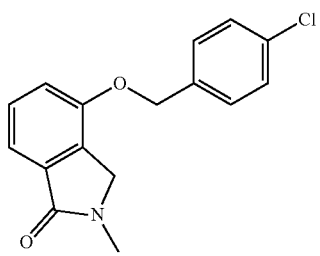 [SMILES: CN1Cc2c(OCc3ccc(Cl)cc3)cccc2C1=O] |

-continued
| Cpd. No. | Structure |
|---|---|
| 4-1 | 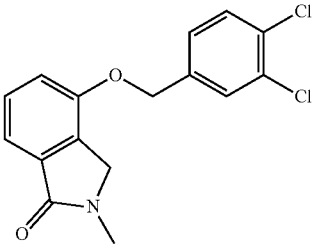 [SMILES: CN1Cc2c(OCc3ccc(Cl)c(Cl)c3)cccc2C1=O] |
| 4-2 | 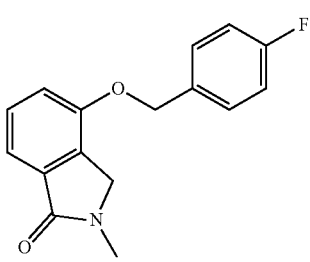 [SMILES: CN1Cc2c(OCc3ccc(F)cc3)cccc2C1=O] |
| 4-3 | 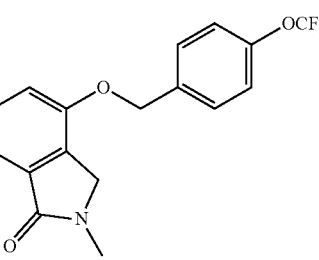 |
| 4-4 | 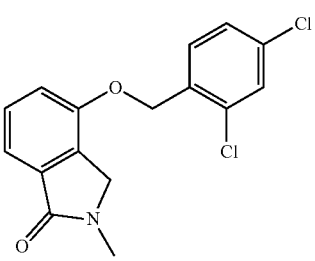 |
| 4-5 | 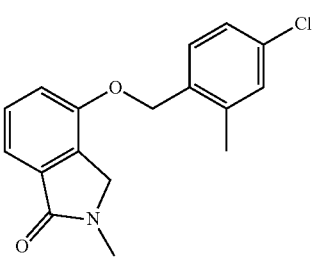 [SMILES: Cc1cc(Cl)ccc1COc1cccc2c1CN(C)C2=O] |
| 4-6 | 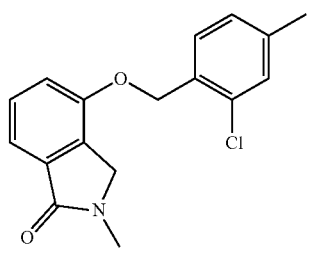 [SMILES: Cc1ccc(COc2cccc3c2CN(C)C3=O)c(Cl)c1] |
-continued
| Cpd. No. | Structure |
|---|---|
| 4-7 | 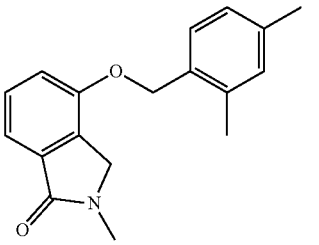 [SMILES: Cc1ccc(COc2cccc3c2CN(C)C3=O)c(C)c1] |
| 5-1 | 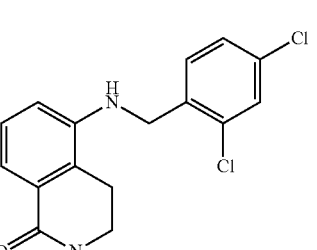 |
| 5-2 | 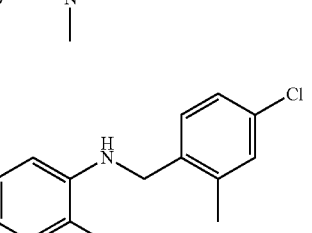 |
| 5-3 | 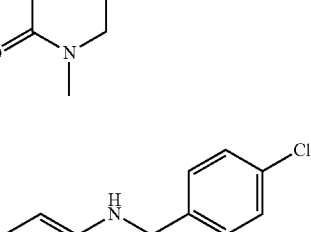 |
| 5-4 | 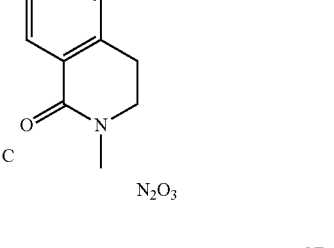 |

| Cpd. No. | Structure |
|---|---|
| 6-1 | 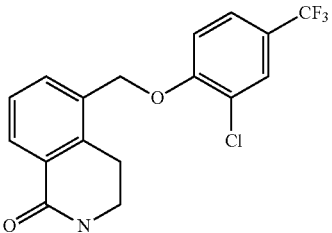 |
| 6-2 | 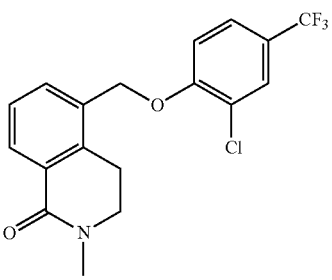 [SMILES: CN1CCc2c(COc3ccc(C(F)(F)F)cc3Cl)cccc2C1=O] |
| 7-1 | 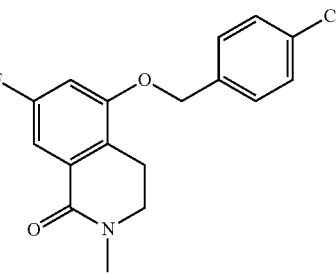 |
| 7-2 | 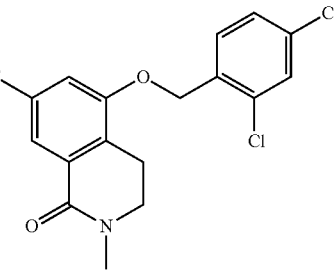 |
| 8-1 | 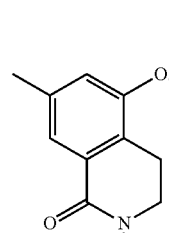 |
| 8-2 | 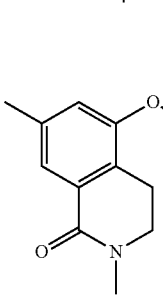 |

5. A pharmaceutical composition comprising a compound of any one of claim 1-3 or 4, or a pharmaceutically acceptable isomer, racemate, hydrate, solvate, isotope, or salt thereof, and a pharmaceutically acceptable excipient.

6. A method for modulating a Mas-Related G-Protein Receptor (MRGPR) X4 by contacting the MRGPR X4 with an effective amount of a compound having the structure of any one of claim 1, 2, 3 or 4, or a pharmaceutically acceptable isomer, racemate, hydrate, solvate, isotope, or salt thereof.

7. A method for treating pain comprising administering to a subject in need thereof an effective amount of a compound having the structure of any one of claim 1, 2, 3 or 4, or a pharmaceutically acceptable isomer, racemate, hydrate, solvate, isotope, or salt thereof.

8. A method for treating itch comprising administering to a subject in need thereof an effective amount of a compound having the structure of any one of claim 1, 2, 3 or 4, or a pharmaceutically acceptable isomer, racemate, hydrate, solvate, isotope, or salt thereof.

* * * * *

UNITED STATES PATENT AND TRADEMARK OFFICE
CERTIFICATE OF CORRECTION

Page 1 of 1

PATENT NO. : 11,787,767 B2
APPLICATION NO. : 17/231834
DATED : October 17, 2023
INVENTOR(S) : Marcos Sainz et al.

It is certified that error appears in the above-identified patent and that said Letters Patent is hereby corrected as shown below:

In the Claims

Column 112, Claim 5, Line 29:
"any one of claim 1-3 or 4,"
Should read:
--any one of claims 1-3 or 4,--.

Column 112, Claim 6, Line 35:
"any one of claim 1, 2, 3 or 4,"
Should read:
--any one of claims 1, 2, 3 or 4,--.

Column 112, Claim 7, Line 40:
"any one of claim 1, 2, 3 or 4,"
Should read:
--any one of claims 1, 2, 3 or 4,--.

Column 112, Claim 8, Line 45:
"any one of claim 1, 2, 3, or 4,"
Should read:
--any one of claims 1, 2, 3 or 4,--.

Signed and Sealed this
Sixth Day of May, 2025

Coke Morgan Stewart
*Acting Director of the United States Patent and Trademark Office*